US006441156B1

(12) United States Patent
Lerman et al.

(10) Patent No.: US 6,441,156 B1
(45) Date of Patent: Aug. 27, 2002

(54) CALCIUM CHANNEL COMPOSITIONS AND METHODS OF USE THEREOF

(75) Inventors: Michael Isaac Lerman, Rockville, MD (US); Farida Latif, Birmingham (GB); Ming-Hui Wei, Germantown; Fuh-Mei Duh, Ellicot City, both of MD (US); John Dorrance Minna, Dallas, TX (US); Yoshitaka Sekido, Nagoya (JP); Boning Gao, Dallas, TX (US)

(73) Assignee: The United States of America as represented by the Department of Health and Human Services, Rockville, MD (US)

( * ) Notice: Subject to any disclaimer, the term of this patent is extended or adjusted under 35 U.S.C. 154(b) by 0 days.

(21) Appl. No.: 09/470,443

(22) Filed: Dec. 22, 1999

Related U.S. Application Data
(60) Provisional application No. 60/114,359, filed on Dec. 30, 1998.

(51) Int. Cl.[7] .......................... C07H 21/02; C07H 21/04; C12N 15/00; C12N 15/09; C12N 15/63
(52) U.S. Cl. .................. 536/23.5; 536/23.1; 435/320.1; 435/325; 435/455; 530/350
(58) Field of Search .............................. 536/23.1, 23.5; 435/320.1, 325, 455; 530/350

(56) References Cited

U.S. PATENT DOCUMENTS

| | | |
|---|---|---|
| 4,650,764 A | 3/1987 | Temin et al. |
| 4,683,195 A | 7/1987 | Mullis et al. |
| 4,683,202 A | 7/1987 | Mullis |
| 4,797,368 A | 1/1989 | Carter et al. |
| 4,861,719 A | 8/1989 | Miller |
| 4,946,778 A | 8/1990 | Ladner et al. |
| 4,965,188 A | 10/1990 | Mullis et al. |
| 4,980,289 A | 12/1990 | Temin et al. |
| 5,124,263 A | 6/1992 | Temin et al. |
| 5,139,941 A | 8/1992 | Muzyczka et al. |
| 5,312,928 A | 5/1994 | Goldin et al. |
| 5,399,346 A | 3/1995 | Anderson et al. |
| 5,407,820 A | 4/1995 | Ellis et al. |
| 5,429,921 A | 7/1995 | Harpold et al. |
| 5,459,127 A | 10/1995 | Felgner et al. |
| 5,559,004 A | 9/1996 | Steinhardt et al. |
| 5,569,825 A | 10/1996 | Lonberg et al. |
| 5,580,859 A | 12/1996 | Felgner et al. |
| 5,589,466 A | 12/1996 | Felgner et al. |
| 5,618,720 A | 4/1997 | Ellis et al. |
| 5,625,126 A | 4/1997 | Lonberg et al. |
| 5,686,241 A | 11/1997 | Ellis et al. |
| 5,710,250 A | 1/1998 | Ellis et al. |
| 5,792,846 A | 8/1998 | Harpold et al. |
| 5,843,742 A | 12/1998 | Natsoulis et al. |

FOREIGN PATENT DOCUMENTS

| | | |
|---|---|---|
| EP | 453243 | 10/1991 |
| EP | 178220 | 1/1992 |
| EP | 185573 | 5/1992 |
| EP | 488528 | 11/1995 |
| WO | 89/07150 | 8/1989 |
| WO | 90/02806 | 3/1990 |
| WO | 90/13678 | 11/1990 |
| WO | 91/18088 | 11/1991 |
| WO | 92/05263 | 4/1992 |
| WO | 93/09239 | 5/1993 |
| WO | 94/12649 | 6/1994 |
| WO | 94/21807 | 9/1994 |
| WO | 94/26914 | 11/1994 |
| WO | 94/28152 | 12/1994 |
| WO | 94/28938 | 12/1994 |
| WO | 95/02697 | 1/1995 |
| WO | 95/07358 | 3/1995 |
| WO | 95/18863 | 7/1995 |
| WO | 95/21931 | 8/1995 |
| WO | 96/15244 | 5/1996 |
| WO | 96/17823 | 6/1996 |
| WO | 96/22378 | 7/1996 |
| WO | 96/25508 | 8/1996 |

OTHER PUBLICATIONS

Bowie et al, 1990, Science, 247: 1306–1310.*
Brown et al, 1998, J. Biol. Chem., 273(39):25458–25465.*
Wiser et al, 1996, FEBS Letters, 397: 15–20.*
Burgess et al, 1990, J. Cell Biol., 111: 2129–2138.*
Lazar et al, 1988, Mol. Cell. Biol., 8(3): 1247–1252.*
Research Disclosure 37105, "Recombinant Herpesvirus Lacking Gene for Glycoprotein L," Mar. 1995.
Alton et al., "Non–invasive liposome–mediated gene delivery can correct the ion transport defect in cystic fibrosis mutant mice," Nature Genet., 5:135–142 [1993].
Angelotti and Hofmann, "Tissue–specific expression of splice variants of the mouse voltage–gated calcium channel $\alpha_2/\delta$ subunit," FEBS 397:331–337 [1996].
Ausubel et al., *Current Protocols in Molecular Biology*, John Wiley & Sons, New York NY [1989].
Bangalore et al., "Influence of L–type Ca channel $\alpha_2/\delta$–subunit on ionic and gating current in transiently transfected HEK 293 cells, " Am. J. Physiol. 270(5 Pt. 2):H1521–1528 [1996].
Barclay et al., "Mouse Models of Spike–Wave Epilepsy," Epilepsia 40(Suppl.) 3:17–22 [1999].
Baylin et al., "Alterations in DNA Methylation: A Fundamental Aspect of Neoplasia," Adv. Cancer Res. 72:141–196 [1998].
Becker et al., In Protein Expression in Animal Cells, Roth et al. (eds.) [1994].

(List continued on next page.)

Primary Examiner—Deborah J. R. Clark
Assistant Examiner—Peter Paras, Jr.
(74) Attorney, Agent, or Firm—Medlen & Carroll, LLP

(57) ABSTRACT

The present invention relates to calcium channel compositions and methods of making and using same. In particular, the invention relates to calcium channel alpha2delta ($\alpha_2\delta$) subunits and nucleic acid sequences encoding them. These compositions are useful in methods for identifying compounds that modulate the activity of calcium channels and for identifying compounds as therapeutic for disease.

18 Claims, 5 Drawing Sheets

OTHER PUBLICATIONS

Bender et al., "Evidence that the Packaging Signal of Moloney Murine Leukemia Virus Extends into the gag region," J. Virol. 61:1639–1646 [1987].

Bernstein et al., "Gene Transfer with Retrovirus Vectors," Genet. Eng.;235–261 [1985].

Berridge et al., "Calcium—a life and death signal, " Nature 395:645–648 [1998].

Biel et al., "Primary structure and functional expression of a high voltage activated calcium channel from rabbit lung," FEBS 269:409–412 [1990].

Black et al., "Identification and Cloning of Putative Human Neuronal Voltage–Gated Calcium Channel α–2 and α–3 Subunits: Neurologic Implications," Mayo Clin. Proc. 74(4):357–361 [1999].

Bork et al., "More von Willebrand factor type A domains? Sequence similarities with malaria thrombospondin–related anonymous protein, dihydropyridine–sensitive calcium channel and inter–α–trypsin inhibitor," Biochem. J. 279:908–10 [1991.

Brown and Gee, "Cloning and Deletion Mutagenesis of the $\alpha_2\delta$ Calcium Channel Subunit from Porcine Cerebral Cortex. Expression of a Soluble Form of the Protein that Retains [$^3$H] Gabapentin Binding Activity,"J. Biol. Chem., 273:25458–25465 [1998].

Brust et al., "Human Neuronal Voltage–Dependent Calcium Channels: Studies on Subunit Structure and Role in Channel Assembly," Neuropharmacol. 32:1089–1102 [1993].

Burgess et al., "Mutation of the $Ca^{2+}$Channel β Subunit Gene Cchb4 is Associated with Ataxia and Seizures in the Lethargic (1h) Mouse," Cell 88:385–392 [1997].

Caplen et al., "Gene therapy for cystic fibrosis in humans by liposome–mediated DNA transfer: the production of resources and the regulatory process," Gene Ther. 1:139–147 [1994].

Castellano and Perez–Reyes, "Molecular diversity of $Ca^{2+}$ channel β subunits," Biochem. Soc. Trans. 22:483–488 [1994].

Chiorini et al., "Cloning of Adeno–Associated Virus Type 4 (AAV4) and Generation of Recombinant AAV4 Particles," J. Virol. 71:6823–6833 [1997].

Chiorini et al., "Cloning and Characterization of Adeno–Associated Vrius Type 5," J. Virol. 73:1309–1319 [1999].

Cole et al., "The EBV–Hybridoma Technique and its Application to Human Lung Cancer," in *Monoclonal Antibodies and Cancer Therapy*, Reisfeld et al. (eds.), pp. 77–96, Alan R. Liss, Inc. [1985].

Coombs, *Dictionary of Biotechnology*, Stockton Press, New York NY [1994].

Cote et al., "Generation of human monoclonal antibodies reactive with cellular antigens," Proc. Natl. Acad. Sci. USA 80:2026–2030 [1983].

Curiel et al., "High–Efficiency Gene Transfer Mediated by Adenovirus Coupled to DNA–Polylysine complexes," Hum. Gene Ther. 3:147–154 [1992].

Davidson et al., "A model system for in vivo gene transfer into the central nervous system using an adenoviral vector," Nature Genet. 3:219–223 [1993].

De Jongh et al., "Subunits of Purified Calcium Channels. α2 and δ are Encoded by the Same Gene," J. Biol. Chem. 265:14738–14741 [1990].

De Koninck and Schulman, "Sensitivity of CaM Kinase II to the Frequency of $Ca^{2+}$ Oscillations," Science 279:227–30 [1998].

Dieffenbach and Dveksler, *PCR Primer, a Laboratory Manual*, Cold Spring Harbor Press, Plainview NY [1995] (Applicants will provide Title and Copyright Pages should the Examiner desire copies of these pages).

Dolphin et al., "The effect of a α2–δ and other accessory subunits on expression and properties of the calcium channel α1G," J. Physiol. 519.1:35–45 [1999].

Ellis et al., "Sequence and Expression of mRNAs Encoding the $\alpha_1$ and $\alpha_2$ Subunits of a DHP–Sensitive Calcium Channel," Science 241:1661–1664 [1988].

Engelhardt et al., "Ablation of E2A in recombinant adenoviruses improves transgene persistence and decreases inflammatory in mouse liver," Proc. Natl. Acad. Sci. USA 91:6196–6200 [1994].

Estacion and Mordan, "PDGF–Stimulated Calcium Influx Changes During In Vitro Cell Transformation,"Cell Signal 9:363–366 [1997].

Felgner and Ringold, "Cationic liposome–mediated transfection," Nature 337:387–388 [1989].

Felgner et al., "Lipofection: A highly efficient, lipid–mediated DNA–transfection procedure," Proc. Natl. Acad. Sci. USA 84: 7413–7417 [1987].

Felgner, "Particulate systems and polymers for in vitro and in vivo delivery of polynucleotides," Adv. Drug Del. Rev. 5:163–187 [1990].

Graham, "Covalently closed circles of human adenovirus DNA are infections," EMBO J. 3:2917–2922 [1984].

Graham et al., "Characteristics of a Human Cell Line Transformed by DNA from Human Adenovirus type 5," J. Gen. Virol. 36:59–74 [1977].

Graham and Prevec, "Manipulation of Adenovirus Vectors," Meth. Molec. Biol. 7:109–128 [1991].

Gurnett et al., "Dual Function of the Voltage–Dependent $Ca^{2+}$ Channel $\alpha_2\delta$ Subunit in Current Stimulation and Subunit Interaction," Neuron 16:431–400 [1996].

Hermonat et al., "Use of adeno–associated virus as a mammalian DNA cloning vector: Trandsduction of neomycin resistance into mammalian tissue culture cells," Proc. Natl. Acad. Sci. USA 81:6466–6470 [1984].

Huse et al., "Generation of a Large Combinatorial Library of the Immunoglobulin Repertoire in Phage Lambda," Science 246: 1275–1281 [1989].

Jones et al., "Mechanism of Auxiliary Subunit Modulation of Neuronal 1E Calcium Channels," J. Gen. Physiol. 112:125–143 [1998].

Juretic and Lucin, "The Preference Functions Method for Predicting Protein Helical Turns with Membrane Propensity," J. Chem. Inf. Comput. Sci. 38: 575–585 [1998].

Kaplitt et al., "Expression of a Functional Foreign Gene in Adult Mammalian Brain following in Vivo Transfer via a Herpes Simplex Virus Type 1 Defective Viral Vector," Mol. Cell. Neurosci. 2:320–330 [1991].

Klugbauer et al., "Molecular Diversity of the Calcium Channel $\alpha_2\delta$ Subunit," J. Neurosci. 19:684–691 [1999].

Kohler and Milstein, "Continuous cultures of fused cells secreting antibody of predefined specificity," Nature 256:495–497 [1975].

Kozbor et al., "The production of monoclonal antibodies from human lymphocytes," Immun. Today 4:72–79 [1983].

Kuo et al., "Efficient Gene Transfer Into Primary Murine Lymphocytes Obviating the Need for Drug Selection," Blood 82:845–852 [1993].

La Salle et al., "An Adenovirus Vector for Gene Transfer into Neurons and Glia in the Brain," Science 259:988–990 [1993].

Lebkowski et al., "Adeno–Associated Virus: a Vector System for Efficient Introduction and Integration of DNA into a Variety of Mammalian Cell Types," Mol. Cell. Biol. 8:3988–3996 [1988].

Ledley, "Nonviral Gene Therapy: The Promise of Genes as Pharmaceutical Products," Hum. Gene Ther. 6:1129–1144 [1995].

Lehmann–Horn and Jurkatt–Roth, "Voltage–Gated Ion Channels and Hereditary Disease," Physiol. Rev. 79:1317–1372 [1999].

Lennon et al., "Calcium–channel antibodies in the Lambert–Eaton syndrome and other paraneoplastic syndromes," New Engl. J. Med. 332:1467–1474 [1995].

Letts et al., "The mouse stargazer gene encodes a neuronal $Ca^{2+}$ channel γ subunit," Nat. Genet. 19:340–347 [1998].

Levrero et al., "Defective and nondefective adenovirus vectors for expressing foreign genes in vitro and in vivo," Gene 101:195–202 [1991].

Lory et al., "Towards a unified nomenclature describing voltage–gated calcium channel genes," Hum. Genet. 100:149–150 [1997].

Machy, et al., "Gene transfer from targeted liposomes to specific lymphoid cells by electrophoresis," Proc. Natl. Acad. Sci. USA 85:8027–8031 [1988].

Mann et al., "Construction of a Retrovirus Packaging Mutant and Its Use to Produce Helper–Free Defective Retrovirus," Cell 33:153–159 [1983].

Markowitz et al., "A Safe Packaging Line for Gene Transfer: Separating Viral Genes on Two Different Plasmids," J. Virol. 62:1120–1124 [1988].

McCormick, "Human Gene Therapy: The First Round," BioTechnol. 3:689–693 [1985].

McEnery et al., "Differential Expression and Association of Calcium Channel Subunits in Development and Disease," J. Bioenerg. Biomembr. 30:409–418 [1998].

McEnery et al., "Purified omega–conotoxin GVIA receptor of rat brain resembles a dihydropyridine–sensitive L–type calcium channel," Proc. Natl. Acad. Sci. USA 88:11095–11099 [1991].

Miller, "Calcium channels prove to be a real headache," Trends Neurosci. 20:189–192 [1997].

Miller and Rosman, "Improved Retroviral Vectors for Gene Transfer and Expression," BioTechniques 7:980–990 [1992].

Nabel et al., "Direct gene transfer with DNA–liposome complexes in melanoma: expression, biologic activity, and lack of toxicity in humans," Proc. Natl. Acad. Sci. USA 90:11307–11311 [1993].

Nagese et al., "Prediction of the Coding Sequences of Unidentified Human Genes., IX. The Complete Sequences of 100 New cDNA Clones from Brain Which Can Code for Large Proteins in vitro," DNA Res. 5:31–39 [1998].

Nakai and Kanehisa, "A Knowledge Base for Predicting Protein Localization Sites in Eukaryotic cells," Genomics 14:897–911 [1992].

O'Neill et al., "The Lambert–Eaton Myasthenic Syndrome. A Review of 50 cases," Brain 111:577–596 [1988].

Perez–Reyes and Schneider, "Molecular biology of calcium channels," Kidney Int. 48:1111–1124 [1995].

Prestridge, "Predicting Pol II Promoter Sequences using Transcription Factor Binding Site," J. Mol. Biol. 249:923–932 [1995].

Qin et al., "Modulation of human neuronal $\alpha_{1E}$–type calcium channel by $\alpha_2\delta$–subunit," J. Gen. Physiol., 274(5 Pt. 1):C1324–1331 [1998].

Raymond et al., "Antibodies against the β subunit of voltage–dependent calcium channels in Lambert–Eaton myasthenic syndrome," Neurosci. 90:269–277 [1999].

Sambrook et al., *Molecular Cloning, A Laboratory Manual*, Cold Spring Harbor Press, Plainview NY [1989].

Samulski et al., "A Recombinant Plasmid from Which an Infectious Adeno–Associated Virus Genome Can Be Excised In Vitro and Its Use To Study Viral Replication," J. Virol. 61: 3096–3101 [1987].

Samulski et al., "Helper–Free Stocks of Recombinant Adeno–Associated Viruses: Normal Integration Does Not Require Viral Gene Expression," J. Virol. 63:3822–3828 [1989].

Sanford et al., "Optimizing the Biolistic Process for Different Biological Applications," Meth. Enzymol. 217:483–509 [1993].

Schmid et al., "Immunochemical Analysis of Subunit Structures of 1,4–Dihydropyridine Receptors Associated with Voltage–Dependent $Ca^{2+}$ Channels in Skeletal, Cardiac, and Smooth Muscles," Biochem. 25:3492–3495 [1986].

Schmutte and Jones, "Involvement of DNA Methylation in Human Carcinogenesis," Biol. Chem. 379:377–388 [1998].

Sekido et al., "Cloning of a breast cancer homozygous deletion junction narrows the region of search for a 3p21.3 tumor suppressor gene," Oncogene 16:3151–3157 [1998].

Sekido et al., "Neurofibromatosis Type 2 (NF2) Gene is Somatically Mutated in Mesothelioma but not in Lung Cancer," Cancer Res. 55:1227–1231 [1995].

Sekido et al., "Human semaphorins A(V) and IV reside in the 3p21.3 small cell lung cancer deletion region and demonstrate distinct expression patters," Proc. Natl. Acad. Sci USA 93:4120–4125 [1996].

Shaked et al., "Adenovirus–mediated gene transfer in the transplant setting. II. Successful expression of transferred cDNA in syngeneic liver grafts," Transplant. 57:1508–1511 [1994].

Sharp and Campbell, "Characterization of the 1,4–Dihydropyridine Receptor Using Subunit–specific Polyclonoal Antibodies. Evidence for a 32,000–Da subunit," J. Biol. Chem. 264:2816–2825 [1989].

Shirokov et al., "Inactivation of Gating Currents of L–type Calcium Channels. *Specific role of the $\alpha_2\delta$ subunit,*" J. Gen. Physiol. 111:807–823 [1998].

Singer et al., "The Roles of the Subunits in the Function of the Calcium Channel," Science 253:1553–1557 [1991].

Smith et al., "Liposomes as agents of DNA transfer," Biochem. Biophys. Acta 1154:327–340 [1993].

Sonnhammer et al., "Pfam: multiple sequence alignments and HMM–profiles of protein domains," Nucl. Acids Res. 26:320–322 [1998].

Sonnhammer et al., "Pfam: A Comprehensive Database of Protein Domain Families Based on Seed Alignments," Proteins: Structure, Function, and Genetics 28:405–420 [1997].

Stefani et al., "Gabapentin inhibits calcium currents in isolated rat brain neurons," Neuropharmacol. 37:83–91 [1998].

Stratford–Perricaudet et al., "Widespread Long–term Gene Transfer to Mouse Skeletal Muscles and Heart, " J. Clin. Invest. 90:626–630 [1992].

Suh–Kim et al., "Reconstitution of the Skeletal Muscle Dihydropyridine receptor. Functional interaction among $\alpha 1$, $\beta$, $\gamma$ and $\alpha_2\delta$ subunits," Recept. Channels 4:217–225 [1996].

Takamori, "An Autoimmune Channelopathy Associated with Cancer: Lambert–Eaton Myasthenic Syndrome," Intern. Med. 38:86–96 [1999].

Tang et al., "Genetic immunization is a simple method for elicting an immune response," Nature 356:152–154 [1992].

Toyota et al., "Aberrant Methylation in Gastric Cancer Associated with the CpG Island Methylator Phenotype," Cancer Res. 59:5438–5442 [1999].

Ulmer et al., "Heterologous Protection Against Influenza by Injection of DNA Encoding a Viral Protein,"Science 259:1745–1748 [1993.

Voltz et al., "P/Q–type Voltage–Gated Calcium Channel Antibodies in Paraneoplastic Disorders of the Central Nervous System," Muscle & Nerve 22:119–122 [1999].

Walker and De Waard, "Subunit interaction sites in voltage–dependent $Ca^{2+}$ channels: role in channel function," Trends Neurosci. 21;148–54 [1998].

Wei et al., "Molecular Determinants of Cardiac $Ca^{2+}$ Channel Pharmacology," J. Biol. Chem. 270:27106–27111 [1995].

Wei et al., "Construction of a 6000–Kilobase Cosmid Clone Contig and Generation of a Transcriptional Map Surrounding the Lung Cancer Tumor Suppressor Gene (TSG) Locus on Human Chromosome 3p21.3: Progress toward the Isolation of a Lung Cancer TSG," Cancer Res. 56:1487–1492 [1996].

Welling et al., "Hormonal regulation of calcium current in freshly isolated airway smooth muscle cells," Am. J. Physiol. 262:L351–359 [1992].

Williams et al., "Structure and Functional Expression of $\alpha_1$, $\alpha_2$, and $\beta$ Subunits of a Novel Human Neuronal Calcium Channel Subtype," Neuron 8:71–84 [1992].

Williams et al., "Introduction of foreign genes into tissues of living mice by DNA–coated microprojectiles," Proc. Natl. Acad. Sci. USA 88:2726–2730 [1991].

Wistuba et al., "Molecular Damage in the Bronchial Epithelium of Current and Former Smokers," J. Natl. Cancer Instit. 89:1366–1377 [1997].

Wu et al., "Coordinated Leading–and Lagging–strand Synthesis at the *Escherichia coli* DNA Replication Fork," J. Biol. Chem. 267:4030–4044 [1992].

Wu and Wu, "Receptor–mediated Gene Delivery and Expression in Vivo," J. Biol. Chem. 263:14621–14624 [1988].

Wu and Wu, "Receptor–mediated in Vitro Gene Transformation by a Soluble DNA Carrier System," J. Biol. Chem. 262:4429–4432 [1987].

Morton et al., "$\alpha_1$ and $\alpha_2$ $Ca^{2+}$channel subunit expression in human neuronal and small cell carcinoma," FASEB J., 8(11):884–888 [1994].

Rojas, "Ion Channels and Human Genetic Diseases," News Physiol. Sci., 11:36 [1996].

Gurnett and Campbell, "Transmembrane auxiliary subunits of voltage–dependent ion channels," J. Biol. Chem., 271(45):27975–27978 (1996).

Jones, "Overview of Voltage–dependent Calcium Channels," J. Bioenergetics and Biomembranes 30(4):299–312 (Aug., 1998).

Ophoff et al., "P/Q–type $Ca^{2+}$ channel defects in migraine, ataxia and epilepsy," Trends Phys. Sci., 19:121–127 (Apr. 1998).

Randall, "The Molecular Basis of Voltage–gated $Ca^{2+}$ channel diversity: is it Time for T?," J. Membrane Biol., 161:207–213 (Feb., 1998).

Felgner, "Prospects for Synthetic Self–Assembling Systems in Gene Delivery," J. Gene Med. 1:290–292 [1999].

McEnery et al., "Isolation of the mitochondrial benzodiazepine receptor: Association with the voltage–dependent anion channel and the adenine nucleotide carrier," Proc. Natl. Acad. Sci. USA 89:3170–3174 [1992.

Takamori et al., "Lambert–Eaton myasthenic syndrome as an autoimmune calcium–channelopathy," Neurosci. Res. 36:183–191 [2000].

* cited by examiner

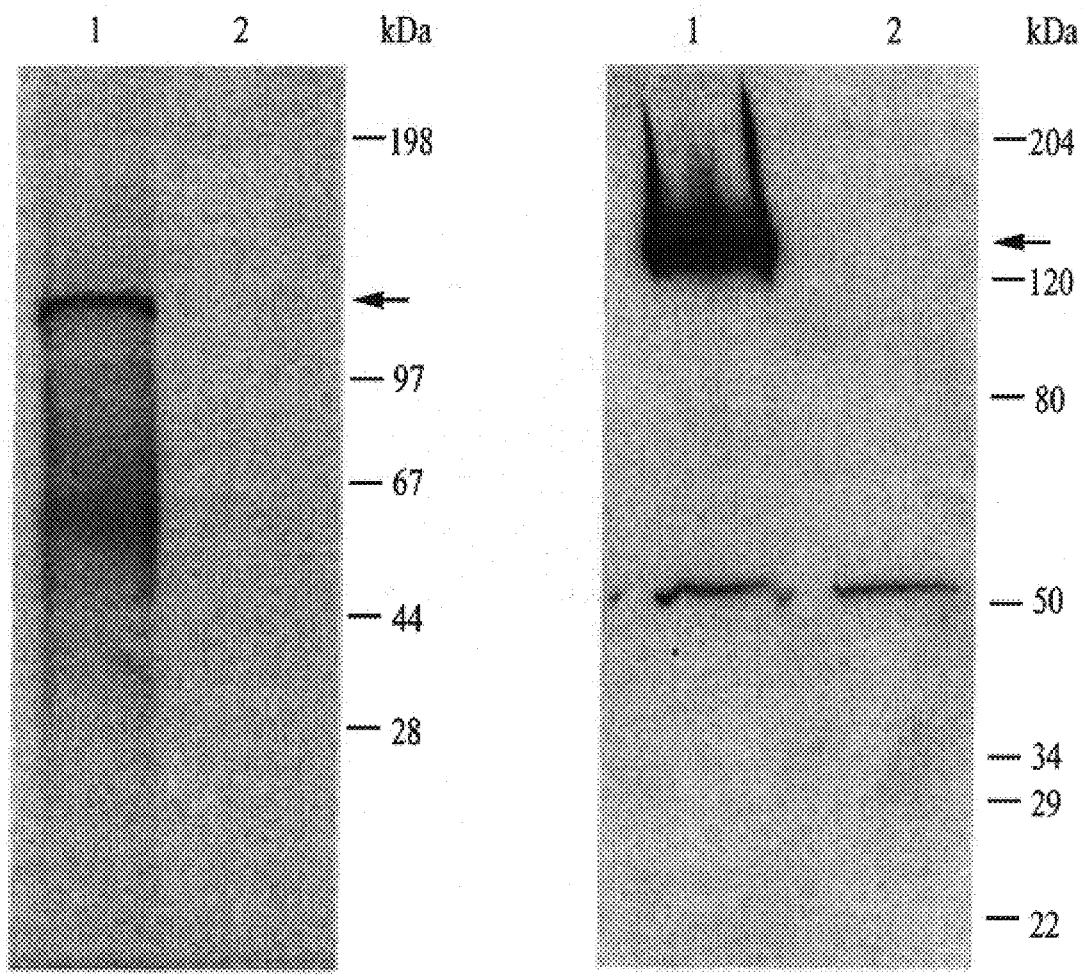
FIG. 3A
FIG. 3B
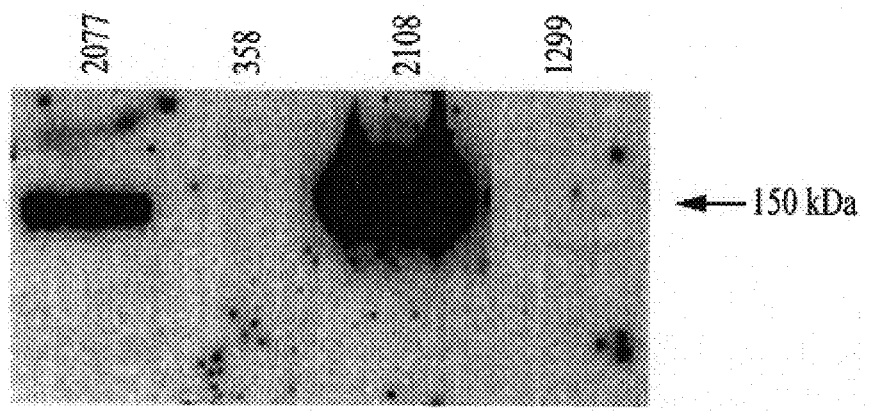
FIG. 3C

SEQUENCE LISTING

<160> NUMBER OF SEQ ID NOS: 114

<210> SEQ ID NO 1
<211> LENGTH: 5463
<212> TYPE: DNA
<213> ORGANISM: Homo sapiens
<220> FEATURE:
<221> NAME/KEY: CDS
<222> LOCATION: (162)..(3599)

<400> SEQUENCE: 1

```
gccagcgctg cagggagata gcagcgcgca gcccgcagag gcgctgcggc ccgtgcagcc        60
ccggaggccc ctcgcggaga aggcggcggc ggaggagagg ccgagttacc gcccgccgcc       120 cgcgccccc ctccccgcgg cgccgcatct tgaatggaaa c atg gcg gtg ccg gct       176
                                             Met Ala Val Pro Ala
                                             1               5 cgg acc tgc ggc gcc tct cgg ccc ggc cca gcg cgg act gcg cgc ccc       224
Arg Thr Cys Gly Ala Ser Arg Pro Gly Pro Ala Arg Thr Ala Arg Pro
            10                  15                  20 tgg ccc ggc tgc ggc ccc cac cct ggc ccc ggc acc cgg cgc ccg acg       272
Trp Pro Gly Cys Gly Pro His Pro Gly Pro Gly Thr Arg Arg Pro Thr
        25                  30                  35 tcc ggg ccc ccg cgc ccg ctg tgg ctg ctg ctg ccg ctt cta ccg ctg       320
Ser Gly Pro Pro Arg Pro Leu Trp Leu Leu Leu Pro Leu Leu Pro Leu
    40                  45                  50 ctc gcc gcc ccc ggc gcc tct gcc tac agc ttc ccc cag cag cac acg       368
Leu Ala Ala Pro Gly Ala Ser Ala Tyr Ser Phe Pro Gln Gln His Thr
55                  60                  65 atg cag cac tgg gcc cgg cgt ctg gag cag gag gtc gac ggc gtg atg       416
Met Gln His Trp Ala Arg Arg Leu Glu Gln Glu Val Asp Gly Val Met
70                  75                  80                  85 cgg att ttt gga ggc gtc cag cag ctc cgt gag att tac aag gac aac       464
Arg Ile Phe Gly Gly Val Gln Gln Leu Arg Glu Ile Tyr Lys Asp Asn
                90                  95                 100 cgg aac ctg ttc gag gta cag gag aat gag cct cag aag ttg gtg gag       512
Arg Asn Leu Phe Glu Val Gln Glu Asn Glu Pro Gln Lys Leu Val Glu
            105                 110                 115 aag gtg gca ggg gac att gag agc ctt ctg gac agg aag gtg cag gcc       560
Lys Val Ala Gly Asp Ile Glu Ser Leu Leu Asp Arg Lys Val Gln Ala
        120                 125                 130 ctg aag aga ctg gct gat gct gca gag aac ttc cag aaa gca cac cgc       608
Leu Lys Arg Leu Ala Asp Ala Ala Glu Asn Phe Gln Lys Ala His Arg
    135                 140                 145 tgg cag gac aac atc aag gag gaa gac atc gtg tac tat gac gcc aag       656
Trp Gln Asp Asn Ile Lys Glu Glu Asp Ile Val Tyr Tyr Asp Ala Lys
150                 155                 160                 165 gct gac gct gag ctg gac gac cct gag agt gag gat gtg gaa agg ggg       704
Ala Asp Ala Glu Leu Asp Asp Pro Glu Ser Glu Asp Val Glu Arg Gly
                170                 175                 180 tct aag gcc agc acc cta agg ctg gac ttc atc gag gac cca aac ttc       752
Ser Lys Ala Ser Thr Leu Arg Leu Asp Phe Ile Glu Asp Pro Asn Phe
```

-continued

|  |  | 185 |  |  |  | 190 |  |  |  | 195 |  |  |  |
|---|---|---|---|---|---|---|---|---|---|---|---|---|---|
| aag | aac | aag | gtc | aac | tat | tca | tac | gcg | gct | gta | cag | atc | cct acg gac | 800 |
| Lys | Asn | Lys | Val | Asn | Tyr | Ser | Tyr | Ala | Ala | Val | Gln | Ile | Pro Thr Asp | |
|  |  | 200 |  |  |  | 205 |  |  |  | 210 |  |  |  |

```
atc tac aaa ggc tcc act gtc atc ctc aat gag ctc aac tgg aca gag      848
Ile Tyr Lys Gly Ser Thr Val Ile Leu Asn Glu Leu Asn Trp Thr Glu
    215                 220                 225 gcc ctg gag aat gtg ttc atg gaa aac cgc aga caa gac ccc aca ctg      896
Ala Leu Glu Asn Val Phe Met Glu Asn Arg Arg Gln Asp Pro Thr Leu
230                 235                 240                 245 ctg tgg cag gtc ttc ggc agc gcc aca gga gtc act cgc tac tac ccg      944
Leu Trp Gln Val Phe Gly Ser Ala Thr Gly Val Thr Arg Tyr Tyr Pro
                250                 255                 260 gcc acc ccg tgg cga gcc ccc aag aag atc gac ctg tac gat gtc cga      992
Ala Thr Pro Trp Arg Ala Pro Lys Lys Ile Asp Leu Tyr Asp Val Arg
            265                 270                 275 agg aga ccc tgg tat atc cag ggg gcc tcg tca ccc aaa gac atg gtc     1040
Arg Arg Pro Trp Tyr Ile Gln Gly Ala Ser Ser Pro Lys Asp Met Val
        280                 285                 290 atc atc gtg gat gtg agt ggc agt gtg agc ggc ctg acc ctg aag ctg     1088
Ile Ile Val Asp Val Ser Gly Ser Val Ser Gly Leu Thr Leu Lys Leu
    295                 300                 305 atg aag aca tct gtc tgc gag atg ctg gac acg ctg tct gat gat gac     1136
Met Lys Thr Ser Val Cys Glu Met Leu Asp Thr Leu Ser Asp Asp Asp
310                 315                 320                 325 tat gtg aat gtg gcc tcg ttc aac gag aag gca cag cct gtg tca tgc     1184
Tyr Val Asn Val Ala Ser Phe Asn Glu Lys Ala Gln Pro Val Ser Cys
                330                 335                 340 ttc aca cac ctg gtg cag gcc aat gtg cgc aac aag aag gtg ttc aag     1232
Phe Thr His Leu Val Gln Ala Asn Val Arg Asn Lys Lys Val Phe Lys
            345                 350                 355 gaa gct gtg cag ggc atg gtg gcc aag ggc acc aca ggc tac aag gcc     1280
Glu Ala Val Gln Gly Met Val Ala Lys Gly Thr Thr Gly Tyr Lys Ala
        360                 365                 370 ggc ttt gag tat gcc ttt gac cag ctg cag aac tcc aac atc act cgg     1328
Gly Phe Glu Tyr Ala Phe Asp Gln Leu Gln Asn Ser Asn Ile Thr Arg
    375                 380                 385 gcc aac tgc aac aag atg atc atg atg ttc acg gat ggt ggt gag gac     1376
Ala Asn Cys Asn Lys Met Ile Met Met Phe Thr Asp Gly Gly Glu Asp
390                 395                 400                 405 cgc gtg cag gac gtc ttt gag aag tac aat tgg cca aac cgg acg gtg     1424
Arg Val Gln Asp Val Phe Glu Lys Tyr Asn Trp Pro Asn Arg Thr Val
                410                 415                 420 cgc gtg ttt act ttc tcc gtg ggg cag cat aac tat gac gtc aca ccg     1472
Arg Val Phe Thr Phe Ser Val Gly Gln His Asn Tyr Asp Val Thr Pro
            425                 430                 435 ctg cag tgg atg gcc tgt gcc aac aaa ggc tac tat ttt gag atc cct     1520
Leu Gln Trp Met Ala Cys Ala Asn Lys Gly Tyr Tyr Phe Glu Ile Pro
        440                 445                 450 tcc atc gga gcc atc cgc atc aac aca cag gaa tat cta gat gtg ttg     1568
Ser Ile Gly Ala Ile Arg Ile Asn Thr Gln Glu Tyr Leu Asp Val Leu
    455                 460                 465 ggc agg ccc atg gtg ctg gca ggc aag gag gcc aag cag gtt cag tgg     1616
Gly Arg Pro Met Val Leu Ala Gly Lys Glu Ala Lys Gln Val Gln Trp
470                 475                 480                 485 acc aac gtg tat gag gat gca ctg gga ctg ggg ttg gtg gta aca ggg     1664
Thr Asn Val Tyr Glu Asp Ala Leu Gly Leu Gly Leu Val Val Thr Gly
                490                 495                 500 acc ctc cct gtt ttc aac ctg aca cag gat ggc cct ggg gaa aag aag     1712
```

```
                Thr Leu Pro Val Phe Asn Leu Thr Gln Asp Gly Pro Gly Glu Lys Lys
                                505                 510                 515 aac cag ctg atc ctg ggc gtg atg ggc att gac gtg gct ctg aat gac                1760
Asn Gln Leu Ile Leu Gly Val Met Gly Ile Asp Val Ala Leu Asn Asp
        520                 525                 530 atc aag agg ctg acc ccc aac tac acg ctt gga gcc aac ggc tat gtg                1808
Ile Lys Arg Leu Thr Pro Asn Tyr Thr Leu Gly Ala Asn Gly Tyr Val
535                 540                 545 ttt gcc att gac ctg aac ggc tac gtg ttg ctg cac ccc aat ctc aag                1856
Phe Ala Ile Asp Leu Asn Gly Tyr Val Leu Leu His Pro Asn Leu Lys
550                 555                 560                 565 ccc cag acc acc aac ttc cgg gag cct gtg act ctg gac ttc ctg gat                1904
Pro Gln Thr Thr Asn Phe Arg Glu Pro Val Thr Leu Asp Phe Leu Asp
                570                 575                 580 gcg gag cta gag gat gag aac aag gaa gag atc cgt cgg agc atg att                1952
Ala Glu Leu Glu Asp Glu Asn Lys Glu Glu Ile Arg Arg Ser Met Ile
            585                 590                 595 gat ggc aac aag ggc cac aag cag atc aga acg ttg gtc aag tcc ctg                2000
Asp Gly Asn Lys Gly His Lys Gln Ile Arg Thr Leu Val Lys Ser Leu
            600                 605                 610 gat gag agg tac ata gat gag gtg aca cgg aac tac acc tgg gtg cct                2048
Asp Glu Arg Tyr Ile Asp Glu Val Thr Arg Asn Tyr Thr Trp Val Pro
            615                 620                 625 ata agg agc act aac tac agc ctg ggg ctg gtg ctc cca ccc tac agc                2096
Ile Arg Ser Thr Asn Tyr Ser Leu Gly Leu Val Leu Pro Pro Tyr Ser
630                 635                 640                 645 acc ttc tac ctc caa gcc aat ctc agt gac cag atc ctg cag gtc aag                2144
Thr Phe Tyr Leu Gln Ala Asn Leu Ser Asp Gln Ile Leu Gln Val Lys
                650                 655                 660 tat ttt gag ttc ctg ctc ccc agc agc ttt gag tct gaa gga cac gtt                2192
Tyr Phe Glu Phe Leu Leu Pro Ser Ser Phe Glu Ser Glu Gly His Val
            665                 670                 675 ttc att gct ccc aga gag tac tgc aag gac ctg aat gcc tca gac aac                2240
Phe Ile Ala Pro Arg Glu Tyr Cys Lys Asp Leu Asn Ala Ser Asp Asn
            680                 685                 690 aac acc gag ttc ctg aaa aac ttt att gag ctc atg gag aaa gtg act                2288
Asn Thr Glu Phe Leu Lys Asn Phe Ile Glu Leu Met Glu Lys Val Thr
            695                 700                 705 cca gac tcc aag cag tgc aac aac ttc ctt ctg cac aac ctg atc ttg                2336
Pro Asp Ser Lys Gln Cys Asn Asn Phe Leu Leu His Asn Leu Ile Leu
710                 715                 720                 725 gac acg ggc atc acg cag cag ctg gta gag cgt gtg tgg agg gac cag                2384
Asp Thr Gly Ile Thr Gln Gln Leu Val Glu Arg Val Trp Arg Asp Gln
                730                 735                 740 gat ctc aac acg tac agc cta ctg gcc gtg ttc gct gcc aca gac ggt                2432
Asp Leu Asn Thr Tyr Ser Leu Leu Ala Val Phe Ala Ala Thr Asp Gly
                745                 750                 755 ggc atc acc cga gtc ttc ccc aac aag gca gct gag gac tgg aca gag                2480
Gly Ile Thr Arg Val Phe Pro Asn Lys Ala Ala Glu Asp Trp Thr Glu
            760                 765                 770 aac cct gag ccc ttc aat gcc agc ttc tac cgc cgc agc ctg gat aac                2528
Asn Pro Glu Pro Phe Asn Ala Ser Phe Tyr Arg Arg Ser Leu Asp Asn
775                 780                 785 cac ggt tat gtc ttc aag ccc cca cac cag gat gcc ctg tta agg ccg                2576
His Gly Tyr Val Phe Lys Pro Pro His Gln Asp Ala Leu Leu Arg Pro
790                 795                 800                 805 ctg gag ctg gag aat gac act gtg ggc atc ctc gtc agc aca gct gtg                2624
Leu Glu Leu Glu Asn Asp Thr Val Gly Ile Leu Val Ser Thr Ala Val
                810                 815                 820
```

-continued

| | |
|---|---|
| gag ctc agc cta ggc agg cgc aca ctg agg cca gca gtg gtg ggc gtc<br>Glu Leu Ser Leu Gly Arg Arg Thr Leu Arg Pro Ala Val Val Gly Val<br>825                     830                    835 | 2672 |
| aag ctg gac cta gag gct tgg gct gag aag ttc aag gtg cta gcc agc<br>Lys Leu Asp Leu Glu Ala Trp Ala Glu Lys Phe Lys Val Leu Ala Ser<br>840                     845                    850 | 2720 |
| aac cgt acc cac caa gac cag cct cag aag tgc ggc ccc aac agc cac<br>Asn Arg Thr His Gln Asp Gln Pro Gln Lys Cys Gly Pro Asn Ser His<br>   855                    860                    865 | 2768 |
| tgt gag atg gac tgc gag gtt aac aat gag gac tta ctc tgt gtc ctc<br>Cys Glu Met Asp Cys Glu Val Asn Asn Glu Asp Leu Leu Cys Val Leu<br>870                     875                    880                    885 | 2816 |
| att gat gat gga gga ttc ctg gtg ctg tca aac cag aac cat cag tgg<br>Ile Asp Asp Gly Gly Phe Leu Val Leu Ser Asn Gln Asn His Gln Trp<br>                  890                    895                    900 | 2864 |
| gac cag gtg ggc agg ttc ttc agt gag gtg gat gcc aac ctg atg ctg<br>Asp Gln Val Gly Arg Phe Phe Ser Glu Val Asp Ala Asn Leu Met Leu<br>905                     910                    915 | 2912 |
| gca ctc tac aat aac tcc ttc tac acc cgc aag gag tcc tat gac tat<br>Ala Leu Tyr Asn Asn Ser Phe Tyr Thr Arg Lys Glu Ser Tyr Asp Tyr<br>920                     925                    930 | 2960 |
| cag gca gcc tgt gcc cct cag ccc cct ggc aac ctg ggt gct gca ccc<br>Gln Ala Ala Cys Ala Pro Gln Pro Pro Gly Asn Leu Gly Ala Ala Pro<br>935                     940                    945 | 3008 |
| cgg ggt gtc ttt gtg ccc acc gtt gca gat ttc ctt aac ctg gcc tgg<br>Arg Gly Val Phe Val Pro Thr Val Ala Asp Phe Leu Asn Leu Ala Trp<br>950                     955                    960                    965 | 3056 |
| tgg acc tct gct gcc gcc tgg tcc ctg ttc cag cag ctt ctc tac ggc<br>Trp Thr Ser Ala Ala Ala Trp Ser Leu Phe Gln Gln Leu Leu Tyr Gly<br>                  970                    975                    980 | 3104 |
| ctc atc tac cac agc tgg ttc caa gca gac ccc gcg gag gcc gag ggg<br>Leu Ile Tyr His Ser Trp Phe Gln Ala Asp Pro Ala Glu Ala Glu Gly<br>   985                    990                    995 | 3152 |
| agc ccc gag acg cgc gag agc agc tgc gtc atg aaa cag acc cag tac<br>Ser Pro Glu Thr Arg Glu Ser Ser Cys Val Met Lys Gln Thr Gln Tyr<br>1000                   1005                1010 | 3200 |
| tac ttc ggc tcg gta aac gcc tcc tac aac gcc atc atc gac tgc gga<br>Tyr Phe Gly Ser Val Asn Ala Ser Tyr Asn Ala Ile Ile Asp Cys Gly<br>   1015                   1020                1025 | 3248 |
| aac tgc tcc agg ctg ttc cac gcg cag aga ctg acc aac acc aat ctt<br>Asn Cys Ser Arg Leu Phe His Ala Gln Arg Leu Thr Asn Thr Asn Leu<br>1030                   1035                1040                1045 | 3296 |
| ctc ttt gtg gtg gcc gag aag ccg ctg tgc agc cag tgc gag gct ggc<br>Leu Phe Val Val Ala Glu Lys Pro Leu Cys Ser Gln Cys Glu Ala Gly<br>                  1050                1055                1060 | 3344 |
| cgg ctg ctg cag aag gag acg cac tgc cca gcg gac ggc ccg gag cag<br>Arg Leu Leu Gln Lys Glu Thr His Cys Pro Ala Asp Gly Pro Glu Gln<br>           1065                1070                1075 | 3392 |
| tgt gag cta gtg cag aga ccg cga tac cgg aga ggc ccg cac atc tgc<br>Cys Glu Leu Val Gln Arg Pro Arg Tyr Arg Arg Gly Pro His Ile Cys<br>1080                   1085                1090 | 3440 |
| ttc gac tac aac gcg aca gaa gat acc tca gac tgt ggc cgc ggg gcc<br>Phe Asp Tyr Asn Ala Thr Glu Asp Thr Ser Asp Cys Gly Arg Gly Ala<br>   1095                   1100                1105 | 3488 |
| tcc ttc ccg ccg tcg ctg ggc gtc ctg gtc tcc ctg caa ctg ctg ctc<br>Ser Phe Pro Pro Ser Leu Gly Val Leu Val Ser Leu Gln Leu Leu Leu<br>1110                   1115                1120                1125 | 3536 |
| ctc ctg ggc ctg ccg ccc cgg ccg cag cct caa gtc ctc gtc cac gcc<br>Leu Leu Gly Leu Pro Pro Arg Pro Gln Pro Gln Val Leu Val His Ala<br>           1130                1135                1140 | 3584 |

```
tct cgc cgc ctc tga gcacctgcc ccacccacc tccactccca cctcacccgg      3639
Ser Arg Arg Leu
        1145 cctcttcgcc tttcccaccc tcctgcccca cactcccgc cttagagcct cgtccctccc   3699 tcactgaagg acctgagctg gccaggccct gagagtctgg tctgcgcctt gggatgggga   3759 gtcccaaagc gggacgccgc aggtgtttgg cacccaaatc acatctcacc tccgaactgt   3819 tcaagtgtcc ccagacccctt cttgcctgct gggctccccc cagtgggatg ggacagggag  3879 gccacacgca ctggtgccaa accaggcct ctgctgccgc ccttcctgga ggctgcctat    3939 gttgggggg accctgcctc agctgacccg gcctctctgc cccacccaag cccaaacttg    3999 gtttctgtga aatagtgga ggaaggtgag atggccagtt tgaagcctgt gcctcccagc    4059 ttaaatccta gcaggagaga ggctctgggg cagccccccat gggctcctgc ccctttcagg  4119 cctacagcca catccccaag cccaccaggt gtcaggatag tcacagtgat accagttcag   4179 acactacccc atatacacct ggaacattga ggatggaaac tggactcaca ttcgacatac   4239 cccactgggc acacgcacaa acacacacac tatgggtgg gtgggtgta ggggcttaca    4299 aagccttaca cagggcgagg ggttggtggg agggttggca cctgcacact ccatctcctg   4359 ctcaccacct gcctctaatc tgagctgcag cctggctggt cctcccatttt ctaaagctga  4419 atgtcaaaca gtgccaaatg ctggggcagg gggtgaagaa ccctctgtcc caccctagc    4479 caccagtgtc ctccaagtgc cccctcacct tccaggtgc tcattgtaac catttctcac    4539 tagtgtcagg cccccagtgg gaccacatgc cactgcctgc acctttcggc agaggaaccc   4599 ccaccagaca tcacccttg cctttagcagg ggtgactttg tctctcctgg ctgggccatc   4659 cttccgccaa tctgggccctt acacactcag gcctgtgccc actccctatc tccttcccac  4719 ccctacacac acactcctg cttgcaggag gccaaactgt cctccctg ctgaacacac      4779 acacacacac acacacacag gtggggactg gcacagctc ttcacaccat tcattctggt    4839 catttccccc aaaggcatcc cagcctgggg gccagtgggg aactgagggc aaggggatat   4899 agtgatgggg ctcagatgga ctgggaggag ggaggggtg atgcattaat taatggcttc    4959 gttaattaat gtcatgttgc ttgtcgcttt ctcagtgtgt gtgtgtggtc catgcccact   5019 gctggtgcca gggtgggtgt ccatgtgcac ccggcctgga tgccagctgt gtccttcggg   5079 ggcgtgcgtg taactgtagt gtagtcaggt gctcaatgga gaatataaac atatacagaa   5139 aaatatatat tttaagttta aaaacagaa aaacagacaa acaatcccc atcaggtagc     5199 tgtctaaccc ccagctgggt ctaatccttc tcattaccca cccgacctgg ctgcccctca   5259 ccttgggctg ggggactggg gggccatttc cttttctctg cccttttttt gttgttctat   5319 tttgtacaga caagttggaa aaacaacagc gacaaaaaag tcaagaaact ttgtaaaata   5379 tcgtgtgtgt gattccttgt aaaatatttt caaatggttt attacagaag atcagttatt   5439 aaataatgtt catattttca cttc                                          5463

<210> SEQ ID NO 2
<211> LENGTH: 1145
<212> TYPE: PRT
<213> ORGANISM: Homo sapiens

<400> SEQUENCE: 2

Met Ala Val Pro Ala Arg Thr Cys Gly Ala Ser Arg Pro Gly Pro Ala
 1               5                  10                  15

Arg Thr Ala Arg Pro Trp Pro Gly Cys Gly Pro His Pro Gly Pro Gly
```

```
            20                  25                  30
Thr Arg Arg Pro Thr Ser Gly Pro Pro Arg Pro Leu Trp Leu Leu Leu
             35                  40                  45

Pro Leu Leu Pro Leu Leu Ala Ala Pro Gly Ala Ser Ala Tyr Ser Phe
 50                  55                  60

Pro Gln Gln His Thr Met Gln His Trp Ala Arg Arg Leu Gln Gln Glu
 65                  70                  75                  80

Val Asp Gly Val Met Arg Ile Phe Gly Gly Val Gln Gln Leu Arg Glu
                 85                  90                  95

Ile Tyr Lys Asp Asn Arg Asn Leu Phe Glu Val Gln Glu Asn Glu Pro
             100                 105                 110

Gln Lys Leu Val Glu Lys Val Ala Gly Asp Ile Glu Ser Leu Leu Asp
         115                 120                 125

Arg Lys Val Gln Ala Leu Lys Arg Leu Ala Asp Ala Ala Glu Asn Phe
     130                 135                 140

Gln Lys Ala His Arg Trp Gln Asp Asn Ile Lys Glu Glu Asp Ile Val
145                 150                 155                 160

Tyr Tyr Asp Ala Lys Ala Asp Ala Glu Leu Asp Asp Pro Glu Ser Glu
                 165                 170                 175

Asp Val Glu Arg Gly Ser Lys Ala Ser Thr Leu Arg Leu Asp Phe Ile
             180                 185                 190

Glu Asp Pro Asn Phe Lys Asn Lys Val Asn Tyr Ser Tyr Ala Ala Val
         195                 200                 205

Gln Ile Pro Thr Asp Ile Tyr Lys Gly Ser Thr Val Ile Leu Asn Glu
     210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
                 245                 250                 255

Thr Arg Tyr Tyr Pro Ala Thr Pro Trp Arg Ala Pro Lys Lys Ile Asp
             260                 265                 270

Leu Tyr Asp Val Arg Arg Arg Pro Trp Tyr Ile Gln Gly Ala Ser Ser
         275                 280                 285

Pro Lys Asp Met Val Ile Ile Val Asp Val Ser Gly Ser Val Ser Gly
     290                 295                 300

Leu Thr Leu Lys Leu Met Lys Thr Ser Val Cys Glu Met Leu Asp Thr
305                 310                 315                 320

Leu Ser Asp Asp Asp Tyr Val Asn Val Ala Ser Phe Asn Glu Lys Ala
                 325                 330                 335

Gln Pro Val Ser Cys Phe Thr His Leu Val Gln Ala Asn Val Arg Asn
             340                 345                 350

Lys Lys Val Phe Lys Glu Ala Val Gln Gly Met Val Ala Lys Gly Thr
         355                 360                 365

Thr Gly Tyr Lys Ala Gly Phe Glu Tyr Ala Phe Asp Gln Leu Gln Asn
     370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                 405                 410                 415

Pro Asn Arg Thr Val Arg Val Phe Thr Phe Ser Val Gly Gln His Asn
             420                 425                 430

Tyr Asp Val Thr Pro Leu Gln Trp Met Ala Cys Ala Asn Lys Gly Tyr
         435                 440                 445
```

```
Tyr Phe Glu Ile Pro Ser Ile Gly Ala Ile Arg Ile Asn Thr Gln Glu
    450                 455                 460

Tyr Leu Asp Val Leu Gly Arg Pro Met Val Leu Ala Gly Lys Glu Ala
465                 470                 475                 480

Lys Gln Val Gln Trp Thr Asn Val Tyr Glu Asp Ala Leu Gly Leu Gly
                485                 490                 495

Leu Val Val Thr Gly Thr Leu Pro Val Phe Asn Leu Thr Gln Asp Gly
                500                 505                 510

Pro Gly Glu Lys Lys Asn Gln Leu Ile Leu Gly Val Met Gly Ile Asp
            515                 520                 525

Val Ala Leu Asn Asp Ile Lys Arg Leu Thr Pro Asn Tyr Thr Leu Gly
530                 535                 540

Ala Asn Gly Tyr Val Phe Ala Ile Asp Leu Asn Gly Tyr Val Leu Leu
545                 550                 555                 560

His Pro Asn Leu Lys Pro Gln Thr Thr Asn Phe Arg Glu Pro Val Thr
                565                 570                 575

Leu Asp Phe Leu Asp Ala Glu Leu Glu Asp Glu Asn Lys Glu Glu Ile
                580                 585                 590

Arg Arg Ser Met Ile Asp Gly Asn Lys Gly His Lys Gln Ile Arg Thr
                595                 600                 605

Leu Val Lys Ser Leu Asp Glu Arg Tyr Ile Asp Glu Val Thr Arg Asn
610                 615                 620

Tyr Thr Trp Val Pro Ile Arg Ser Thr Asn Tyr Ser Leu Gly Leu Val
625                 630                 635                 640

Leu Pro Pro Tyr Ser Thr Phe Tyr Leu Gln Ala Asn Leu Ser Asp Gln
                645                 650                 655

Ile Leu Gln Val Lys Tyr Phe Glu Phe Leu Leu Pro Ser Ser Phe Glu
                660                 665                 670

Ser Glu Gly His Val Phe Ile Ala Pro Arg Glu Tyr Cys Lys Asp Leu
                675                 680                 685

Asn Ala Ser Asp Asn Asn Thr Glu Phe Leu Lys Asn Phe Ile Glu Leu
                690                 695                 700

Met Glu Lys Val Thr Pro Asp Ser Lys Gln Cys Asn Asn Phe Leu Leu
705                 710                 715                 720

His Asn Leu Ile Leu Asp Thr Gly Ile Thr Gln Gln Leu Val Glu Arg
                725                 730                 735

Val Trp Arg Asp Gln Asp Leu Asn Thr Tyr Ser Leu Leu Ala Val Phe
                740                 745                 750

Ala Ala Thr Asp Gly Gly Ile Thr Arg Val Phe Pro Asn Lys Ala Ala
                755                 760                 765

Glu Asp Trp Thr Glu Asn Pro Glu Pro Phe Asn Ala Ser Phe Tyr Arg
770                 775                 780

Arg Ser Leu Asp Asn His Gly Tyr Val Phe Lys Pro Pro His Gln Asp
785                 790                 795                 800

Ala Leu Leu Arg Pro Leu Glu Leu Glu Asn Asp Thr Val Gly Ile Leu
                805                 810                 815

Val Ser Thr Ala Val Glu Leu Ser Leu Gly Arg Arg Thr Leu Arg Pro
                820                 825                 830

Ala Val Val Gly Val Lys Leu Asp Leu Glu Ala Trp Ala Glu Lys Phe
                835                 840                 845

Lys Val Leu Ala Ser Asn Arg Thr His Gln Asp Gln Pro Gln Lys Cys
850                 855                 860
```

-continued

```
Gly Pro Asn Ser His Cys Glu Met Asp Cys Glu Val Asn Asn Glu Asp
865                 870                 875                 880

Leu Leu Cys Val Leu Ile Asp Asp Gly Gly Phe Leu Val Leu Ser Asn
                885                 890                 895

Gln Asn His Gln Trp Asp Gln Val Gly Arg Phe Phe Ser Glu Val Asp
            900                 905                 910

Ala Asn Leu Met Leu Ala Leu Tyr Asn Asn Ser Phe Tyr Thr Arg Lys
        915                 920                 925

Glu Ser Tyr Asp Tyr Gln Ala Ala Cys Ala Pro Gln Pro Pro Gly Asn
    930                 935                 940

Leu Gly Ala Ala Pro Arg Gly Val Phe Val Pro Thr Val Ala Asp Phe
945                 950                 955                 960

Leu Asn Leu Ala Trp Trp Thr Ser Ala Ala Trp Ser Leu Phe Gln
                965                 970                 975

Gln Leu Leu Tyr Gly Leu Ile Tyr His Ser Trp Phe Gln Ala Asp Pro
            980                 985                 990

Ala Glu Ala Glu Gly Ser Pro Glu Thr Arg Glu Ser Ser Cys Val Met
        995                 1000                1005

Lys Gln Thr Gln Tyr Tyr Phe Gly Ser Val Asn Ala Ser Tyr Asn Ala
    1010                1015                1020

Ile Ile Asp Cys Gly Asn Cys Ser Arg Leu Phe His Ala Gln Arg Leu
1025                1030                1035                1040

Thr Asn Thr Asn Leu Leu Phe Val Val Ala Glu Lys Pro Leu Cys Ser
                1045                1050                1055

Gln Cys Glu Ala Gly Arg Leu Leu Gln Lys Glu Thr His Cys Pro Ala
            1060                1065                1070

Asp Gly Pro Glu Gln Cys Glu Leu Val Gln Arg Pro Arg Tyr Arg Arg
        1075                1080                1085

Gly Pro His Ile Cys Phe Asp Tyr Asn Ala Thr Glu Asp Thr Ser Asp
    1090                1095                1100

Cys Gly Arg Gly Ala Ser Phe Pro Pro Ser Leu Gly Val Leu Val Ser
1105                1110                1115                1120

Leu Gln Leu Leu Leu Leu Leu Gly Leu Pro Arg Pro Gln Pro Gln
                1125                1130                1135

Val Leu Val His Ala Ser Arg Arg Leu
            1140                1145

<210> SEQ ID NO 3
<211> LENGTH: 5482
<212> TYPE: DNA
<213> ORGANISM: Homo sapiens
<220> FEATURE:
<221> NAME/KEY: CDS
<222> LOCATION: (181)..(3618)

<400> SEQUENCE: 3
cgggcagcgc agcccgcaga ggcgctgcgg cccgtgcagc cccggaggcc cctcgcggag    60
aaggcggcgg cggaggagag gccgagttac cgcccgccgc ccgcgccccc ccaacccccgc  120 cgccgccgcc gccgccgcca ctgcccccccc tcccgcggc gccgcatctt gaatggaaac   180 atg gcg gtg ccg gct cgg acc tgc ggc gcc tct cgg ccc ggc cca gcg    228
Met Ala Val Pro Ala Arg Thr Cys Gly Ala Ser Arg Pro Gly Pro Ala
  1               5                  10                  15 cgg act gcg cgc ccc tgg ccc ggc tgc ggc ccc cac cct ggc ccc ggc    276
Arg Thr Ala Arg Pro Trp Pro Gly Cys Gly Pro His Pro Gly Pro Gly
             20                  25                  30
```

```
acc cgg cgc ccg acg tcc ggg ccc ccg cgc ccg ctg tgg ctg ctg ctg          324
Thr Arg Arg Pro Thr Ser Gly Pro Pro Arg Pro Leu Trp Leu Leu Leu
         35                  40                  45 ccg ctt cta ccg ctg ctc gcc gcc ccc ggc gcc tct gcc tac agc ttc          372
Pro Leu Leu Pro Leu Leu Ala Ala Pro Gly Ala Ser Ala Tyr Ser Phe
 50                  55                  60 ccc cag cag cac acg atg cag cac tgg gcc cgg cgt ctg gag cag gag          420
Pro Gln Gln His Thr Met Gln His Trp Ala Arg Arg Leu Glu Gln Glu
 65                  70                  75                  80 gtc gac ggc gtg atg cgg att ttt gga ggc gtc cag cag ctc cgt gag          468
Val Asp Gly Val Met Arg Ile Phe Gly Gly Val Gln Gln Leu Arg Glu
                 85                  90                  95 att tac aag gac aac cgg aac ctg ttc gag gta cag gag aat gag cct          516
Ile Tyr Lys Asp Asn Arg Asn Leu Phe Glu Val Gln Glu Asn Glu Pro
            100                 105                 110 cag aag ttg gtg gag aag gtg gca ggg gac att gag agc ctt ctg gac          564
Gln Lys Leu Val Glu Lys Val Ala Gly Asp Ile Glu Ser Leu Leu Asp
        115                 120                 125 agg aag gtg cag gcc ctg aag aga ctg gct gat gct gca gag aac ttc          612
Arg Lys Val Gln Ala Leu Lys Arg Leu Ala Asp Ala Ala Glu Asn Phe
130                 135                 140 cag aaa gca cac cgc tgg cag gac aac atc aag gag gaa gac atc gtg          660
Gln Lys Ala His Arg Trp Gln Asp Asn Ile Lys Glu Glu Asp Ile Val
145                 150                 155                 160 tac tat gac gcc aag gct gac gct gag ctg gac gac cct gag agt gag          708
Tyr Tyr Asp Ala Lys Ala Asp Ala Glu Leu Asp Asp Pro Glu Ser Glu
                165                 170                 175 gat gtg gaa agg ggg tct aag gcc agc acc cta agg ctg gac ttc atc          756
Asp Val Glu Arg Gly Ser Lys Ala Ser Thr Leu Arg Leu Asp Phe Ile
            180                 185                 190 gag gac cca aac ttc aag aac aag gtc aac tat tca tac gcg gct gta          804
Glu Asp Pro Asn Phe Lys Asn Lys Val Asn Tyr Ser Tyr Ala Ala Val
        195                 200                 205 cag atc cct acg gac atc tac aaa ggc tcc act gtc atc ctc aat gag          852
Gln Ile Pro Thr Asp Ile Tyr Lys Gly Ser Thr Val Ile Leu Asn Glu
    210                 215                 220 ctc aac tgg aca gag gcc ctg gag aat gtg ttc atg gaa aac cgc aga          900
Leu Asn Trp Thr Glu Ala Leu Glu Asn Val Phe Met Glu Asn Arg Arg
225                 230                 235                 240 caa gac ccc aca ctg ctg tgg cag gtc ttc ggc agc gcc aca gga gtc          948
Gln Asp Pro Thr Leu Leu Trp Gln Val Phe Gly Ser Ala Thr Gly Val
                245                 250                 255 act cgc tac tac ccg gcc acc ccg tgg cga gcc ccc aag aag atc gac          996
Thr Arg Tyr Tyr Pro Ala Thr Pro Trp Arg Ala Pro Lys Lys Ile Asp
            260                 265                 270 ctg tac gat gtc cga agg aga ccc tgg tat atc cag ggg gcc tcg tca         1044
Leu Tyr Asp Val Arg Arg Arg Pro Trp Tyr Ile Gln Gly Ala Ser Ser
        275                 280                 285 ccc aaa gac atg gtc atc atc gtg gat gtg agt ggc agt gtg agc ggc         1092
Pro Lys Asp Met Val Ile Ile Val Asp Val Ser Gly Ser Val Ser Gly
290                 295                 300 ctg acc ctg aag ctg atg aag aca tct gtc tgc gag atg ctg gac acg         1140
Leu Thr Leu Lys Leu Met Lys Thr Ser Val Cys Glu Met Leu Asp Thr
305                 310                 315                 320 ctg tct gat gat gac tat gtg aat gtg gcc tcg ttc aac gag aag gca         1188
Leu Ser Asp Asp Asp Tyr Val Asn Val Ala Ser Phe Asn Glu Lys Ala
                325                 330                 335 cag cct gtg tca tgc ttc aca cac ctg gtg cag gcc aat gtg cgc aac         1236
Gln Pro Val Ser Cys Phe Thr His Leu Val Gln Ala Asn Val Arg Asn
            340                 345                 350
```

```
aag aag gtg ttc aag gaa gct gtg cag ggc atg gtg gcc aag ggc acc    1284
Lys Lys Val Phe Lys Glu Ala Val Gln Gly Met Val Ala Lys Gly Thr
        355                 360                 365 aca ggc tac aag gcc ggc ttt gag tat gcc ttt gac cag ctg cag aac    1332
Thr Gly Tyr Lys Ala Gly Phe Glu Tyr Ala Phe Asp Gln Leu Gln Asn
    370                 375                 380 tcc aac atc act cgg gcc aac tgc aac aag atg atc atg atg ttc acg    1380
Ser Asn Ile Thr Arg Ala Asn Cys Asn Lys Met Ile Met Met Phe Thr
385                 390                 395                 400 gat ggt ggt gag gac cgc gtg cag gac gtc ttt gag aag tac aat tgg    1428
Asp Gly Gly Glu Asp Arg Val Gln Asp Val Phe Glu Lys Tyr Asn Trp
                405                 410                 415 cca aac cgg acg gtg cgc gtg ttt act ttc tcc gtg ggg cag cat aac    1476
Pro Asn Arg Thr Val Arg Val Phe Thr Phe Ser Val Gly Gln His Asn
            420                 425                 430 tat gac gtc aca ccg ctg cag tgg atg gcc tgt gcc aac aaa ggc tac    1524
Tyr Asp Val Thr Pro Leu Gln Trp Met Ala Cys Ala Asn Lys Gly Tyr
        435                 440                 445 tat ttt gag atc cct tcc atc gga gcc atc cgc atc aac aca cag gaa    1572
Tyr Phe Glu Ile Pro Ser Ile Gly Ala Ile Arg Ile Asn Thr Gln Glu
    450                 455                 460 tat cta gat gtg ttg ggc agg ccc atg gtg ctg gca ggc aag gag gcc    1620
Tyr Leu Asp Val Leu Gly Arg Pro Met Val Leu Ala Gly Lys Glu Ala
465                 470                 475                 480 aag cag gtt cag tgg acc aac gtg tat gag gat gca ctg gga ctg ggg    1668
Lys Gln Val Gln Trp Thr Asn Val Tyr Glu Asp Ala Leu Gly Leu Gly
                485                 490                 495 ttg gtg gta aca ggg acc ctc cct gtt ttc aac ctg aca cag gat ggc    1716
Leu Val Val Thr Gly Thr Leu Pro Val Phe Asn Leu Thr Gln Asp Gly
            500                 505                 510 cct ggg gaa aag aag aac cag ctg atc ctg ggc gtg atg ggc att gac    1764
Pro Gly Glu Lys Lys Asn Gln Leu Ile Leu Gly Val Met Gly Ile Asp
        515                 520                 525 gtg gct ctg aat gac atc aag agg ctg acc ccc aac tac acg ctt gga    1812
Val Ala Leu Asn Asp Ile Lys Arg Leu Thr Pro Asn Tyr Thr Leu Gly
    530                 535                 540 gcc aac ggc tat gtg ttt gcc att gac ctg aac ggc tac gtg ttg ctg    1860
Ala Asn Gly Tyr Val Phe Ala Ile Asp Leu Asn Gly Tyr Val Leu Leu
545                 550                 555                 560 cac ccc aat ctc aag ccc cag acc acc aac ttc cgg gag cct gtg act    1908
His Pro Asn Leu Lys Pro Gln Thr Thr Asn Phe Arg Glu Pro Val Thr
                565                 570                 575 ctg gac ttc ctg gat gcg gag cta gag gat gag aac aag gaa gag atc    1956
Leu Asp Phe Leu Asp Ala Glu Leu Glu Asp Glu Asn Lys Glu Glu Ile
            580                 585                 590 cgt cgg agc atg att gat ggc aac aag ggc cac aag cag atc aga acg    2004
Arg Arg Ser Met Ile Asp Gly Asn Lys Gly His Lys Gln Ile Arg Thr
        595                 600                 605 ttg gtc aag tcc ctg gat gag agg tac ata gat gag gtg aca cgg aac    2052
Leu Val Lys Ser Leu Asp Glu Arg Tyr Ile Asp Glu Val Thr Arg Asn
    610                 615                 620 tac acc tgg gtg cct ata agg agc act aac tac agc ctg ggg ctg gtg    2100
Tyr Thr Trp Val Pro Ile Arg Ser Thr Asn Tyr Ser Leu Gly Leu Val
625                 630                 635                 640 ctc cca ccc tac agc acc ttc tac ctc caa gcc aat ctc agt gac cag    2148
Leu Pro Pro Tyr Ser Thr Phe Tyr Leu Gln Ala Asn Leu Ser Asp Gln
                645                 650                 655 atc ctg cag gtc aag tat ttt gag ttc ctg ctc ccc agc agc ttt gag    2196
Ile Leu Gln Val Lys Tyr Phe Glu Phe Leu Leu Pro Ser Ser Phe Glu
```

-continued

```
              660                     665                     670
tct gaa gga cac gtt ttc att gct ccc aga gag tac tgc aag gac ctg      2244
Ser Glu Gly His Val Phe Ile Ala Pro Arg Glu Tyr Cys Lys Asp Leu
            675                 680                 685 aat gcc tca gac aac aac acc gag ttc ctg aaa aac ttt att gag ctc      2292
Asn Ala Ser Asp Asn Asn Thr Glu Phe Leu Lys Asn Phe Ile Glu Leu
        690                 695                 700 atg gag aaa gtg act cca gac tcc aag cag tgc aac aac ttc ctt ctg      2340
Met Glu Lys Val Thr Pro Asp Ser Lys Gln Cys Asn Asn Phe Leu Leu
705                 710                 715                 720 cac aac ctg atc ttg gac acg ggc atc acg cag cag ctg gta gag cgt      2388
His Asn Leu Ile Leu Asp Thr Gly Ile Thr Gln Gln Leu Val Glu Arg
                725                 730                 735 gtg tgg agg gac cag gat ctc aac acg tac agc cta ctg gcc gtg ttc      2436
Val Trp Arg Asp Gln Asp Leu Asn Thr Tyr Ser Leu Leu Ala Val Phe
            740                 745                 750 gct gcc aca gac ggt ggc atc acc cga gtc ttc ccc aac aag gca gct      2484
Ala Ala Thr Asp Gly Gly Ile Thr Arg Val Phe Pro Asn Lys Ala Ala
        755                 760                 765 gag gac tgg aca gag aac cct gag ccc ttc aat gcc agc ttc tac cgc      2532
Glu Asp Trp Thr Glu Asn Pro Glu Pro Phe Asn Ala Ser Phe Tyr Arg
    770                 775                 780 cgc agc ctg gat aac cac ggt tat gtc ttc aag ccc cca cac cag gat      2580
Arg Ser Leu Asp Asn His Gly Tyr Val Phe Lys Pro Pro His Gln Asp
785                 790                 795                 800 gcc ctg tta agg ccg ctg gag ctg gag aat gac act gtg ggc atc ctc      2628
Ala Leu Leu Arg Pro Leu Glu Leu Glu Asn Asp Thr Val Gly Ile Leu
                805                 810                 815 gtc agc aca gct gtg gag ctc agc cta ggc agg cgc aca ctg agg cca      2676
Val Ser Thr Ala Val Glu Leu Ser Leu Gly Arg Arg Thr Leu Arg Pro
            820                 825                 830 gca gtg gtg ggc gtc aag ctg gac cta gag gct tgg gct gag aag ttc      2724
Ala Val Val Gly Val Lys Leu Asp Leu Glu Ala Trp Ala Glu Lys Phe
        835                 840                 845 aag gtg cta gcc agc aac cgt acc cac caa gac cag cct cag aag tgc      2772
Lys Val Leu Ala Ser Asn Arg Thr His Gln Asp Gln Pro Gln Lys Cys
    850                 855                 860 ggc ccc aac agc cac tgt gag atg gac tgc gag gtt aac aat gag gac      2820
Gly Pro Asn Ser His Cys Glu Met Asp Cys Glu Val Asn Asn Glu Asp
865                 870                 875                 880 tta ctc tgt gtc ctc att gat gat gga gga ttc ctg gtg ctg tca aac      2868
Leu Leu Cys Val Leu Ile Asp Asp Gly Gly Phe Leu Val Leu Ser Asn
                885                 890                 895 cag aac cat cag tgg gac cag gtg ggc agg ttc ttc agt gag gtg gat      2916
Gln Asn His Gln Trp Asp Gln Val Gly Arg Phe Phe Ser Glu Val Asp
            900                 905                 910 gcc aac ctg atg ctg gca ctc tac aat aac tcc ttc tac acc cgc aag      2964
Ala Asn Leu Met Leu Ala Leu Tyr Asn Asn Ser Phe Tyr Thr Arg Lys
        915                 920                 925 gag tcc tat gac tat cag gca gcc tgt gcc cct cag ccc cct ggc aac      3012
Glu Ser Tyr Asp Tyr Gln Ala Ala Cys Ala Pro Gln Pro Pro Gly Asn
    930                 935                 940 ctg ggt gct gca ccc cgg ggt gtc ttt gtg ccc acc gtt gca gat ttc      3060
Leu Gly Ala Ala Pro Arg Gly Val Phe Val Pro Thr Val Ala Asp Phe
945                 950                 955                 960 ctt aac ctg gcc tgg tgg acc tct gct gcc gcc tgg tcc ctg ttc cag      3108
Leu Asn Leu Ala Trp Trp Thr Ser Ala Ala Ala Trp Ser Leu Phe Gln
                965                 970                 975 cag ctt ctc tac ggc ctc atc tac cac agc tgg ttc caa gca gac ccc      3156
```

```
                                                              -continued

Gln Leu Leu Tyr Gly Leu Ile Tyr His Ser Trp Phe Gln Ala Asp Pro
            980                 985                 990 gcg gag gcc gag ggg agc ccc gag acg cgc gag agc agc tgc gtc atg      3204
Ala Glu Ala Glu Gly Ser Pro Glu Thr Arg Glu Ser Ser Cys Val Met
        995                 1000                1005 aaa cag acc cag tac tac ttc ggc tcg gta aac gcc tcc tac aac gcc      3252
Lys Gln Thr Gln Tyr Tyr Phe Gly Ser Val Asn Ala Ser Tyr Asn Ala
    1010                1015                1020 atc atc gac tgc gga aac tgc tcc agg ctg ttc cac gcg cag aga ctg      3300
Ile Ile Asp Cys Gly Asn Cys Ser Arg Leu Phe His Ala Gln Arg Leu
1025                1030                1035                1040 acc aac acc aat ctt ctc ttt gtg gtg gcc gag aag ccg ctg tgc agc      3348
Thr Asn Thr Asn Leu Leu Phe Val Val Ala Glu Lys Pro Leu Cys Ser
                1045                1050                1055 cag tgc gag gct ggc cgg ctg ctg cag aag gag acg cac tgc cca gcg      3396
Gln Cys Glu Ala Gly Arg Leu Leu Gln Lys Glu Thr His Cys Pro Ala
            1060                1065                1070 gac ggc ccg gag cag tgt gag cta gtg cag aga ccg cga tac cgg aga      3444
Asp Gly Pro Glu Gln Cys Glu Leu Val Gln Arg Pro Arg Tyr Arg Arg
        1075                1080                1085 ggc ccg cac atc tgc ttc gac tac aac gcg aca gaa gat acc tca gac      3492
Gly Pro His Ile Cys Phe Asp Tyr Asn Ala Thr Glu Asp Thr Ser Asp
    1090                1095                1100 tgt ggc cgc ggg gcc tcc ttc ccg ccg tcg ctg ggc gtc ctg gtc tcc      3540
Cys Gly Arg Gly Ala Ser Phe Pro Pro Ser Leu Gly Val Leu Val Ser
1105                1110                1115                1120 ctg caa ctg ctg ctc ctc ctg ggc ctg ccg ccc cgg ccg cag cct caa      3588
Leu Gln Leu Leu Leu Leu Leu Gly Leu Pro Pro Arg Pro Gln Pro Gln
                1125                1130                1135 gtc ctc gtc cac gcc tct cgc cgc ctc tga gcaccctgcc ccaccccacc        3638
Val Leu Val His Ala Ser Arg Arg Leu
            1140            1145 tccactccca cctcacccgg cctcttcgcc tttcccaccc tcctgcccca cactccccgc    3698
cttagagcct cgtccctccc tcactgaagg acctgagctg gccaggcccct gagagtctgg   3758 tctgcgcctt gggatgggga gtcccaaagc gggacgccgc aggtgtttgg cacccaaatc    3818
acatctcacc tccgaactgt tcaagtgtcc ccagacccctt cttgcctgct gggctccccc   3878
cagtgggatg ggacagggag gccacacgca ctggtgccaa accaggcct ctgctgccgc     3938 ccttcctgga ggctgcctat gttgggggg accctgcctc agctgacccg gcctctctgc    3998
cccacccaag cccaaacttg gtttctgtga aatagtgga ggaaggtgag atggccagtt     4058
tgaagcctgt gcctcccagc ttaaatccta gcaggagaga ggctctgggg cagcccccat    4118
gggctcctgc ccctttcagg cctacagcca catcccccaag cccaccaggt gtcaggatag   4178
tcacagtgat accagttcag acactacccc atatcacct ggaacattga ggatggaaac     4238
tggactcaca ttcgacatac cccactgggc acacgcacaa acacacacac tatgggtgg     4298 ggtgggtgta gggcttaca aagccttaca cagggcgagg ggttggtggg agggttggca     4358
cctgcacact ccatctcctg ctcaccacct gcctctaatc tgagctgcag cctggctggt    4418
cctcccattt ctaaagctga atgtcaaaca gtgccaaatg ctggggcagg gggtgaagaa    4478
ccctctgtcc cacccctagc caccagtgtc ctccaagtgc ccctcacct ctccaggtgc     4538 tcattgtaac catttctcac tagtgtcagg ccccccagtgg gaccacatgc cactgcctgc   4598
acctttcggc agaggaaccc ccaccagaca tcacccttttg ccttagcagg ggtgactttg   4658
tctctcctgg ctgggccatc cttccgccaa tctggcccctt acacactcag gcctgtgccc   4718
```

-continued

```
actccctatc tccttcccac ccctacacac acactccctg cttgcaggag gccaaactgt      4778
ccctcccttg ctgaacacac acacacacac acacacacag gtggggactg ggcacagctc      4838
ttcacaccat tcattctggt catttccccc aaaggcatcc cagcctgggg gccagtgggg      4898
aactgagggc aagggatat agtgatgggg ctcagatgga ctgggaggag ggggagggtg       4958
atgcattaat taatggcttc gttaattaat gtcatgttgc ttgtcgcttt ctcagtgtgt      5018
gtgtgtggtc catgcccact gctggtgcca gggtgggtgt ccatgtgcac ccggcctgga      5078
tgccagctgt gtccttcggg ggcgtgcgtg taactgtagt gtagtcaggt gctcaatgga      5138
gaatataaac atatacagaa aaatatatat tttaagttta aaaaacagaa aaacagacaa      5198
aacaatcccc atcaggtagc tgtctaaccc ccagctgggt ctaatccttc tcattaccca      5258
cccgacctgg ctgcccctca ccttgggctg ggggactggg gggccatttc cttttctctg      5318
cccttttttt gttgttctat tttgtacaga caagttggaa aaacaacagc gacaaaaaag      5378
tcaagaaact ttgtaaaata tcgtgtgtgt gattccttgt aaaatatttt caaatggttt      5438
attacagaag atcagttatt aaataatgtt catattttca cttc                      5482
```

<210> SEQ ID NO 4
<211> LENGTH: 1145
<212> TYPE: PRT
<213> ORGANISM: Homo sapiens

<400> SEQUENCE: 4

```
Met Ala Val Pro Ala Arg Thr Cys Gly Ala Ser Arg Pro Gly Pro Ala
  1               5                  10                  15

Arg Thr Ala Arg Pro Trp Pro Gly Cys Gly Pro His Pro Gly Pro Gly
             20                  25                  30

Thr Arg Arg Pro Thr Ser Gly Pro Pro Arg Pro Leu Trp Leu Leu Leu
         35                  40                  45

Pro Leu Leu Pro Leu Leu Ala Ala Pro Gly Ala Ser Ala Tyr Ser Phe
     50                  55                  60

Pro Gln Gln His Thr Met Gln His Trp Ala Arg Arg Leu Glu Gln Glu
 65                  70                  75                  80

Val Asp Gly Val Met Arg Ile Phe Gly Gly Val Gln Gln Leu Arg Glu
                 85                  90                  95

Ile Tyr Lys Asp Asn Arg Asn Leu Phe Glu Val Gln Glu Asn Glu Pro
            100                 105                 110

Gln Lys Leu Val Glu Lys Val Ala Gly Asp Ile Glu Ser Leu Leu Asp
        115                 120                 125

Arg Lys Val Gln Ala Leu Lys Arg Leu Ala Asp Ala Ala Glu Asn Phe
    130                 135                 140

Gln Lys Ala His Arg Trp Gln Asp Asn Ile Lys Glu Glu Asp Ile Val
145                 150                 155                 160

Tyr Tyr Asp Ala Lys Ala Asp Ala Glu Leu Asp Asp Pro Glu Ser Glu
                165                 170                 175

Asp Val Glu Arg Gly Ser Lys Ala Ser Thr Leu Arg Leu Asp Phe Ile
            180                 185                 190

Glu Asp Pro Asn Phe Lys Asn Lys Val Asn Tyr Ser Tyr Ala Ala Val
        195                 200                 205

Gln Ile Pro Thr Asp Ile Tyr Lys Gly Ser Thr Val Ile Leu Asn Glu
    210                 215                 220

Leu Asn Trp Thr Glu Ala Leu Glu Asn Val Phe Met Glu Asn Arg Arg
225                 230                 235                 240
```

-continued

```
Gln Asp Pro Thr Leu Leu Trp Gln Val Phe Gly Ser Ala Thr Gly Val
                245                 250                 255

Thr Arg Tyr Tyr Pro Ala Thr Pro Trp Arg Ala Pro Lys Lys Ile Asp
            260                 265                 270

Leu Tyr Asp Val Arg Arg Pro Trp Tyr Ile Gln Gly Ala Ser Ser
        275                 280                 285

Pro Lys Asp Met Val Ile Ile Val Asp Val Ser Gly Ser Val Ser Gly
    290                 295                 300

Leu Thr Leu Lys Leu Met Lys Thr Ser Val Cys Glu Met Leu Asp Thr
305                 310                 315                 320

Leu Ser Asp Asp Tyr Val Asn Val Ala Ser Phe Asn Glu Lys Ala
            325                 330                 335

Gln Pro Val Ser Cys Phe Thr His Leu Val Gln Ala Asn Val Arg Asn
                340                 345                 350

Lys Lys Val Phe Lys Glu Ala Val Gln Gly Met Val Ala Lys Gly Thr
            355                 360                 365

Thr Gly Tyr Lys Ala Gly Phe Glu Tyr Ala Phe Asp Gln Leu Gln Asn
    370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                405                 410                 415

Pro Asn Arg Thr Val Arg Val Phe Thr Phe Ser Val Gly Gln His Asn
            420                 425                 430

Tyr Asp Val Thr Pro Leu Gln Trp Met Ala Cys Ala Asn Lys Gly Tyr
        435                 440                 445

Tyr Phe Glu Ile Pro Ser Ile Gly Ala Ile Arg Ile Asn Thr Gln Glu
    450                 455                 460

Tyr Leu Asp Val Leu Gly Arg Pro Met Val Leu Ala Gly Lys Glu Ala
465                 470                 475                 480

Lys Gln Val Gln Trp Thr Asn Val Tyr Glu Asp Ala Leu Gly Leu Gly
                485                 490                 495

Leu Val Val Thr Gly Thr Leu Pro Val Phe Asn Leu Thr Gln Asp Gly
            500                 505                 510

Pro Gly Glu Lys Lys Asn Gln Leu Ile Leu Gly Val Met Gly Ile Asp
        515                 520                 525

Val Ala Leu Asn Asp Ile Lys Arg Leu Thr Pro Asn Tyr Thr Leu Gly
    530                 535                 540

Ala Asn Gly Tyr Val Phe Ala Ile Asp Leu Asn Gly Tyr Val Leu Leu
545                 550                 555                 560

His Pro Asn Leu Lys Pro Gln Thr Thr Asn Phe Arg Glu Pro Val Thr
                565                 570                 575

Leu Asp Phe Leu Asp Ala Glu Leu Glu Asp Glu Asn Lys Glu Glu Ile
            580                 585                 590

Arg Arg Ser Met Ile Asp Gly Asn Lys Gly His Lys Gln Ile Arg Thr
        595                 600                 605

Leu Val Lys Ser Leu Asp Glu Arg Tyr Ile Asp Glu Val Thr Arg Asn
    610                 615                 620

Tyr Thr Trp Val Pro Ile Arg Ser Thr Asn Tyr Ser Leu Gly Leu Val
625                 630                 635                 640

Leu Pro Pro Tyr Ser Thr Phe Tyr Leu Gln Ala Asn Leu Ser Asp Gln
                645                 650                 655

Ile Leu Gln Val Lys Tyr Phe Glu Phe Leu Leu Pro Ser Ser Phe Glu
```

-continued

```
                    660                     665                     670
Ser Glu Gly His Val Phe Ile Ala Pro Arg Glu Tyr Cys Lys Asp Leu
            675                     680                     685

Asn Ala Ser Asp Asn Asn Thr Glu Phe Leu Lys Asn Phe Ile Glu Leu
            690                     695                     700

Met Glu Lys Val Thr Pro Asp Ser Lys Gln Cys Asn Asn Phe Leu Leu
705                     710                     715                 720

His Asn Leu Ile Leu Asp Thr Gly Ile Thr Gln Gln Leu Val Glu Arg
                    725                     730                     735

Val Trp Arg Asp Gln Asp Leu Asn Thr Tyr Ser Leu Leu Ala Val Phe
                740                     745                     750

Ala Ala Thr Asp Gly Gly Ile Thr Arg Val Phe Pro Asn Lys Ala Ala
            755                     760                     765

Glu Asp Trp Thr Glu Asn Pro Glu Pro Phe Asn Ala Ser Phe Tyr Arg
770                     775                     780

Arg Ser Leu Asp Asn His Gly Tyr Val Phe Lys Pro Pro His Gln Asp
785                     790                     795                 800

Ala Leu Leu Arg Pro Leu Glu Leu Glu Asn Asp Thr Val Gly Ile Leu
                    805                     810                     815

Val Ser Thr Ala Val Glu Leu Ser Leu Gly Arg Arg Thr Leu Arg Pro
                820                     825                     830

Ala Val Val Gly Val Lys Leu Asp Leu Glu Ala Trp Ala Glu Lys Phe
            835                     840                     845

Lys Val Leu Ala Ser Asn Arg Thr His Gln Asp Gln Pro Gln Lys Cys
        850                     855                     860

Gly Pro Asn Ser His Cys Glu Met Asp Cys Glu Val Asn Asn Glu Asp
865                     870                     875                 880

Leu Leu Cys Val Leu Ile Asp Asp Gly Gly Phe Leu Val Leu Ser Asn
                    885                     890                     895

Gln Asn His Gln Trp Asp Gln Val Gly Arg Phe Phe Ser Glu Val Asp
                900                     905                     910

Ala Asn Leu Met Leu Ala Leu Tyr Asn Asn Ser Phe Tyr Thr Arg Lys
            915                     920                     925

Glu Ser Tyr Asp Tyr Gln Ala Ala Cys Ala Pro Gln Pro Pro Gly Asn
930                     935                     940

Leu Gly Ala Ala Pro Arg Gly Val Phe Val Pro Thr Val Ala Asp Phe
945                     950                     955                 960

Leu Asn Leu Ala Trp Trp Thr Ser Ala Ala Trp Ser Leu Phe Gln
                    965                     970                     975

Gln Leu Leu Tyr Gly Leu Ile Tyr His Ser Trp Phe Gln Ala Asp Pro
                980                     985                     990

Ala Glu Ala Glu Gly Ser Pro Glu Thr Arg Glu Ser Ser Cys Val Met
            995                     1000                    1005

Lys Gln Thr Gln Tyr Tyr Phe Gly Ser Val Asn Ala Ser Tyr Asn Ala
    1010                    1015                    1020

Ile Ile Asp Cys Gly Asn Cys Ser Arg Leu Phe His Ala Gln Arg Leu
1025                    1030                    1035                1040

Thr Asn Thr Asn Leu Leu Phe Val Val Ala Glu Lys Pro Leu Cys Ser
                    1045                    1050                    1055

Gln Cys Glu Ala Gly Arg Leu Leu Gln Lys Glu Thr His Cys Pro Ala
                1060                    1065                    1070

Asp Gly Pro Glu Gln Cys Glu Leu Val Gln Arg Pro Arg Tyr Arg Arg
            1075                    1080                    1085
```

```
Gly Pro His Ile Cys Phe Asp Tyr Asn Ala Thr Glu Asp Thr Ser Asp
    1090                1095                1100

Cys Gly Arg Gly Ala Ser Phe Pro Pro Ser Leu Gly Val Leu Val Ser
1105                1110                1115                1120

Leu Gln Leu Leu Leu Leu Leu Gly Leu Pro Pro Arg Pro Gln Pro Gln
                1125                1130                1135

Val Leu Val His Ala Ser Arg Arg Leu
            1140                1145

<210> SEQ ID NO 5
<211> LENGTH: 5279
<212> TYPE: DNA
<213> ORGANISM: Homo sapiens
<220> FEATURE:
<221> NAME/KEY: CDS
<222> LOCATION: (185)..(3415)

<400> SEQUENCE: 5
```

| | | |
|---|---|---:|
| atccgcggcg aagcgagtgg ctgcagaggg ctgcatcctg ccgtcccag cccccacaa | | 60 |
| ccgtacagcc gtgcccaggt ttccgcttag ggaaccagga ggtccaggcc ctttctgcca | | 120 |
| gcagccgggc gtgcaagccc ccgacagaga gaaatcttaa agatagctag agccacgggg | | 180 |

```
gctg atg cag cac tgg gcc cgg cgt ctg gag cag gag gtc gac ggc gtg    229
     Met Gln His Trp Ala Arg Arg Leu Glu Gln Glu Val Asp Gly Val
     1               5                   10                  15 atg cgg att ttt gga ggc gtc cag cag ctc cgt gag att tac aag gac    277
Met Arg Ile Phe Gly Gly Val Gln Gln Leu Arg Glu Ile Tyr Lys Asp
                20                  25                  30 aac cgg aac ctg ttc gag gta cag gag aat gag cct cag aag ttg gtg    325
Asn Arg Asn Leu Phe Glu Val Gln Glu Asn Glu Pro Gln Lys Leu Val
            35                  40                  45 gag aag gtg gca ggg gac att gag agc ctt ctg gac agg aag gtg cag    373
Glu Lys Val Ala Gly Asp Ile Glu Ser Leu Leu Asp Arg Lys Val Gln
        50                  55                  60 gcc ctg aag aga ctg gct gat gct gca gag aac ttc cag aaa gca cac    421
Ala Leu Lys Arg Leu Ala Asp Ala Ala Glu Asn Phe Gln Lys Ala His
    65                  70                  75 cgc tgg cag gac aac atc aag gag gaa gac atc gtg tac tat gac gcc    469
Arg Trp Gln Asp Asn Ile Lys Glu Glu Asp Ile Val Tyr Tyr Asp Ala
80                  85                  90                  95 aag gct gac gct gag ctg gac gac cct gag agt gag gat gtg gaa agg    517
Lys Ala Asp Ala Glu Leu Asp Asp Pro Glu Ser Glu Asp Val Glu Arg
                100                 105                 110 ggg tct aag gcc agc acc cta agg ctg gac ttc atc gag gac cca aac    565
Gly Ser Lys Ala Ser Thr Leu Arg Leu Asp Phe Ile Glu Asp Pro Asn
            115                 120                 125 ttc aag aac aag gtc aac tat tca tac gcg gct gta cag atc cct acg    613
Phe Lys Asn Lys Val Asn Tyr Ser Tyr Ala Ala Val Gln Ile Pro Thr
        130                 135                 140 gac atc tac aaa ggc tcc act gtc atc ctc aat gag ctc aac tgg aca    661
Asp Ile Tyr Lys Gly Ser Thr Val Ile Leu Asn Glu Leu Asn Trp Thr
    145                 150                 155 gag gcc ctg gag aat gtg ttc atg gaa aac cgc aga caa gac ccc aca    709
Glu Ala Leu Glu Asn Val Phe Met Glu Asn Arg Arg Gln Asp Pro Thr
160                 165                 170                 175 ctg ctg tgg cag gtc ttc ggc agc gcc aca gga gtc act cgc tac tac    757
Leu Leu Trp Gln Val Phe Gly Ser Ala Thr Gly Val Thr Arg Tyr Tyr
                180                 185                 190 ccg gcc acc ccg tgg cga gcc ccc aag aag atc gac ctg tac gat gtc    805
```

```
                                                              -continued

Pro Ala Thr Pro Trp Arg Ala Pro Lys Lys Ile Asp Leu Tyr Asp Val
            195                 200                 205 cga agg aga ccc tgg tat atc cag ggg gcc tcg tca ccc aaa gac atg      853
Arg Arg Arg Pro Trp Tyr Ile Gln Gly Ala Ser Ser Pro Lys Asp Met
            210                 215                 220 gtc atc atc gtg gat gtg agt ggc agt gtg agc ggc ctg acc ctg aag      901
Val Ile Ile Val Asp Val Ser Gly Ser Val Ser Gly Leu Thr Leu Lys
            225                 230                 235 ctg atg aag aca tct gtc tgc gag atg ctg gac acg ctg tct gat gat      949
Leu Met Lys Thr Ser Val Cys Glu Met Leu Asp Thr Leu Ser Asp Asp
240                 245                 250                 255 gac tat gtg aat gtg gcc tcg ttc aac gag aag gca cag cct gtg tca      997
Asp Tyr Val Asn Val Ala Ser Phe Asn Glu Lys Ala Gln Pro Val Ser
                260                 265                 270 tgc ttc aca cac ctg gtg cag gcc aat gtg cgc aac aag aag gtg ttc     1045
Cys Phe Thr His Leu Val Gln Ala Asn Val Arg Asn Lys Lys Val Phe
            275                 280                 285 aag gaa gct gtg cag ggc atg gtg gcc aag ggc acc aca ggc tac aag     1093
Lys Glu Ala Val Gln Gly Met Val Ala Lys Gly Thr Thr Gly Tyr Lys
            290                 295                 300 gcc ggc ttt gag tat gcc ttt gac cag ctg cag aac tcc aac atc act     1141
Ala Gly Phe Glu Tyr Ala Phe Asp Gln Leu Gln Asn Ser Asn Ile Thr
305                 310                 315 cgg gcc aac tgc aac aag atg atc atg atg ttc acg gat ggt ggt gag     1189
Arg Ala Asn Cys Asn Lys Met Ile Met Met Phe Thr Asp Gly Gly Glu
320                 325                 330                 335 gac cgc gtg cag gac gtc ttt gag aag tac aat tgg cca aac cgg acg     1237
Asp Arg Val Gln Asp Val Phe Glu Lys Tyr Asn Trp Pro Asn Arg Thr
            340                 345                 350 gtg cgc gtg ttt act ttc tcc gtg ggg cag cat aac tat gac gtc aca     1285
Val Arg Val Phe Thr Phe Ser Val Gly Gln His Asn Tyr Asp Val Thr
            355                 360                 365 ccg ctg cag tgg atg gcc tgt gcc aac aaa ggc tac tat ttt gag atc     1333
Pro Leu Gln Trp Met Ala Cys Ala Asn Lys Gly Tyr Tyr Phe Glu Ile
            370                 375                 380 cct tcc atc gga gcc atc cgc atc aac aca cag gaa tat cta gat gtg     1381
Pro Ser Ile Gly Ala Ile Arg Ile Asn Thr Gln Glu Tyr Leu Asp Val
385                 390                 395 ttg ggc agg ccc atg gtg ctg gca ggc aag gag gcc aag cag gtt cag     1429
Leu Gly Arg Pro Met Val Leu Ala Gly Lys Glu Ala Lys Gln Val Gln
400                 405                 410                 415 tgg acc aac gtg tat gag gat gca ctg gga ctg ggg ttg gtg gta aca     1477
Trp Thr Asn Val Tyr Glu Asp Ala Leu Gly Leu Gly Leu Val Val Thr
            420                 425                 430 ggg acc ctc cct gtt ttc aac ctg aca cag gat ggc cct ggg gaa aag     1525
Gly Thr Leu Pro Val Phe Asn Leu Thr Gln Asp Gly Pro Gly Glu Lys
            435                 440                 445 aag aac cag ctg atc ctg ggc gtg atg ggc att gac gtg gct ctg aat     1573
Lys Asn Gln Leu Ile Leu Gly Val Met Gly Ile Asp Val Ala Leu Asn
            450                 455                 460 gac atc aag agg ctg acc ccc aac tac acg ctt gga gcc aac ggc tat     1621
Asp Ile Lys Arg Leu Thr Pro Asn Tyr Thr Leu Gly Ala Asn Gly Tyr
465                 470                 475 gtg ttt gcc att gac ctg aac ggc tac gtg ttg ctg cac ccc aat ctc     1669
Val Phe Ala Ile Asp Leu Asn Gly Tyr Val Leu Leu His Pro Asn Leu
480                 485                 490                 495 aag ccc cag acc acc aac ttc cgg gag cct gtg act ctg gac ttc ctg     1717
Lys Pro Gln Thr Thr Asn Phe Arg Glu Pro Val Thr Leu Asp Phe Leu
            500                 505                 510
```

-continued

| | |
|---|---|
| gat gcg gag cta gag gat gag aac aag gaa gag atc cgt cgg agc atg<br>Asp Ala Glu Leu Glu Asp Glu Asn Lys Glu Glu Ile Arg Arg Ser Met<br>        515                   520             525 | 1765 |
| att gat ggc aac aag ggc cac aag cag atc aga acg ttg gtc aag tcc<br>Ile Asp Gly Asn Lys Gly His Lys Gln Ile Arg Thr Leu Val Lys Ser<br>    530                   535                 540 | 1813 |
| ctg gat gag agg tac ata gat gag gtg aca cgg aac tac acc tgg gtg<br>Leu Asp Glu Arg Tyr Ile Asp Glu Val Thr Arg Asn Tyr Thr Trp Val<br>545                 550                 555 | 1861 |
| cct ata agg agc act aac tac agc ctg ggg ctg gtg ctc cca ccc tac<br>Pro Ile Arg Ser Thr Asn Tyr Ser Leu Gly Leu Val Leu Pro Pro Tyr<br>560                 565             570             575 | 1909 |
| agc acc ttc tac ctc caa gcc aat ctc agt gac cag atc ctg cag gtc<br>Ser Thr Phe Tyr Leu Gln Ala Asn Leu Ser Asp Gln Ile Leu Gln Val<br>                 580             585                 590 | 1957 |
| aag tat ttt gag ttc ctg ctc ccc agc agc ttt gag tct gaa gga cac<br>Lys Tyr Phe Glu Phe Leu Leu Pro Ser Ser Phe Glu Ser Glu Gly His<br>    595                 600                 605 | 2005 |
| gtt ttc att gct ccc aga gag tac tgc aag gac ctg aat gcc tca gac<br>Val Phe Ile Ala Pro Arg Glu Tyr Cys Lys Asp Leu Asn Ala Ser Asp<br>610                 615             620 | 2053 |
| aac aac acc gag ttc ctg aaa aac ttt att gag ctc atg gag aaa gtg<br>Asn Asn Thr Glu Phe Leu Lys Asn Phe Ile Glu Leu Met Glu Lys Val<br>625                 630                 635 | 2101 |
| act cca gac tcc aag cag tgc aac aac ttc ctt ctg cac aac ctg atc<br>Thr Pro Asp Ser Lys Gln Cys Asn Asn Phe Leu Leu His Asn Leu Ile<br>640                 645             650             655 | 2149 |
| ttg gac acg ggc atc acg cag cag ctg gta gag cgt gtg tgg agg gac<br>Leu Asp Thr Gly Ile Thr Gln Gln Leu Val Glu Arg Val Trp Arg Asp<br>                 660             665                 670 | 2197 |
| cag gat ctc aac acg tac agc cta ctg gcc gtg ttc gct gcc aca gac<br>Gln Asp Leu Asn Thr Tyr Ser Leu Leu Ala Val Phe Ala Ala Thr Asp<br>    675                 680                 685 | 2245 |
| ggt ggc atc acc cga gtc ttc ccc aac aag gca gct gag gac tgg aca<br>Gly Gly Ile Thr Arg Val Phe Pro Asn Lys Ala Ala Glu Asp Trp Thr<br>690                 695             700 | 2293 |
| gag aac cct gag ccc ttc aat gcc agc ttc tac cgc cgc agc ctg gat<br>Glu Asn Pro Glu Pro Phe Asn Ala Ser Phe Tyr Arg Arg Ser Leu Asp<br>705                 710                 715 | 2341 |
| aac cac ggt tat gtc ttc aag ccc cca cac cag gat gcc ctg tta agg<br>Asn His Gly Tyr Val Phe Lys Pro Pro His Gln Asp Ala Leu Leu Arg<br>720                 725             730             735 | 2389 |
| ccg ctg gag ctg gag aat gac act gtg ggc atc ctc gtc agc aca gct<br>Pro Leu Glu Leu Glu Asn Asp Thr Val Gly Ile Leu Val Ser Thr Ala<br>                 740             745                 750 | 2437 |
| gtg gag ctc agc cta ggc agg cgc aca ctg agg cca gca gtg gtg ggc<br>Val Glu Leu Ser Leu Gly Arg Arg Thr Leu Arg Pro Ala Val Val Gly<br>    755                 760                 765 | 2485 |
| gtc aag ctg gac cta gag gct tgg gct gag aag ttc aag gtg cta gcc<br>Val Lys Leu Asp Leu Glu Ala Trp Ala Glu Lys Phe Lys Val Leu Ala<br>770                 775             780 | 2533 |
| agc aac cgt acc cac caa gac cag cct cag aag tgc ggc ccc aac agc<br>Ser Asn Arg Thr His Gln Asp Gln Pro Gln Lys Cys Gly Pro Asn Ser<br>785                 790             795 | 2581 |
| cac tgt gag atg gac tgc gag gtt aac aat gag gac tta ctc tgt gtc<br>His Cys Glu Met Asp Cys Glu Val Asn Asn Glu Asp Leu Leu Cys Val<br>800                 805             810             815 | 2629 |
| ctc att gat gat gga gga ttc ctg gtg ctg tca aac cag aac cat cag<br>Leu Ile Asp Asp Gly Gly Phe Leu Val Leu Ser Asn Gln Asn His Gln<br>                 820             825                 830 | 2677 |

-continued

```
tgg gac cag gtg ggc agg ttc ttc agt gag gtg gat gcc aac ctg atg      2725
Trp Asp Gln Val Gly Arg Phe Phe Ser Glu Val Asp Ala Asn Leu Met
            835                 840                 845 ctg gca ctc tac aat aac tcc ttc tac acc cgc aag gag tcc tat gac      2773
Leu Ala Leu Tyr Asn Asn Ser Phe Tyr Thr Arg Lys Glu Ser Tyr Asp
        850                 855                 860 tat cag gca gcc tgt gcc cct cag ccc cct ggc aac ctg ggt gct gca      2821
Tyr Gln Ala Ala Cys Ala Pro Gln Pro Pro Gly Asn Leu Gly Ala Ala
    865                 870                 875 ccc cgg ggt gtc ttt gtg ccc acc gtt gca gat ttc ctt aac ctg gcc      2869
Pro Arg Gly Val Phe Val Pro Thr Val Ala Asp Phe Leu Asn Leu Ala
880                 885                 890                 895 tgg tgg acc tct gct gcc gcc tgg tcc ctg ttc cag cag ctt ctc tac      2917
Trp Trp Thr Ser Ala Ala Ala Trp Ser Leu Phe Gln Gln Leu Leu Tyr
                900                 905                 910 ggc ctc atc tac cac agc tgg ttc caa gca gac ccc gcg gag gcc gag      2965
Gly Leu Ile Tyr His Ser Trp Phe Gln Ala Asp Pro Ala Glu Ala Glu
            915                 920                 925 ggg agc ccc gag acg cgc gag agc agc tgc gtc atg aaa cag acc cag      3013
Gly Ser Pro Glu Thr Arg Glu Ser Ser Cys Val Met Lys Gln Thr Gln
        930                 935                 940 tac tac ttc ggc tcg gta aac gcc tcc tac aac gcc atc atc gac tgc      3061
Tyr Tyr Phe Gly Ser Val Asn Ala Ser Tyr Asn Ala Ile Ile Asp Cys
    945                 950                 955 gga aac tgc tcc agg ctg ttc cac gcg cag aga ctg acc aac acc aat      3109
Gly Asn Cys Ser Arg Leu Phe His Ala Gln Arg Leu Thr Asn Thr Asn
960                 965                 970                 975 ctt ctc ttt gtg gtg gcc gag aag ccg ctg tgc agc cag tgc gag gct      3157
Leu Leu Phe Val Val Ala Glu Lys Pro Leu Cys Ser Gln Cys Glu Ala
                980                 985                 990 ggc cgg ctg ctg cag aag gag acg cac tgc cca gcg gac ggc ccg gag      3205
Gly Arg Leu Leu Gln Lys Glu Thr His Cys Pro Ala Asp Gly Pro Glu
            995                 1000                1005 cag tgt gag cta gtg cag aga ccg cga tac cgg aga ggc ccg cac atc      3253
Gln Cys Glu Leu Val Gln Arg Pro Arg Tyr Arg Arg Gly Pro His Ile
        1010                1015                1020 tgc ttc gac tac aac gcg aca gaa gat acc tca gac tgt ggc cgc ggg      3301
Cys Phe Asp Tyr Asn Ala Thr Glu Asp Thr Ser Asp Cys Gly Arg Gly
    1025                1030                1035 gcc tcc ttc ccg ccg tcg ctg ggc gtc ctg gtc tcc ctg caa ctg ctg      3349
Ala Ser Phe Pro Pro Ser Leu Gly Val Leu Val Ser Leu Gln Leu Leu
1040                1045                1050                1055 ctc ctc ctg ggc ctg ccg ccc cgg ccg cag cct caa gtc ctc gtc cac      3397
Leu Leu Leu Gly Leu Pro Pro Arg Pro Gln Pro Gln Val Leu Val His
                1060                1065                1070 gcc tct cgc cgc ctc tga gcaccctgcc ccaccccacc tccactccca             3445
Ala Ser Arg Arg Leu
            1075 cctcacccgg cctcttcgcc tttcccaccc tcctgcccca cactcccgc cttagagcct     3505 cgtccctccc tcactgaagg acctgagctg gccaggccct gagagtctgg tctgcgcctt    3565 gggatgggga gtcccaaagc gggacgccgc aggtgtttgg cacccaaatc acatctcacc    3625 tccgaactgt tcaagtgtcc ccagacccct cttgcctgct gggctccccc cagtgggatg    3685 ggacagggag gccacacgca ctggtgccaa aaccaggcct ctgctgccgc ccttcctgga    3745 ggctgcctat gttgggggg accctgcctc agctgacccg gcctctctgc cccacccaag    3805 cccaaacttg gtttctgtga gaatagtgga ggaaggtgag atggccagtt tgaagcctgt    3865
```

-continued

```
gcctcccagc ttaaatccta gcaggagaga ggctctgggg cagcccccat gggctcctgc    3925 cccttttcagg cctacagcca catccccaag cccaccaggt gtcaggatag tcacagtgat   3985
accagttcag acactacccc atatacacct ggaacattga ggatggaaac tggactcaca    4045
ttcgacatac cccactgggc acacgcacaa acacacacac tatggggtgg ggtgggtgta    4105
ggggcttaca aagccttaca cagggcgagg ggttggtggg agggttggca cctgcacact    4165
ccatctcctg ctcaccacct gcctctaatc tgagctgcag cctggctggt cctcccattt    4225
ctaaagctga atgtcaaaca gtgccaaatg ctggggcagg gggtgaagaa ccctctgtcc    4285 caccccctagc caccagtgtc ctccaagtgc cccctcacct ctccaggtgc tcattgtaac   4345
catttctcac tagtgtcagg cccccagtgg gaccacatgc cactgcctgc acctttcggc    4405
agaggaaccc ccaccagaca tcacccttg ccttagcagg ggtgactttg tctctcctgg     4465
ctgggccatc cttccgccaa tctggcccct acacactcag gcctgtgccc actccctatc    4525
tccttcccac ccctacacac acactccctg cttgcaggag gccaaactgt ccctcccttg    4585
ctgaacacac acacacacac acacacacag gtggggactg ggcacagctc ttcacaccat    4645
tcattctggt catttccccc aaaggcatcc cagcctgggg gccagtgggg aactgagggc    4705 aagggggatat agtgatgggg ctcagatgga ctgggaggag gggagggtg atgcattaat    4765 taatggcttc gttaattaat gtcatgttgc ttgtcgcttt ctcagtgtgt gtgtgtggtc    4825
catgcccact gctggtgcca gggtgggtgt ccatgtgcac ccggcctgga tgccagctgt    4885
gtccttcggg ggcgtgcgtg taactgtagt gtagtcaggt gctcaatgga gaatataaac    4945
atatacagaa aaatatatat tttaagttta aaaacagaa aaacagacaa aacaatcccc     5005
atcaggtagc tgtctaaccc ccagctgggt ctaatccttc tcattaccca cccgacctgg    5065 ctgccccctca ccttgggctg ggggactggg gggccatttc cttttctctg ccctttttt    5125 gttgttctat tttgtacaga caagttggaa aaacaacagc gacaaaaaag tcaagaaact    5185
ttgtaaaata tcgtgtgtgt gattccttgt aaaatatttt caaatggttt attacagaag   5245
atcagttatt aaataatgtt catattttca cttc                                5279
```

<210> SEQ ID NO 6
<211> LENGTH: 1076
<212> TYPE: PRT
<213> ORGANISM: Homo sapiens

<400> SEQUENCE: 6

```
Met Gln His Trp Ala Arg Arg Leu Glu Gln Glu Val Asp Gly Val Met
 1               5                  10                  15

Arg Ile Phe Gly Gly Val Gln Gln Leu Arg Glu Ile Tyr Lys Asp Asn
            20                  25                  30

Arg Asn Leu Phe Glu Val Gln Glu Asn Glu Pro Gln Lys Leu Val Glu
        35                  40                  45

Lys Val Ala Gly Asp Ile Glu Ser Leu Leu Asp Arg Lys Val Gln Ala
    50                  55                  60

Leu Lys Arg Leu Ala Asp Ala Ala Glu Asn Phe Gln Lys Ala His Arg
65                  70                  75                  80

Trp Gln Asp Asn Ile Lys Glu Glu Asp Ile Val Tyr Tyr Asp Ala Lys
                85                  90                  95

Ala Asp Ala Glu Leu Asp Asp Pro Glu Ser Glu Asp Val Glu Arg Gly
            100                 105                 110

Ser Lys Ala Ser Thr Leu Arg Leu Asp Phe Ile Glu Asp Pro Asn Phe
        115                 120                 125
```

```
Lys Asn Lys Val Asn Tyr Ser Tyr Ala Ala Val Gln Ile Pro Thr Asp
    130                 135                 140
Ile Tyr Lys Gly Ser Thr Val Ile Leu Asn Glu Leu Asn Trp Thr Glu
145                 150                 155                 160
Ala Leu Glu Asn Val Phe Met Glu Asn Arg Arg Gln Asp Pro Thr Leu
                165                 170                 175
Leu Trp Gln Val Phe Gly Ser Ala Thr Gly Val Thr Arg Tyr Tyr Pro
            180                 185                 190
Ala Thr Pro Trp Arg Ala Pro Lys Lys Ile Asp Leu Tyr Asp Val Arg
        195                 200                 205
Arg Arg Pro Trp Tyr Ile Gln Gly Ala Ser Ser Pro Lys Asp Met Val
    210                 215                 220
Ile Ile Val Asp Val Ser Gly Ser Val Ser Gly Leu Thr Leu Lys Leu
225                 230                 235                 240
Met Lys Thr Ser Val Cys Glu Met Leu Asp Thr Leu Ser Asp Asp Asp
                245                 250                 255
Tyr Val Asn Val Ala Ser Phe Asn Glu Lys Ala Gln Pro Val Ser Cys
            260                 265                 270
Phe Thr His Leu Val Gln Ala Asn Val Arg Asn Lys Lys Val Phe Lys
        275                 280                 285
Glu Ala Val Gln Gly Met Val Ala Lys Gly Thr Thr Gly Tyr Lys Ala
    290                 295                 300
Gly Phe Glu Tyr Ala Phe Asp Gln Leu Gln Asn Ser Asn Ile Thr Arg
305                 310                 315                 320
Ala Asn Cys Asn Lys Met Ile Met Met Phe Thr Asp Gly Gly Glu Asp
                325                 330                 335
Arg Val Gln Asp Val Phe Glu Lys Tyr Asn Trp Pro Asn Arg Thr Val
            340                 345                 350
Arg Val Phe Thr Phe Ser Val Gly Gln His Asn Tyr Asp Val Thr Pro
        355                 360                 365
Leu Gln Trp Met Ala Cys Ala Asn Lys Gly Tyr Tyr Phe Glu Ile Pro
    370                 375                 380
Ser Ile Gly Ala Ile Arg Ile Asn Thr Gln Glu Tyr Leu Asp Val Leu
385                 390                 395                 400
Gly Arg Pro Met Val Leu Ala Gly Lys Glu Ala Lys Gln Val Gln Trp
                405                 410                 415
Thr Asn Val Tyr Glu Asp Ala Leu Gly Leu Gly Leu Val Val Thr Gly
            420                 425                 430
Thr Leu Pro Val Phe Asn Leu Thr Gln Asp Gly Pro Gly Glu Lys Lys
        435                 440                 445
Asn Gln Leu Ile Leu Gly Val Met Gly Ile Asp Val Ala Leu Asn Asp
    450                 455                 460
Ile Lys Arg Leu Thr Pro Asn Tyr Thr Leu Gly Ala Asn Gly Tyr Val
465                 470                 475                 480
Phe Ala Ile Asp Leu Asn Gly Tyr Val Leu Leu His Pro Asn Leu Lys
                485                 490                 495
Pro Gln Thr Thr Asn Phe Arg Glu Pro Val Thr Leu Asp Phe Leu Asp
            500                 505                 510
Ala Glu Leu Glu Asp Glu Asn Lys Glu Glu Ile Arg Arg Ser Met Ile
        515                 520                 525
Asp Gly Asn Lys Gly His Lys Gln Ile Arg Thr Leu Val Lys Ser Leu
    530                 535                 540
```

```
Asp Glu Arg Tyr Ile Asp Glu Val Thr Arg Asn Tyr Thr Trp Val Pro
545                 550                 555                 560

Ile Arg Ser Thr Asn Tyr Ser Leu Gly Leu Val Leu Pro Pro Tyr Ser
                565                 570                 575

Thr Phe Tyr Leu Gln Ala Asn Leu Ser Asp Gln Ile Leu Gln Val Lys
                580                 585                 590

Tyr Phe Glu Phe Leu Leu Pro Ser Ser Phe Glu Ser Glu Gly His Val
            595                 600                 605

Phe Ile Ala Pro Arg Glu Tyr Cys Lys Asp Leu Asn Ala Ser Asp Asn
        610                 615                 620

Asn Thr Glu Phe Leu Lys Asn Phe Ile Glu Leu Met Glu Lys Val Thr
625                 630                 635                 640

Pro Asp Ser Lys Gln Cys Asn Asn Phe Leu His Asn Leu Ile Leu
                645                 650                 655

Asp Thr Gly Ile Thr Gln Gln Leu Val Glu Arg Val Trp Arg Asp Gln
                660                 665                 670

Asp Leu Asn Thr Tyr Ser Leu Leu Ala Val Phe Ala Ala Thr Asp Gly
            675                 680                 685

Gly Ile Thr Arg Val Phe Pro Asn Lys Ala Ala Glu Asp Trp Thr Glu
        690                 695                 700

Asn Pro Glu Pro Phe Asn Ala Ser Phe Tyr Arg Arg Ser Leu Asp Asn
705                 710                 715                 720

His Gly Tyr Val Phe Lys Pro Pro His Gln Asp Ala Leu Leu Arg Pro
                725                 730                 735

Leu Glu Leu Glu Asn Asp Thr Val Gly Ile Leu Val Ser Thr Ala Val
                740                 745                 750

Glu Leu Ser Leu Gly Arg Arg Thr Leu Arg Pro Ala Val Val Gly Val
            755                 760                 765

Lys Leu Asp Leu Glu Ala Trp Ala Glu Lys Phe Lys Val Leu Ala Ser
        770                 775                 780

Asn Arg Thr His Gln Asp Gln Pro Gln Lys Cys Gly Pro Asn Ser His
785                 790                 795                 800

Cys Glu Met Asp Cys Glu Val Asn Asn Glu Asp Leu Leu Cys Val Leu
                805                 810                 815

Ile Asp Asp Gly Gly Phe Leu Val Leu Ser Asn Gln Asn His Gln Trp
                820                 825                 830

Asp Gln Val Gly Arg Phe Phe Ser Glu Val Asp Ala Asn Leu Met Leu
            835                 840                 845

Ala Leu Tyr Asn Asn Ser Phe Tyr Thr Arg Lys Glu Ser Tyr Asp Tyr
        850                 855                 860

Gln Ala Ala Cys Ala Pro Gln Pro Gly Asn Leu Gly Ala Ala Pro
865                 870                 875                 880

Arg Gly Val Phe Val Pro Thr Val Ala Asp Phe Leu Asn Leu Ala Trp
                885                 890                 895

Trp Thr Ser Ala Ala Ala Trp Ser Leu Phe Gln Gln Leu Leu Tyr Gly
                900                 905                 910

Leu Ile Tyr His Ser Trp Phe Gln Ala Asp Pro Ala Glu Ala Glu Gly
            915                 920                 925

Ser Pro Glu Thr Arg Glu Ser Ser Cys Val Met Lys Gln Thr Gln Tyr
        930                 935                 940

Tyr Phe Gly Ser Val Asn Ala Ser Tyr Asn Ala Ile Ile Asp Cys Gly
945                 950                 955                 960

Asn Cys Ser Arg Leu Phe His Ala Gln Arg Leu Thr Asn Thr Asn Leu
```

```
                       965                 970                 975
Leu Phe Val Val Ala Glu Lys Pro Leu Cys Ser Gln Cys Glu Ala Gly
                    980                 985                 990
Arg Leu Leu Gln Lys Glu Thr His Cys Pro Ala Asp Gly Pro Glu Gln
                995                1000                1005
Cys Glu Leu Val Gln Arg Pro Arg Tyr Arg Arg Gly Pro His Ile Cys
   1010                1015                1020
Phe Asp Tyr Asn Ala Thr Glu Asp Thr Ser Asp Cys Gly Arg Gly Ala
1025                1030                1035                1040
Ser Phe Pro Pro Ser Leu Gly Val Leu Val Ser Leu Gln Leu Leu Leu
                   1045                1050                1055
Leu Leu Gly Leu Pro Pro Arg Pro Gln Pro Gln Val Leu Val His Ala
               1060                1065                1070
Ser Arg Arg Leu
       1075

<210> SEQ ID NO 7
<211> LENGTH: 1070
<212> TYPE: DNA
<213> ORGANISM: Homo sapiens

<400> SEQUENCE: 7
cttaaagata gctagagcca cggggggctgt aagttcagca tgcctccttt tctggtctcc      60
gctgaagctg tcactccacc attaaacctg tgactctagg ccttaagcct gttgaaggtc     120
gagcccccaa aagggtcaca tatgctcctg ccttgggccg cggggcccgg gactcttccc     180
gcgggtgggg tggggaggag cggcagggtc tgaggtgtgg gggcggggc gcacccgggg     240 cgctcgggta gcagctgggg cgcaggacgc ccgagccagt agggcaggat tcgggctgcg     300
cggggacgag aggcgcgcgg gcacgggtgg gcgcgtggcc gcggcggggg cgcgcggggg     360
cgggccagcc cgggaagaga gagggaggga gggagagaag agggcggtgc cggcaggttg     420
gcggcggctg ctatttgagc gcaggtcccg ggccgggcgc tcagagcgct tggagccagc     480
gctgcaggga gatagcagcg cgcagcccgc agaggcgctg cggcccgtgc agccccggag     540
gcccctcgcg gagaaggcgg cggcggagga gaggccgagt taccgcccgc cgcccgcgcc     600
cccccaaccc cgccgccgcc gccgccgccg ccactgcccc ccctccccgc ggcgccgcat     660
cttgaatgga aacatggcgg tgccggctcg gacctgcggc gcctctcggc ccggcccagc     720
gcggactgcg cgcccctggc ccggctgcgg ccccacccct ggccccggca ccggcgcccc     780
gacgtccggg cccccgcgcc cgctgtggct gctgctgccg cttctaccgc tgctcgccgc     840
ccccggcgcc tctgcctaca gcttccccca gcagcacacg taagtggcct cggccggccg     900
cgagaccccg gccgagcctt gcgccccgct ctgccccccgg tccgcgctac tccttccctg     960
cgctccgcgc cagggcagag gcgctgggtc cggctgcccg ctgcgcccgg gggcgacggc    1020
cccaagcccc gaaggctggc agccgcggtc ccggcgctct ggctgcgtca                1070

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:   Synthetic

<400> SEQUENCE: 8
ctctacaacc caattcacca t                                                21
```

-continued

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 9
tagatggcac tggccttct                                                19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 10
actcaccacc ctactgttc                                                19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 11
agctgcctgt ttggtgcta                                                19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 12
ctgagagtga ggatgtggaa                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 13
gtgcatcctc atacacgttg                                               20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 14
gacaagccac cccttaccta c                                             21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic

```
<400> SEQUENCE: 15
gcagagccca gttctggctg                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 16
ccagcataga gtggtcagtg                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 17
agtaccctgt ccattgcctg                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 18
ggcaggtagc actgatggtc                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 19
ttggagccac tgagtggaag                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 20
gtggcttacg gtcctcactc                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 21
tgtgctggga gtcgcggctg                                               20

<210> SEQ ID NO 22
```

```
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 22
accactggac tgcctgcggt g                                                   21

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 23
cagggctggc agtgctacac                                                     20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 24
actgccagcc ctgtgaccat g                                                   21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 25
ccatctccag tccaggcatc                                                     20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 26
ttcgacagga cacagcccag                                                     20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 27
tgctgggtag acaggggaca g                                                   21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 28
```
agcccagtcg cctctgcaag                                                    20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 29
tggatacagc tggctgcgcc                                                    20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 30
ccttacccta acagaggcat c                                                  21

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 31
aacctcacgt gttctcctgc                                                    20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 32
tgggcaggag aacacgtgag                                                    20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 33
ctggtgatgg tcacaggagc                                                    20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 34
aggccactca ccaccctact g                                                  21

<210> SEQ ID NO 35
<211> LENGTH: 20
<212> TYPE: DNA

<213> ORGANISM: Artificial Sequence
<220> FEATURE:
<223> OTHER INFORMATION: Description of Artificial Sequence: Synthetic

<400> SEQUENCE: 35
tcctgggtac accaagccag                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 36
ggagggctga gagctgcctg                                              20

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 37
ttgaggttac tgctgtggcc ac                                           22

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 38
ctggtggcca cagcagtcac                                              20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 39
ggatggccag ttgaacatac g                                            21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 40
ttcgacagga cacagcccag                                              20

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 41
gtgctgggta gacaggggac agg                                          23

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 42
tgggcaggag aacacgtgag                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 43
ctggtgatgg tcacaggagc                                              20

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 44
acccctggct tctgcttcct t                                            21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 45
acactgccct catggtacag                                              20

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 46
acctccctgt gctctgtccc tca                                          23

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 47
aatccacgca tggatgggca                                              20

<210> SEQ ID NO 48
<211> LENGTH: 24
<212> TYPE: DNA
<213> ORGANISM: Artificial Sequence
<220> FEATURE:

<223> OTHER INFORMATION: Description of Artificial Sequence: Synthetic

<400> SEQUENCE: 48
tgagcagcta gtgctgaggc ctct                                              24

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 49
cagcaaggag gtgtggctca gga                                               23

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 50
actccaagca gtgtgagtgc                                                   20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 51
gaaggaagtt gttgcctgga a                                                 21

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 52
caggtgtgga aataagcagg                                                   20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 53
catcttcttg cagctccttg                                                   20

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 54
tgcccttgtt acagtcatct cca                                               23

```
<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 55
taagatgaaa agccagccag ctg                                            23

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 56
gtctcctctt tggacagatt ctg                                            23

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 57
tggagatgac tgtaacaagg gcac                                           24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 58
aagaggagac ttcccagtct cttg                                           24

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 59
ctgcatacag gatgcagcac tg                                             22

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 60
gctcacctca cggagctgct gcga                                           24

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
```

-continued

```
<400> SEQUENCE: 61
tgttcagccc agggaagcga agc                                              23

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 62
acttacagcc cccgtggctc tag                                              23

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 63
cctggctctg gaagaatcta                                                  20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 64
cagaaaagga ggcatgctga                                                  20

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 65
aagcgagtgg ctgcagag                                                    18

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 66
ctaagcggaa acctgggca                                                   19

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 67
gcatcttgaa tggaaacatg gc                                               22

<210> SEQ ID NO 68
<211> LENGTH: 18
```

```
<212> TYPE: DNA
<213> ORGANISM: Artificial Sequence
<220> FEATURE:
<223> OTHER INFORMATION: Description of Artificial Sequence: Synthetic

<400> SEQUENCE: 68
tcgacctcct gctccaga                                                 18

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 69
agcacacgat gcagcactg                                                19

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 70
cttctccacc aacttctgag                                               20

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 71
acaaccggaa cctgttcga                                                19

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 72
cgtcatagta cacgatgtct tc                                            22

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 73
atgctgcaga gaacttccag                                               20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 74
```

```
tgaagtttgg gtcctcgatg                                                    20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 75
ctgagagtga ggatgtggaa                                                    20

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 76
aagacctgcc acagcagtg                                                     19

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 77
gtgttcatgg aaaaccgcag                                                    20

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 78
ccactcacat ccacgatgat g                                                  21

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 79
ctgtacgatg tccgaaggag ac                                                 22

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 80
tgtgaagcat gacacaggct g                                                  21

<210> SEQ ID NO 81
<211> LENGTH: 20
<212> TYPE: DNA
<213> ORGANISM: Artificial Sequence
```

```
<220> FEATURE:
<223> OTHER INFORMATION: Description of Artificial Sequence: Synthetic

<400> SEQUENCE: 81
atctgtctgc gagatgctgg                                              20

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 82
ttctgcagct ggtcaaagg                                               19

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 83
cgcaacaaga aggtgttcaa g                                            21

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 84
gccccacgga gaaagtaaac                                              20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 85
tgttcacgga tggtggtgag                                              20

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 86
ttcctgtgtg ttgatgcgg                                               19

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 87
ttgagatccc ttccatcgg                                               19
```

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 88
gctggttctt cttttcccca g                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 89
gtggtaacag ggaccctccc t                                              21

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 90
agattggggt gcagcaacac                                                20

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 91
gctatgtgtt tgccattgac c                                              21

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 92
ctatgtacct ctcatccagg gac                                            23

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 93
catgattgat ggcaacaagg                                                20

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 94 gggagcagg aactcaaaat ac                22

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 95
gccaatctca gtgaccagat cc                22

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 96
aggttgtgca gaaggaagtt g                 21

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 97
agaaagtgac tccagactcc aag               23

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 98
ttgaagggct cagggttctc                   20

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 99
ggatctcaac acgtacagcc tac               23

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 100
ggatgcccac agtgtcattc                   20

<210> SEQ ID NO 101

```
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 101
cccttcaatg ccagcttcta c                                              21

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 102
aacttctcag cccaagcctc                                                20

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 103
aatgacactg tgggcatcct c                                              21

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 104
ttaacctcgc agtccatctc ac                                             22

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 105
accaagacca gcctcagaag tg                                             22

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 106
ataggactcc ttgcgggtgt ag                                             22

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 107
```
aggtggatgc caacctgatg                                                20

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 108
cgtagagaag ctgctggaac ag                                             22

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 109
caccgttgca gatttcctta ac                                             22

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 110
agtttccgca gtcgatgatg                                                20

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 111
gaaacagacc cagtactact tc                                             22

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 112
gcgttgtagt cgaagcagat                                                20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 113
agcagtgtga gctagtgcag                                                20

<210> SEQ ID NO 114
<211> LENGTH: 19
<212> TYPE: DNA

-continued

```
<213> ORGANISM: Artificial Sequence
<220> FEATURE:
<223> OTHER INFORMATION: Description of Artificial Sequence:  Synthetic

<400> SEQUENCE: 114
agggtgggaa aggcgaaga                                                       19
```

CALCIUM CHANNEL COMPOSITIONS AND METHODS OF USE THEREOF

This application claims priority benefit of U.S. provisional application No. 60/114,359 filed Dec. 30, 1998, the contents of which are hereby incorporated by reference.

The invention was made with Government support under CA 71618, P50-CA70907, N538691, and N01-00-56000, awarded by the National Cancer Institute and the National Institutes of Health. The Government has certain rights in the invention.

FIELD OF THE INVENTION

The present invention relates to calcium channel compositions and methods of making and using same. In particular, the invention relates to calcium channel alpha2delta ($\alpha_2\delta$) subunits and nucleic acid sequences encoding them. These compositions are useful in methods for identifying compounds that modulate the activity of calcium channels and for identifying compounds as therapeutic for disease.

BACKGROUND OF THE INVENTION

Calcium channels are present in various tissues, have a central role in regulating intracellular calcium ion concentrations, and are implicated in several vital processes in animals (e.g., neurotransmitter release, muscle contraction, pacemaker activity, secretion of hormones and other substances, etc.). Thus, changes in calcium influx into cells which are mediated through calcium channels have been implicated in various human diseases such as disorders of the central nervous system and cardiovascular disease.

For example, changes to calcium influx into neuronal cells may be implicated in conditions such as epilepsy, stroke, brain trauma, Alzheimer's disease, multiinfarct dementia, other classes of dementia, Korsakoff's disease, neuropathy caused by a viral infection of the brain or spinal cord (e.g., human immunodeficiency viruses, etc.), amyotrophic lateral sclerosis, convulsions, seizures, Huntington's disease, amnesia, or damage to the nervous system resulting from reduced oxygen supply, poison or other toxic substances (See e.g., Goldin et al., U.S. Pat. No. 5,312,928).

Additionally, changes to calcium influx into cardiovascular cells may be implicated in conditions such as cardiac arrhythmia, angina pectoris, hypoxic damage to the cardiovascular system, ischemic damage to the cardiovascular system, myocardial infarction, and congestive heart failure (Goldin et al., supra). Other pathological conditions associated with elevated intracellular free calcium levels include muscular dystrophy and hypertension (Steinhardt et al., U.S. Pat. No. 5,559,004). While there has been limited success in expressing DNA encoding rabbit and rat calcium channel subunits, little is known about human calcium channel structure, function and gene expression. Additionally, there is limited knowledge in the art of the role of calcium channel types in cell growth control and abnormalities of calcium channels leading to cancer development.

In addition to the implication of calcium channels in animal (including human) diseases, a number of compounds which are currently used for treating various cardiovascular diseases in animals (including humans) are believed to exert their beneficial effects by modulating the functions of voltage-dependent calcium channels present in cells, such as cardiac cells and vascular smooth muscle cells. Nonetheless, there is a paucity of understanding of the pharmacology of compounds which interact with calcium channels. This paucity of understanding, together with the limited knowledge in the art of the human calcium channel types, the molecular nature of the human calcium channel subtypes, and the limited availability of pure preparations of specific calcium channel subtypes to use for evaluating the efficacy of calcium channel-modulating compounds has hampered the rational testing and screening of compounds that interact with the specific subtypes of human calcium channels to have desired therapeutic effects.

SUMMARY OF THE INVENTION

The invention provides calcium channel alpha2delta ($\alpha_2\delta$) subunits, as well as amino and nucleic acids encoding them. In one embodiment, the invention provides a substantially purified nucleic acid sequence consisting of at least a portion of a nucleotide sequence selected from the group consisting of (a) SEQ ID NO:1, the complement thereof, variants thereof, and homologs thereof, (b) SEQ ID NO:3, the complement thereof, variants thereof, and homologs thereof, and (c) SEQ ID NO:5, the complement thereof, variants thereof, and homologs thereof. In a preferred embodiment, the nucleic acid sequence encodes at least a portion of the amino acid sequence selected from the group consisting of SEQ ID NO:2 and variants thereof, SEQ ID NO:4 and variants thereof, and SEQ ID NO:6 and variants thereof. In a more preferred embodiment, the nucleic acid sequence is double-stranded. In an alternative more preferred embodiment, the nucleic acid sequence is single-stranded.

Without intending to limit the nucleic acid sequences of the invention to any particular type of encoded protein, in an alternative preferred embodiment, the nucleic acid sequence encodes a fusion protein. While it is not contemplated that the invention be limited to the type or nature of fusion partner in the fusion protein, in a more preferred embodiment, the fusion protein comprises a polypeptide selected from the group consisting of chloramphenicol acetyltransferase, luciferase, beta-galactosidase, green fluorescent protein, Myc protein, protein A, glutathione-S-transferase, FLAG tag, and polyhistidine.

In another alternative preferred embodiment, the nucleic acid sequence is contained on a recombinant expression vector. In a more preferred embodiment, the expression vector is contained within a host cell. While it is not contemplated that the invention be limited to the type of host cell, in a yet more preferred embodiment, the host cell is eukaryotic. In an even more preferred embodiment, the eukaryotic cell is selected from the group consisting of cancer cells and amphibian oocytes.

Also provided by the invention is a substantially purified amino acid sequence comprising at least a portion of an amino acid sequence selected from the group consisting of SEQ ID NO:2 and variants thereof, SEQ ID NO:4 and variants thereof, and SEQ ID NO:6 and variants thereof. In a preferred embodiment, the portion is part of a fusion protein. While not intending to limit the invention to any particular type or nature of fusion protein, in a more preferred embodiment, the fusion protein comprises a polypeptide selected from the group consisting of chloramphenicol acetyltransferase, luciferase, beta-galactosidase, protein A, glutathione-S-transferase, FlAG tag, and polyhistidine.

The invention further provides substantially purified amino acid sequences encoded by at least a portion of a nucleotide sequence selected from the group consisting of (a) SEQ ID NO: 1, the complement thereof, variants thereof, and homologs thereof, (b) SEQ ID NO:3, the complement thereof, variants thereof, and homologs thereof, and (c) SEQ ID NO:5, the complement thereof, variants thereof, and homologs thereof.

The invention additionally provides methods for detecting presence of a nucleic acid sequence encoding at least a portion of a calcium channel protein, comprising: a) providing: i) a sample suspected of containing the nucleic acid sequence; and ii) at least a portion of a nucleotide sequence selected from the group consisting of (1) SEQ ID NO: 1, the complement thereof, variants thereof, and homologs thereof, (2) SEQ ID NO:3, the complement thereof, variants thereof, and homologs thereof, and (3) SEQ ID NO:5, the complement thereof, variants thereof, and homologs thereof, b) combining the sample with at least a portion of the nucleotide sequence under conditions such that the nucleic acid hybridizes with at least a portion of the nucleotide sequence; and c) detecting the hybridization. Although it is not contemplated that the invention be limited to the level of stringency of hybridization, in one preferred embodiment, the hybridization is under conditions of low stringency. In another preferred embodiment, the hybridization is under conditions of high stringency. Furthermore, it is contemplated that the invention will also be used in various assays to detect mRNA using these sequences (i.e., SEQ ID NOS:1, 3, and 5) including, but not limited to microassays.

The invention also provides methods for producing at least a portion of a calcium channel protein, comprising: a) providing: i) a recombinant expression vector comprising a nucleic acid sequence encoding at least a portion of an amino acid sequence selected from the group consisting of SEQ ID NO:2 and variants thereof, SEQ ID NO:4 and variants thereof, and SEQ ID NO:6 and variants thereof, and ii) a host cell; and b) introducing the vector into the host cell under conditions such that the host cell expresses the portion of the amino acid sequence. In one preferred embodiment, the method further comprises step c) recovering the expressed amino acid sequence (or portion thereof). While not intending to limit the invention to the type or nature of host cell, in an alternative preferred embodiment, the host cell is eukaryotic. In a more preferred embodiment, the eukaryotic host cell is selected from the group consisting of cancer cells and amphibian oocytes.

The invention also provides methods for screening test compounds for modulating calcium channel activity, comprising: a) providing: i) the test compound; ii) a calcium channel selective ion; iii) a control cell; and iv) a host cell comprising a cell membrane and expressing heterologous nucleic acid sequences encoding: 1) calcium channel $\alpha_1$ subunit; and 2) at least a portion of an amino acid sequence selected from the group consisting of SEQ ID NO:2 and variants thereof, SEQ ID NO:4 and variants thereof, and SEQ ID NO:6 and variants thereof; b) contacting the host cell with the test compound and with the molecule to produce a treated host cell; c) depolarizing the cell membrane of the treated host cell under conditions such that the molecule enters the cell through a functional calcium channel; and d) detecting a difference between current flowing into the treated host cell and current flowing into a control cell, thereby identifying the test compound as a compound capable of modulating calcium channel activity. In one preferred embodiment, the method further comprises, prior to the depolarizing, maintaining the treated host cell at a holding potential that substantially inactivates endogenous calcium channels. In another preferred embodiment, the method further comprises, prior to or simultaneously with the step of contacting the host cell with the test compound, contacting the host cell with a calcium channel agonist, wherein the test compound is tested for activity as an antagonist. In yet another preferred embodiment, the host cell further expresses calcium channel beta ($\beta$) subunit. In another preferred embodiment, the host cell further expresses calcium channel beta ($\beta$) subunit and gamma ($\gamma$) subunit. Without intending to limit the type or source of host cell, in yet another preferred embodiment, the host cell is eukaryotic. In a more preferred embodiment, the eukaryotic host cell is selected from the group consisting of cancer cells and amphibian oocytes.

Also provided herein is a method of generating antibodies directed against at least a portion of a calcium channel protein, comprising: a) providing: i) at least a portion of an amino acid sequence selected from the group consisting of SEQ ID NO:2 and variants thereof, SEQ ID NO:4 and variants thereof, and SEQ ID NO:6 and variants thereof; and ii) a host; b) immunizing the host with at least a portion of the amino acid sequence so as to generate an antibody; and c) collecting the antibody from the host. In one preferred embodiment, the method further comprises step d) purifying the antibody. Without limiting the type of host cell, in another preferred embodiment, the host is a mammal. In yet another preferred embodiment, the mammal is a mouse.

The invention further provides an antibody raised according to the method described in the preceding paragraph, i.e., by a) providing: i) at least a portion of an amino acid sequence selected from the group consisting of SEQ ID NO:2 and variants thereof, SEQ ID NO:4 and variants thereof, and SEQ ID NO:6 and variants thereof; and ii) a host; b) immunizing the host with at least a portion of the amino acid sequence so as to generate antibody; and c) collecting the antibody from the host. In one preferred embodiment, the antibody is monoclonal. In another preferred embodiment, the antibody is polyclonal. In still further embodiments, the present invention provides methods and compositions for genetic immunization for the production of antibodies (e.g., by injecting expression plasmid into an animal).

Also provided herein is an antibody which specifically binds to an amino acid sequence selected from the group consisting of SEQ ID NO:2 and variants thereof, SEQ ID NO:4 and variants thereof, and SEQ ID NO:6 and variants thereof. In a preferred embodiment, the antibody is monoclonal. In another preferred embodiment, the antibody is polyclonal.

The invention also provides a method of detecting expression of at least a portion of a calcium channel protein, comprising: a) providing: i) a sample suspected of expressing the calcium channel protein; and ii) an antibody raised according to the above-described method (i.e., by a) providing: i) at least a portion of an amino acid sequence selected from the group consisting of SEQ ID NO:2 and variants thereof, SEQ ID NO:4 and variants thereof, and SEQ ID NO:6 and variants thereof; and ii) a host; b) immunizing the host with at least a portion of the amino acid sequence so as to generate an antibody; and c) collecting the antibody from the host); b) combining the sample and the antibody under conditions such that the antibody binds to the calcium channel protein; and c) detecting the binding between the antibody and the calcium channel protein in the sample.

The present invention additionally provides methods for producing transgenic non-human animals, wherein the animal expresses a reduced level of calcium channel $\alpha_2\delta$ subunit relative to a corresponding wild-type animal, comprising: a) providing: i) an embryonic stem cell comprising wild-type calcium channel $\alpha_2\delta$-subunit genes; ii) a blastocyst of a non-human animal; iii) a pseudopregnant non-human animal; and iv) an oligonucleotide sequence comprising at least a portion of a non-human nucleotide sequence homologous to a nucleic acid sequence selected from the group consisting of (1) SEQ ID NO:1, complements thereof and variants thereof, (2) SEQ ID NO:3, complements thereof and variants thereof, and (3) SEQ ID NO:5, complements thereof and variants thereof; b) introducing the oligonucleotide sequence into the embryonic stem cell under conditions such that the oligonucleotide sequence is homologously recombined into at least one of the wild-type calcium channel $\alpha_2\delta$-subunit genes in the genome of the embryonic stem cell to produce a treated embryonic stem cell; c) injecting the treated embryonic stem cell into the blastocyst to produce an injected blastocyst; d) introducing the injected blastocyst into the pseudopregnant non-human animal; and e) permitting the pseudopregnant animal to deliver progeny comprising the homologously recombined oligonucleotide, wherein the progeny express a reduced level of calcium channel $\alpha_2\delta$-subunit relative to a corresponding wild-type animal. In one preferred embodiment, the transgenic non-human animal is selected from the order Rodentia. In a more preferred embodiment, the transgenic non-human animal is a mouse.

The invention also provides methods for producing transgenic non-human animals, wherein the animal expresses reduced activity of calcium channel $\alpha_2\delta$ subunit relative to a corresponding wild-type animal, comprising: a) providing: i) an embryonic stem cell comprising wild-type calcium channel $\alpha_2\delta$-subunit genes; ii) a blastocyst of a non-human animal; iii) a pseudopregnant non-human animal; and iv) an oligonucleotide sequence comprising at least a portion of a non-human nucleotide sequence homologous to a nucleic acid sequence selected from the group consisting of (1) SEQ ID NO:1, complements thereof and variants thereof, (2) SEQ ID NO:3, complement thereof and variants thereof, and (3) SEQ ID NO:5, complements thereof and variants thereof, wherein at least portion of the nucleotide sequence comprises one or more mutations selected from the group consisting of deletion, insertion and point mutation(s); b) introducing the oligonucleotide sequence into the embryonic stem cell under conditions such that the oligonucleotide sequence is homologously recombined into at least one of the wild-type calcium channel $\alpha_2\delta$-subunit genes in the genome of the embryonic stem cell to produce a treated embryonic stem cell; c) injecting the treated embryonic stem cell into the blastocyst to produce an injected blastocyst; d) introducing the injected blastocyst into the pseudopregnant non-human animal; and e) permitting the pseudopregnant animal to deliver progeny comprising the homologously recombined oligonucleotide, wherein the progeny express reduced activity of calcium channel $\alpha_2\delta$-subunit relative to a corresponding wild-type animal. In one preferred embodiment, the transgenic non-human animal is selected from the order Rodentia. In a more preferred embodiment, the transgenic non-human animal is a mouse.

Additionally provided herein is a method for identifying a therapeutic compound, comprising: a) providing: i) a transgenic non-human animal produced by the method described in either of the previous two paragraphs; and ii) a composition comprising the compound; and b) administering the compound to the transgenic non-human animal to produce a treated animal. While it is not intended that the transgenic animal be limited to a particular type, in one preferred embodiment, the transgenic animal has cancer. In a more preferred embodiment, the cancer is selected from the group consisting of lung cancer, breast cancer, nasopharyngeal cancer, cervical cancer, head cancer and neck cancer. In yet a more preferred embodiment, the lung cancer is selected from the group consisting of small cell carcinoma and non small cell carcinoma. In another preferred embodiment, the transgenic animal has a neurological disease selected from the group consisting of epilepsy, stroke, brain trauma, Alzheimer's disease, multiinfarct dementia, amyotrophic lateral sclerosis, convulsions, seizures, Huntington's disease, and amnesia. In yet another preferred embodiment, the transgenic animal has a cardiovascular disease selected from the group consisting of cardiac arrhythmia, angina pectoris, hypoxic damage to the cardiovascular system, ischemic damage to the cardiovascular system, myocardial infarction, and congestive heart failure. In a further preferred embodiment, the transgenic animal has Lambert-Eton myasthenic syndrome.

In still further embodiments, the present invention provides methods for treatment of human tumors in non-human animals. For example, it is contemplated that the methods for identifying therapeutic compounds as described herein will find use in the treatment of human tumors in immunodeficient mice (e.g., nude and/or SCID [severe combined immunodeficiency] mice) or other animals.

BRIEF DESCRIPTION OF THE DRAWINGS

FIG. 3(A–C) provides Western blot data from transcription and translation experiments. Panel A provides results from in vitro transcription and translation of $\alpha_2\delta$ in expression vector pcDNA3.1 and a control sample. Panel B provides results for transfection of NCI-H1299 cells with $\alpha_2\delta$-2 and a control.

DEFINITIONS

Figures 1, 1A:
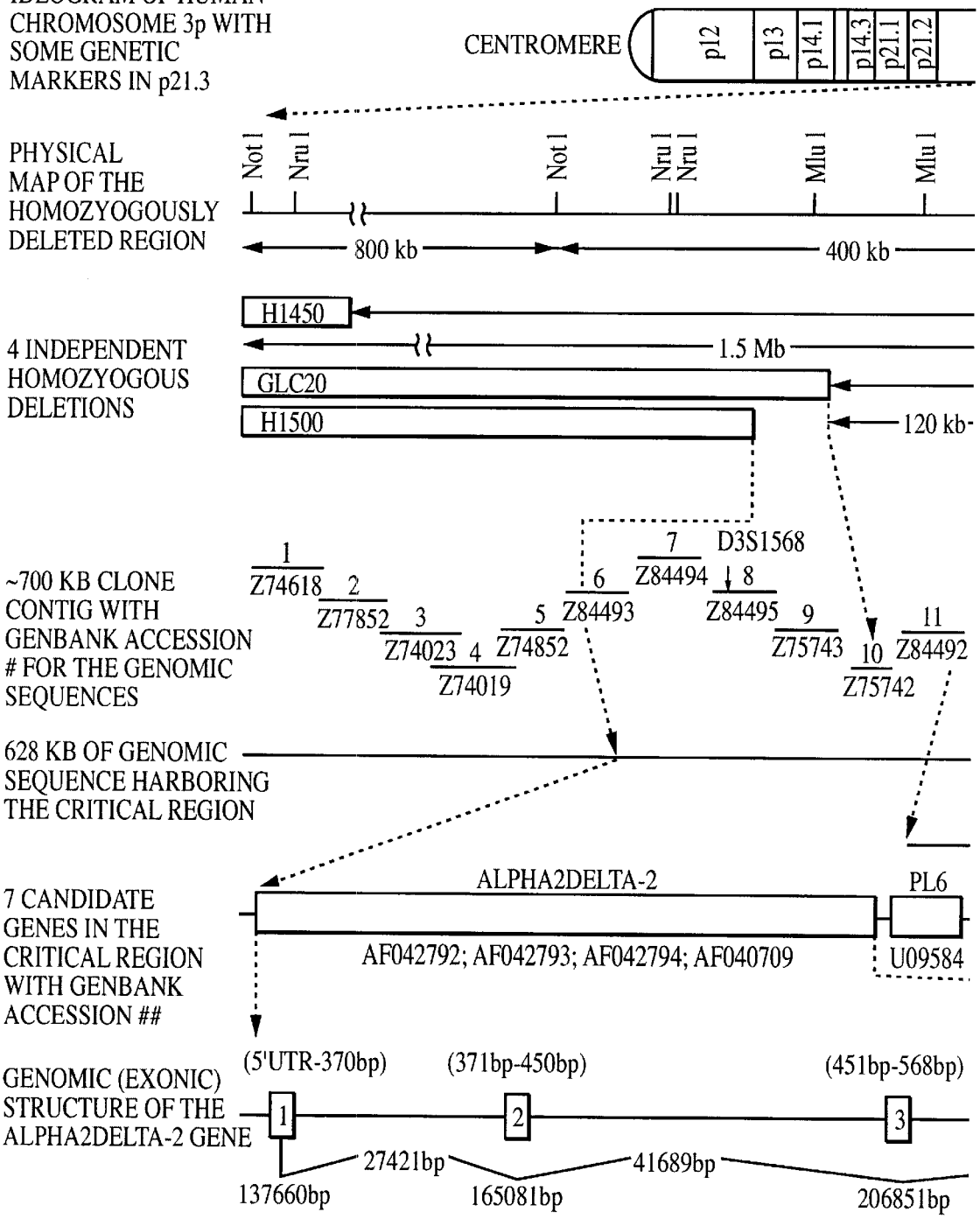
FIG. 1 (A–B) provides a schematic outline of the positional cloning of the $\alpha_2\delta$ gene in lung cancer critical region on the short arm of human chromosome region 3p21.3.
Figure 1B:
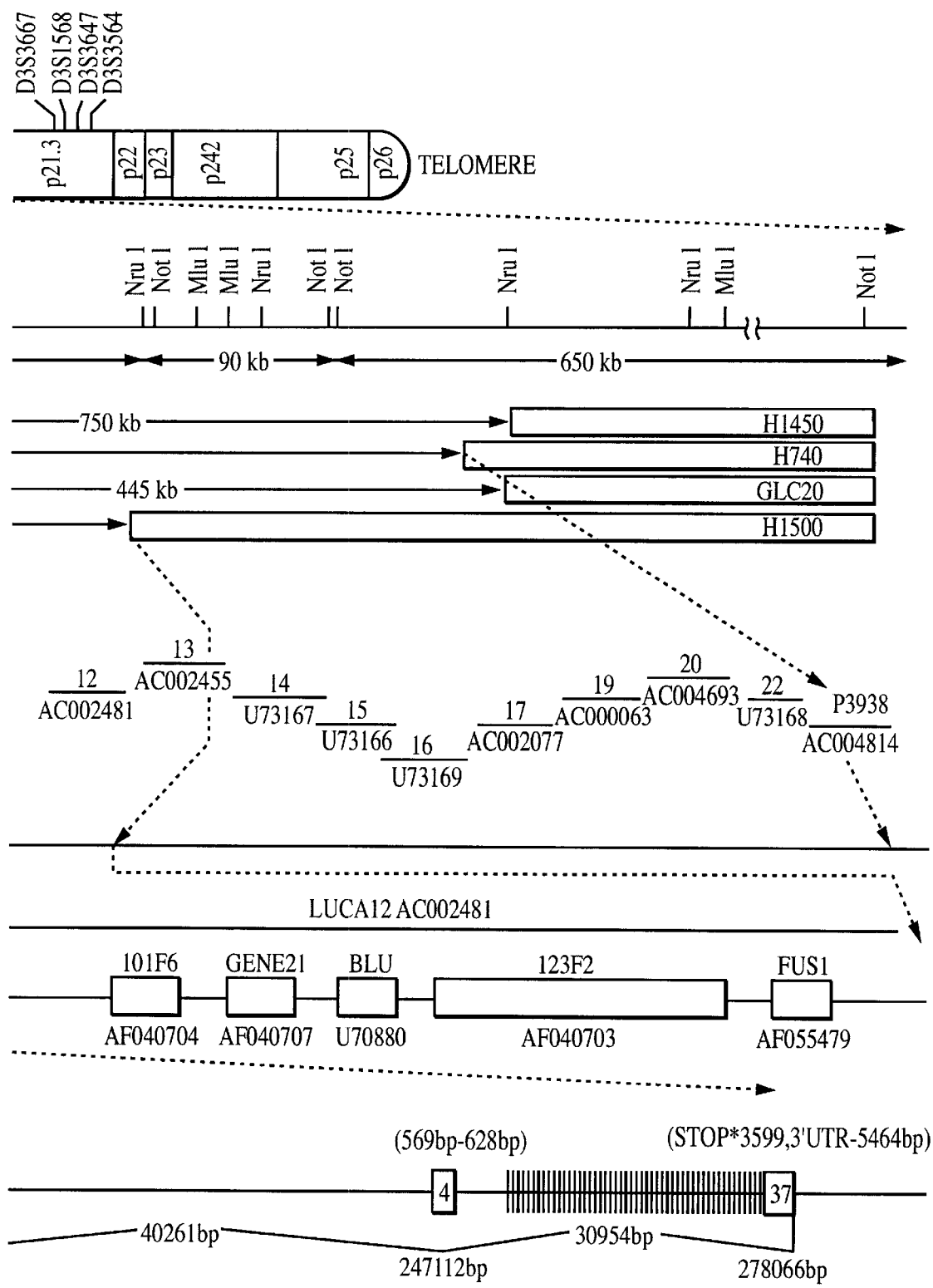

To facilitate an understanding of the invention, a number of terms are defined below.

As used herein the term "portion" when made in reference to a nucleic acid sequence refers to a fragment of that sequence. The fragment may range in size from five (5) contiguous nucleotide residues to the entire nucleic acid sequence minus one nucleic acid residue. Thus, "a nucleic acid sequence comprising at least a portion of a nucleotide sequence" comprises from (5) contiguous nucleotide residues of the nucleotide sequence to the entire nucleotide sequence.

The term "portion" when used in reference to a protein (as in a "portion of a given protein") refers to fragments of that protein. The fragments may range in size from four (4) contiguous amino acid residues to the entire amino acid sequence minus one amino acid residue. Thus, a polypeptide sequence comprising "at least a portion of an amino acid sequence" comprises from four (4) contiguous amino acid residues of the amino acid sequence to the entire amino acid sequence.

As used herein, the term "purified" or "to purify" refers to the removal of undesired components from a sample. For example, where recombinant $\alpha_2\delta$ polypeptides are expressed in eukaryotic host cells, the $\alpha_2\delta$ polypeptides are purified by the removal of host cell proteins thereby increasing the percent of recombinant $\alpha_2\delta$ polypeptides in the sample.

As used herein, the term "substantially purified" refers to molecules, either nucleic or amino acid sequences, that are removed from their natural environment such that they are at least 60% free, preferably 75% free, and more preferably 90% free from other components with which they are naturally associated.

The term "recombinant DNA molecule" as used herein refers to a DNA molecule which is comprised of segments of DNA joined together by means of molecular biological techniques. The term "recombinant protein" or "recombinant polypeptide" as used herein refers to a protein molecule which is expressed using a recombinant DNA molecule. A "recombinant calcium channel" protein refers to a calcium channel that contains one or more recombinant calcium channel subunits or one or more recombinant portions of at least one calcium channel subunit.

The term "oligonucleotide" as used herein is defined as a molecule containing from two (2) to one hundred (100), preferably from ten (10) to fifty (50), and more preferably from twenty (20) to thirty (30) deoxyribonucleotides or ribonucleotides. Oligonucleotides may be generated by several methods known in the art including, but not limited to, chemical synthesis, DNA replication, reverse transcription, restriction digestion, polymerase chain reaction, and the like.

The term "transfection" as used herein refers to the introduction of a transgene into a cell. The term "transgene" as used herein refers to any nucleic acid sequence which is introduced into the genome of a cell by experimental manipulations (e.g., using methods including, but not limited to recombinant cloning). A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

Transfection may be stable or transient. The term "stable transfection" or "stably transfected" refers to the introduction and integration of a transgene into the genome of the transfected cell. The term "stable transfectant" refers to a cell which has stably integrated one or more transgenes into the genomic DNA. The term "transient transfection" or "transiently transfected" refers to the introduction of one or more transgenes into a transfected cell in the absence of integration of the transgene into the host cell's genome. The term "transient transfectant" refers to a cell which has transiently integrated one or more transgenes.

The term "foreign gene" refers to any nucleic acid (e.g., gene sequence) which is introduced into the genome of an animal by experimental manipulations and may include gene sequences found in that animal so long as the introduced gene contains some modification (e.g., a point mutation, the presence of a selectable marker gene, etc.) relative to the naturally-occurring gene.

The term "gene" refers to a DNA sequence that comprises control and coding sequences necessary for the production of RNA or a polypeptide. The polypeptide can be encoded by a full length coding sequence or by any portion of the coding sequence.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

A "variant" of a nucleic acid sequence is defined as a nucleotide sequence which differs from the nucleic acid sequence (e.g., by having deletions, insertions, and substitutions) that may be detected using hybridization assays or sequencing.

A "variant" of a polypeptide sequence is defined as an amino acid sequence which differs by one or more amino acids from the polypeptide sequence. The variant may have "conservative" changes, wherein a substituted amino acid has similar structural or chemical properties (e.g., replacement of leucine with isoleucine). More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software.

A nucleic acid sequence which is a "homolog" of a $\alpha_2\delta$ nucleic acids sequence (e.g., SEQ ID NOs: 1, 3, and 5) is defined herein as a nucleic acid sequence which exhibits more than 56%, more preferably at least 70%, and most preferably at least 95% identity to the $\alpha_2\delta$ nucleic acid sequence. Alternatively, a homolog of a $\alpha_2\delta$ nucleic acid sequence (e.g., SEQ ID NOs: 1, 3, and 5) is defined as a nucleic acid sequence which encodes a biologically active $\alpha_2\delta$ subunit polypeptide.

The term "substantially homologous" when used in reference to a double-stranded nucleic acid sequence such as a cDNA or genomic clone refers to any nucleic acid sequence which is capable of hybridizing to either or both strands of the double-stranded nucleic acid sequence of interest under conditions of low stringency.

Low stringency conditions when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5×Denhardt's reagent [50×Denhardt's contains the following per 500 ml: 5 g Ficoll (Type 400, Pharmacia), 5 g BSA (Fraction V; Sigma)] and 100 $\mu$g/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SDS, 5×Denhardt's reagent and 100 $\mu$g/ml denatured salmon sperm DNA followed by washing in a solution comprising 0.1×SSPE, 1.0% SDS at 42° C. when a probe of about 500 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 50% to 70% homology to the first nucleic acid sequence, then another hybridization condition is the to be equivalent to the hybridization condition of interest if this other hybridization condition also results in hybridization of the first nucleic acid sequence with the other nucleic acid sequences that have from 50% to 70% homology to the first nucleic acid sequence.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

The term "hybridization" as used herein includes "any process by which a strand of nucleic acid joins with a complementary strand through base pairing." (See e.g., J. Coombs, *Dictionary of Biotechnology,* Stockton Press, New York N.Y. [1994]). Hybridization and the strength of hybridization (i.e., the strength of the association between the nucleic acids) is impacted by such factors as the degree of complementarity between the nucleic acids, stringency of the conditions involved, the T$_m$ of the formed hybrid, and the G:C ratio within the nucleic acids.

The terms "alpha2delta," "$\alpha_2\delta$," "alpha2delta subunit," "$\alpha_2\delta$ subunit" when made in reference to a polypeptide sequence are used interchangeably to refer to a calcium channel subunit type. The $\alpha_2\delta$ subunit type comprises subunit subtypes, also referred to as subunit isoforms (e.g., isoforms I and II disclosed herein), which arise as a result of translation of splice variants of the primary transcript of the $\alpha_2\delta$ gene.

As used herein, a "splice variant" refers to an RNA sequence produced by processing of a primary transcript (i.e., pre-mRNA) of a genomic DNA sequence. Pre-mRNAs (also referred to as heterogenous nuclear RNA or hnRNA) in higher eukaryotes contain multiple introns which must be precisely excised by RNA splicing prior to transport over the nuclear membranae into the cytoplasm for translation. Differential processing of the primary transcript results in more than one RNA sequence, wherein each RNA sequence is referred to as a splice variant of the primary DNA transcript. Splice variants may occur within a single tissue type or among different tissues (e.g., neuronal tissue, muscle tissue, etc.) Splice variants which occur among different tissues are referred to as "tissue specific variants."

The term "calcium channel selective ion" is an ion that is capable of entering, or of being blocked from entering, a cell through a calcium channel which spans a cellular membrane under conditions which would permit or block the entry of calcium ions (Ca$^{++}$) into the cell. Calcium channel selective ions are exemplified, but not limited to, Ca$^{++}$ (calcium ions) and Ba$^{++}$ (barium ions).

A "calcium channel" as used herein refers to a peptide sequence comprising at least alpha 1 ($\alpha_1$) subunit. More preferably, a calcium channel further comprises alpha 2 ($\alpha_2$), beta ($\beta$), gamma ($\gamma$) and delta ($\delta$) subunits. The nucleic acid and amino acid sequences of calcium channel subunits in different organisms (e.g., human, rabbit, and rat) and in different tissues of the same organism (e.g., neuronal tissue, cardiovascular tissue) are known in the art (See e.g., Ellis et al., Science 241(4873):1661–4 [1988]; Williams et al., Neuron 8(1):71–84 [1992]; Ellis et al. U.S. Pat. No. 5,686,241 hereby incorporated by reference; and Harpold et al., U.S. Pat. No. 5,792,846 hereby incorporated by reference).

The terms "functional calcium channel" and "biologically active calcium channel" interchangeably refer to a calcium channel which allows entry into a cell of a calcium channel selective ion in response to a stimulus. Such entry may be determined by measuring the amount of current which flows through the calcium channel in response to the stimulus. Alternatively, a functional calcium channel refers to a calcium channel which binds ligands that have affinity for a calcium channel. For ligand binding assays of a recombinant calcium channel, it is preferred that the host cell which is used for testing the function of the recombinant calcium channel not produce endogenous calcium channel subunits that are of a type or in an amount that interferes with the detection of the recombinant calcium channel. Methods for determining the function of a calcium channel are known in the art, such as those described in Harpold et al., supra.

The terms "functional calcium channel subunit" and "biologically active calcium channel subunit" are equivalent terms which refer to a calcium channel subunit which is capable of associating with at least one other calcium channel subunit to form a functional calcium channel.

The term "compound that modulates calcium channel activity" and grammatical equivalents thereof refers to a compound that alters (i.e., reduces or increases) the ability of a calcium channel to pass calcium channel selective ions as measured by, for example, the current flowing through the calcium channel. Such compounds include, but are not limited to, calcium channel agonists (e.g., Goldin et al., U.S. Pat. No. 5,312,928, herein incorporated by reference) and antagonists, and compounds that exert their effect on the activity of the calcium channel directly or indirectly.

The term "agonist" refers to a molecule which, when interacting with a biologically active molecule, causes an enhancement in the activity of the biologically active molecule. Agonists may include proteins, nucleic acids, carbohydrates, or any other molecules which bind and/or interact with biologically active molecules. For example, an agonist can alter the activity of gene transcription by interacting with RNA polymerase directly, or through a transcription factor.

The terms "antagonist" or "inhibitor" refer to molecules which, when interacting with a biologically active molecule, block or inhibit the biological activity of the biologically active molecule. Antagonists and inhibitors may include proteins, nucleic acids, carbohydrates, or any other molecules which bind and/or interact with biologically active molecules. Inhibitors and antagonists can affect the biology of entire cells, organs, or organisms (e.g., an inhibitor that slows tumor growth).

The term "modulate" refers to a change or an alteration in the biological activity of a biologically active molecule. Modulation may be an increase or a decrease in activity, a change in binding characteristics, or any other change in the biological, functional, and/or immunological properties of biologically active molecules.

The term "biologically active" refers to molecules, compounds, etc., with structural, regulatory, and/or biochemical functions in an organism, cell, and/or organ.

A "non-human animal" refers to any animal which is not a human and includes vertebrates such as rodents, non-human primates, ovines, bovines, ruminants, lagomorphs, porcines, caprines, equines, canines, felines, aves, etc. Preferred non-human animals are selected from the order Rodentia.

The term "order Rodentia" refers to rodents (i.e., placental mammals in the Class Euthria, which also include the family Muridae (e.g., rats and mice)), most preferably mice.

A "transgenic animal" as used herein refers to an animal that includes a transgene which is inserted into an embryonal cell and which becomes integrated into the genome either of somatic and/or germ line cells of the animal which develops from that embryonal cell, or of an offspring of such an animal.

As used herein, the term "therapeutic" when made in reference to a compound refers to a compound which is capable of reducing, delaying, or eliminating one or more undesirable pathologic effects in a subject.

DESCRIPTION OF THE INVENTION

The invention provides nucleic acid sequences encoding calcium channel $\alpha_2\delta$ subunits. In particular, the invention provides cDNA sequences which are derived from splice variants of the calcium channel $\alpha_2\delta$ gene and which encode $\alpha_2\delta$ protein isoforms (e.g., isoforms I and II). Also provided herein are polypeptide sequences of calcium channel $\alpha_2\delta$ subunit isoforms. The compositions of the invention are useful in the detection, prevention and treatment of diseases such as cancer, autoimmune, cardiovascular, and neurological diseases. The compositions provided herein are also useful for the generation of in vitro and in vivo animal models for diseases (e.g., cancer, autoimmune, cardiovascular and neurological diseases) which in turn may be used to screen compounds for their therapeutic effects on these diseases.

The nucleic acids of the invention were discovered during a search by the inventors for a lung cancer and breast cancer tumor suppressor gene in the chromosome region 3p21.3, which the inventors considered to be one of the earliest regions undergoing genetic change in the smoking damaged bronchial epithelium and to thus to be associated with the development of lung and breast cancers. Furthermore, frequent allele loss and occasional homozygous deletions have been found in lung, breast, other human tumors (Wei et al., Cancer Res., 56(7):1487–1992 [1996]). As the lung cancer epidemic kills annually 150,000 victims in the USA, more deaths than due to colon, prostate, and breast cancer combined, much research has been conducted in the area of lung cancer diagnosis, prognosis, treatment, and prevention. The magnitude of this epidemic has heightened efforts to discover the genetic origin of lung cancer. While tobacco smoking is a well-established environmental trigger in lung carcinogenesis, the art's understanding of the genetic etiology of lung cancer is still incomplete.

Based on evidence from genetic mapping studies including overlapping homozygous deletions, it was the inventors' consideration that a tumor suppressor gene was located in the chromosome 3p21.3 band. To this end, the present inventors constructed a ~700 kb long clone contig (i.e., a continuous sequence of DNA that has been assembled from overlapping cloned DNA fragments) covering the lung cancer region in 3p21.3 and isolated a number of genes residing on the contig (Wei et al., Cancer Res., 6(7):1487–92 [1996]). This 700 kb segment has been sequenced jointly by the Washington University Sequencing Center (Saint Louis, Mo.) and the Sanger Sequencing Centre (Hixton, UK) (See, web sites: http://www.sanger.ac.uk/ and http://genome.wustl.edu/gsc/gschmpg.html). The inventors used this sequence as a tool to detect and clone more genes from the region by in silico initiated methods. In addition, by discovering and mapping a new overlapping homozygous deletion in the region, the inventors narrowed the critical area to approximately 120 kb, thus limiting the search for the lung and breast cancer gene to a set of eight resident genes. One of these genes was identified by the inventors using bioinformatics methods as a new calcium channel $\alpha_2\delta$ subunit gene. It was surprising that the new calcium channel $\alpha_2\delta$ subunit gene was identified by the inventors to be located in a region of this contig that was different from the region which was reported in the art to contain the sought-after lung cancer tumor suppressor gene.

Importantly, the present inventors also discovered that expression of the $\alpha_2\delta$ subunit was shut off in a majority of lung cancer cells. This indicated to the inventors that an alteration in calcium homeostasis in cancer cells leads to malignancy. Sequence analysis of the $\alpha_2\delta$ gene and deduced protein identified this gene as a new calcium channel $\alpha_2\delta$ subunit gene.

The $\alpha_2\delta$ subunit gene disclosed herein is located in the lung cancer critical region on 3p21.3, is about 140 kb long, contains at least 37 exons, and encodes at least three differentially spliced mRNA isoforms of about 5.3–5.5 kb in length differing at their 5' ends. Data disclosed herein reveals that, by Northern analysis, the $\alpha_2\delta$ subunits are highly expressed in lung and testis, moderately expressed in brain, heart, skeletal muscle, pancreas, small intestine, ovary, and spleen, with low levels of expression in kidney, and undetectable levels of expression in liver, thymus, and colon.

The tissue distribution of mRNA for the three $\alpha_2\delta$ subunits is very different (Klugbauer et al., J. Neurosci., 19(2):684–691 [1999]; and Angelotti and Hofmann, supra). All three genes are expressed in brain, which is the only tissue that expresses $\alpha_2\delta$-3. The $\alpha_2\delta$-1 gene is highly expressed in skeletal muscle, where little or no expression of $\alpha_2\delta$-2 was found. Both $\alpha_2\delta$-1 and -2 are expressed in heart. The $\alpha_2\delta$-2 gene is highly expressed in lung where the expression of $\alpha_2\delta$-1 is low. It is contemplated that the present invention will be used to determine which cells in the lung express $\alpha_2\delta$-2. In fact, the present inventors have shown that several lung cancers representing different lung epithelial types can express $\alpha_2\delta$-2. Thus, it is contemplated that some normal lung epithelial cells also express $\alpha_2\delta$-2. In this regard, it is also interesting to note that $\alpha$1C was cloned from lung cDNA libraries (Biel et al., FEBS Lett., 269(2):409–412 [1990]), and L-type currents have been characterized from tracheal smooth muscle (Welling et al,. Am. J. Physiol., 262(3 Pt 1):L351–359 [1992]). The only $\beta$ subunit detected in lung mRNA is $\beta_2$ (Castellano and Perez-Reyes, Biochem. Soc. Trans., 22(2):483–488 [1994]). Therefore, the minimum subunit composition of lung L-type channels can be deduced as $\alpha$1C$\alpha_2\delta$-2$\beta_2$.

It was noted that the results obtained during the development of the present invention do not agree with those of Klugbauer et al. (Klugbauer et al., supra), who found abundant cross-reactive material from what they reported to be $\alpha_2\delta$-2, in mRNA from skeletal muscle, pancreas, and heart, with hardly any signal from lung (Klugbauer et al., supra). It is believed that the expression pattern described herein is the correct one for $\alpha_2\delta$-2, since the probes used for Northern blotting were derived from the whole coding region of $\alpha_2\delta$-2, while authors of the Klugbauer report used only a 356 nucleotide probe from the coding region. In addition, the results of tissue expression pattern in independent Northern blot experiments were confirmed using two additional different short CACNA2D2 probes. The result of the cDNA screening also supports the high expression of $\alpha_2\delta$-2 in lung, as 120 $\alpha_2\delta$-2 clones were obtained from a screening of 1 million clones of a lung cDNA library. A possible explanation for the discrepancy could be that Klugbauer et al.'s probe cross-reacted with $\alpha_2\delta$-1, since it has an expression pattern very similar to what they reported for $\alpha_2\delta$-2 (Angelotti and Hofmann, FEBS Lett., 397(2–3):331–337 [1996]). Furthermore, it is unlikely that $\alpha_2\delta$ -2 is highly expressed in skeletal muscle, because $\alpha_2\delta$ proteins were purified from that tissue and only the sequence of $\alpha_2\delta$-1 was detected (Ellis et al., Science 214(4873):1661–1663 [1988]).

The function of the gene product of the new $\alpha_2\delta$-2 gene was tested in Xenopus oocytes by co-expressing $\alpha_2\delta$-2 cRNAs along with a representative member of the three families of calcium subunit $\alpha$1 subunits. In these experiments, three $\alpha$1 subunits were investigated for their effect on currents. The $\alpha$1 subunits were chosen to represent each of the three subfamilies of $Ca^{2+}$ channels: $Ca_v1.2$ or $\alpha$1C, $Ca_v2.2$ or $\alpha$1B, and an LVA channel $Ca_v3.1$ or $\alpha$1G. In each case, $\alpha_2\delta$-2 was able to stimulate functional expression. No effect was observed on the biophysical properties of the current, suggesting that $\alpha_2\delta$-2 simply increased the number of functional channels at the plasma membrane. Similar results were obtained with $\alpha_2\delta$-1 on the expression of $\alpha$1G in both COS cells and Xenopus oocytes (Dolphin et al., J. Physiol., 519.1:35–45 [1999]). Surprisingly, a pattern of expression was identified that was different from the other $\alpha_2\delta$ subunit, and $\alpha_2\delta$-2 was found to enhance the activity of the calcium $\alpha$1 subunits.

Co-expression studies of $\alpha_2\delta$-2 plus $\alpha$1B also included the $\beta_3$ subunit. In these experiments, the largest stimulatory effect on expression was observed. Some studies have reported a synergistic action of $\alpha_2$ and $\beta$ on $\alpha$1B expression (See e.g., Brust et al., Neuropharmacol., 32(11:1089–1102 [1993]). The experiments with $\alpha$1C did not include a $\beta$ subunit because they stimulate current so much already that it has been difficult to see any effect of $\alpha_2\delta$ at the whole cell level (Wei et al., J. Biol. Chem., 270(45):27106–27111 [1995]).

The invention discloses that the $\alpha_2\delta$ subunit gene is a candidate tumor suppressor gene which is involved in the origin of cancers (e.g., lung cancer, breast cancer, etc.). Indeed, interest in the physiological roles of $Ca^{2+}$ channels has increased, due to finding that mutations in their genes can lead to human diseases (Lehmann-Horn and Jurkatt-Roth, Physiol. Rev., 79:1317–1372 [1997]). In addition to potential role(s) in cancer pathogenesis, defects in the auxiliary subunits of $Ca^{2+}$ channels have been described in mouse models of absence epilepsy. These include mouse strains that have lost the expression of $\beta_4$, and the recently discovered $\gamma_2$ subunit (Letts et al., Nat. Genet., 19:340–347 [1998]; and Burgess et al., Cell 88:385–392 [1997]). In this regard after CACNA2D2 was cloned, it was noted with great interest that the syntenic region in the mouse (mouse chromosome 9, 59.0–60.0 cM, http://www.informatics.jax.org/) contains the mouse mutant ducky and also 5 other flanking genes (CISH, GNAI2, GNAT, and HYAL1) that were identified in the ~600 kb region (Wei et al., Cancer Res., 56(7):1487–1492 [1996]; and GenBank deposits AF132297 for CISH and U03056 for HYAL1). The partial mouse cDNA sequence was found to be 92% identical to the human $\alpha_2\delta$-2 sequence (GenBank #AF169633.1). Indeed, preliminary evidence suggests that loss of $\alpha_2\delta$-2 expression leads to the epileptic phenotype, ducky (Barclay et al., Epilepsia 40(Suppl. 2):137 [1990]). Histological examination of mouse ducky mutants reveals atrophy of the cerebellum, medulla oblongata, and spinal cord (Meier, Acta Neurol., 11:15–28 [1968]). These mice develop a spike-and-wave phenotype in the electroencephalogram, which is similar to that observed in absence epilepsy patients. Thus, it is contemplated that the present invention will find use in the development of methods to identify and test for the presence of inherited defects in CACNA2D2 in other species, including humans. It is also contemplated that the present invention will find use in assessing calcium channel defects associated with epileptic and other pathological phenotypes.

The invention further discloses that biallelic inactivation (i.e., inactivation of two alleles leading to complete loss-of-function) or monoallelic inactivation (i.e., inactivation of one allele leading to haploinsufficiency) of the $\alpha_2\delta$ subunit gene represents the critical rate-limiting step in the development of cancer. Thus, it is clear that the present inventors' discovery of a novel $\alpha_2\delta$ subunit of calcium channels provides compositions which are useful in the detection, prevention and treatment of cancer, as well as other diseases (e.g., epilepsy, migraine, episodic ataxia, stroke, brain trauma, Alzheimer's disease, multiinfarct dementia, Korsakoff's disease, amyotrophic lateral sclerosis, convulsions, seizures, Huntington's disease, amnesia, cardiac arrhythmia, angina pectoris, hypoxic damage to the cardiovascular system, ischemic damage to the cardiovascular system, myocardial infarction, congestive heart failure, muscular dystrophy, hypertension, etc.) which implicate calcium channels.

In addition, the present inventors have also discovered that the $\alpha_2\delta$ subunit gene is involved in lung carcinogenesis based on their observation of reduced levels of expression of the $\alpha_2\delta$ subunit gene in lung cancer (e.g., small cell lung cancer and non-small cell lung cancer) cell lines as compared to normal lung cells. The present inventors have also discovered that the $\alpha_2\delta$ subunit gene is implicated in breast carcinogenesis based on a homozygous deletion of the gene in a breast cancer cell line and in its primary tumor.

Furthermore, a clinical connection between voltage dependent calcium channels and lung cancer is well established by the Lambert-Eaton myasthenic syndrome (LEMS) seen in some small cell lung cancer patients (Takamori, Intern. Med., 38(2):86–96 [1999]). LEMS is a human autoimmune disorder that impairs neuromuscular transmission such that patients with this syndrome have a defect in the $Ca^{2+}$ dependent quantal release of acetylcholine from motor nerve terminals (O'Neill et all., Brain 111(Pt. 3):577–596 [1988]). In this syndrome, patients develop antibodies (presumably initiated by expression of the channel proteins in their small cell lung cancer) that react with voltage-gated calcium channel polypeptides which block depolarization-induced $Ca^{2+}$ influx leading to the myasthenia (Lennon et al., New Engl. J. Med., 332(22):146701474 [1995]; Raymond et al., Neurosci., 90(1):269–277 [1999]; and Voltz et al., Muscle Nerve 22(l):119–122 [1999]). During the development of the present invention the ability of $\alpha_2\delta$-2 to functionally interact with the T-type channel subunit $\alpha$1G was observed. In addition, Toyota et al. reported that CACNA1G encoding this subunit could have its expression inactivated by aberrant methylation of its 5' CpG island in human tumors such as colorectal cancers, gastric cancers, and acute myelogenous leukemias (Toyota et al., Cancer Res., 59(18):4535–4541 [1999]). CACNA1G maps to chromosome region 17q21 another site of frequent allele loss in human cancer. Such acquired CpG island methylation in promoter regions of cancer cells as an acquired abnormality silencing genes such as tumor suppressor genes has been described (Baylin et al., Adv. Cancer Res., 72:141–196 [1998]; and Schmutte and Jones, Biol. Chem., 379(4–5):377–388 [1998]).

Furthermore, calcium influx via voltage-gated calcium channels including T-type channels and intracellular calcium signaling plays a role in apoptosis (Berridge et al., Nature 395(6703):645–648 [1998]). In addition, platelet derived growth factor stimulated calcium influx changed during transformation of mouse C3H 10T1/2 fibroblasts accompanied by a marked reduction in expression of T-type calcium channels (Estacion and Mordan, Cell Signal 9(5):363–366 [1997]). Thus, it is contemplated that the present invention will find use in investigations regarding the inactivation of voltage gated calcium channel subunits such as CACNA2D2 and CACNA1G by any of several means (e.g., in investigations pertaining to such areas as cancer pathogenesis)..

The invention is further described under (A) Calcium channel types and subtypes, (B) Using probes to identify and isolate DNA encoding $\alpha_2\delta$ calcium channel peptides, (C) Using primers to amplify splice variant RNAs encoding $\alpha_2\delta$ calcium channel peptides, (D) Using nucleic acid sequences for gene therapy, (E) Generation of calcium channel $\alpha_2\delta$ subunit peptides, (F) Generation of antibodies directed to $\alpha_2\delta$ calcium channel peptides, (G) Screening compounds that modulate the activity of $\alpha_2\delta$ calcium channel peptides, (H) in vitro and in vivo suppression of tumor cell growth, and (I) Generating transgenic animals expressing reduced levels of $\alpha_2\delta$ calcium channel peptides.

A. Calcium Channel Types and Subtypes

Living cells of all biological orders are uniquely equipped with an impressive number and variety of calcium channels and pumps that are involved in maintaining calcium homeostasis within cells, tissues, and whole organisms (McEnery (Ed) J. Bioenerg. Biomembr., 30(4): 297–418 [1998]). Changes in the concentration of intracellular calcium is the central focus of many signaling networks within cells that converge to bring about changes in gene expression in response to cellular and extracellular cues to control a diverse range of cell functions (McEnery, supra; and Walker and De Waard, Trends Neurosci., 21(4):148–54 [1998]). The transduction of these stimuli results in oscillations in the intracellular concentration of calcium ions assuming the form of spikes and waves that encode signal information in their frequency and amplitude (De Koninck and Schulman, Science 279(5348):227–30 [1998]). The passage of calcium ions across the plasma membrane generating these calcium fluxes is governed by a diverse group of calcium channels encoded by separate gene families (McEnery, supra; and Walker and De Waard, supra). These calcium channels have a very wide distribution of expression throughout brain, muscle and the endocrine system, as well as other tissues (McEnery, supra; Walker and De Waard, supra; De Koninck and Schulman, supra; Gurnett et al. Neuron 16(2):431–40 [1996]; and Miller, Trends Neurosci., 20(5):189–92 [1997]).

These channels are formed by heteromultimeric complexes of $\alpha$1, $\alpha_2\delta$, $\beta$, and $\gamma$ subunits. Electrophysiological and molecular cloning studies have revealed an incredible diversity of voltage-gated calcium channels. Physically, the voltage-gated calcium channels are composed of five subunits each encoded by separate distinct gene families (Walker and De Waard, supra). The major alpha 1 ($\alpha_1$) subunit which is encoded by at least 6 different genes is the pore-forming protein which interacts with other auxiliary subunits (i.e., alpha2 ($\alpha_2$), beta ($\beta$), gamma ($\gamma$), and delta ($\delta$)) to produce fully functional channels composed by unique combinations of distinct gene products. The auxiliary subunits (i.e., $\alpha_2$, $\beta$, $\gamma$ and $\delta$) with the exception of the gamma subunit significantly increase the functional expression of calcium currents. Like the alpha 1 subunit, the beta and gamma subunits are encoded by several genes; the beta subunit is encoded by 4 genes, while the gamma subunit is encoded by two genes.

The $\alpha$1 subunits contain the channel pore, voltage sensors, and the receptors for various classes of drugs and toxins (Perez-Reyes and Schneider, Kidney Int'l., 48:1111–1124 [1995]). There are three families of $\alpha$1 subunits: the L-type (or $C_v$1 family), composed of $\alpha$1S, $\alpha$1 C, ($Ca_v$1.2), $\alpha$1D, and $\alpha$1F; the non-L-type high voltage-activated ($Ca_v$2) family composed of P/Q-types encoded by $\alpha_1$A, the N-type is encoded by $\alpha$1B ($Ca_v$2.2), and R-types encoded by $\alpha$1E; and the T-type family ($Ca_v$3), encoded by $\alpha$1G ($Ca_v$3.1), $\alpha$1H, and $\alpha$1I. Klugbauer et al. (Klugbauer et al., supra) cloned another related $\alpha_2\delta$ subunit (i.e., a subunit that is different from the present invention), then proposed the following nomenclature: $\alpha_2\delta$-1, for the original $\alpha_2\delta$ cloned from skeletal muscle; $\alpha_2\delta$-2 for the protein described herein, and $\alpha_2\delta$-3 for their novel sequence. Similarly the genes may be referred to as CACNA2D1, CACNA2D2, and CACNA2D3, respectively (Lory et al., Hum. Genet., 100 (2):149–150 [1997]). An $\alpha_2\delta$-2 clone (KIAA0558, GenBank # AB011130, NP 006021.1) was recently independently isolated by the Kazusa DNA Research Institute from human brain as part of large scale anonymous cDNA sequencing efforts (Nagase et al., DNA Res., 5(1):31–39 [1998]).

Co-expression studies have established two physiological roles for $\beta$ subunits in high voltage-activated (HVA) $Ca^{2+}$ channels, by dramatically increasing α1 expression at the plasma membrane and altering the biophysical properties of the channel currents. In general, β subunits have little effect on the expression of low voltage-activated (LVA) currents (See, Dolphin et al., J. Physiol., 519.1:35–45 [1999]). Although only one γ and $α_2δ$ subunit have been biochemically characterized, there is recent evidence to suggest that there may be additional members of these gene families (See e.g., Letts et al., Nature Genet., 19:340–347 [1998]; Black, Mayo Clin. Proc. 74(4):357–361 [1999]; and Klugbauer et al., supra). The γ1 subunit was shown to be part of the skeletal muscle L-type channel (Sharp and Campbell, J. Biol. Chem., 264(5):2816–2825 [1989]). In addition, co-expression studies have indicated that this subunit aids in the formation of L-type channels (assayed by dihydropyridine binding (Suh-Kim et al., Recept. Channels 4(4):217–225 [1996]), and may play a role in channel inactivation (Singer et al., Science 253(5027):1553–1557 [1991]).

The $α_2δ$ subunit ($α_2δ$-1) was first identified in biochemical studies of skeletal muscle L-type $Ca^{2+}$ channels (See, Perez-Reyes and Schneider, Kidney Intl., 48:1111–1124 [1995]). Through the use of antibodies, it has also been shown to be part of the cardiac L-type and neuronal N-type channels (See, Schmid et al., Biochem., 25(12):3492–3495 [1986]; and McEnery et al., Proc. Natl. Acad. Sci. USA 88(24):11095–11099 [1991]). $α_2δ$-1 cDNA has been cloned from skeletal muscle and brain cDNA libraries (Ellis et al., Science 241(4873):1661–1664 [1988]; De Jongh et al., J. Biol. Chem., 265(25):14738–14741 [1990]; and Williams et al., Neuron 8(1):71–84 [1992]). The 175 kDa protein product is post-translationally cleaved to form disulfide-linked α2 and δ peptides, both of which are heavily glycosylated. Biochemical and mutation analysis supports a single transmembrane domain in the δ subunit that anchors the $α_2δ$ protein to the membrane (Brown and Gee, J. Biol. Chem., 273(39):25458–25468 [1998]). Co-expression of $α_2δ$-1 with both HVA and LVA α1 subunits facilitates the assembly of channels in the plasma membrane (Dolphin et al., J. Physiol., 519.1:35–45 [1999]; Suh-Kim et al., Recept. Channels 4(4):217–225 [1996]; and Burst et al., Neuropharmacol., 32(11):1089–1102 [1993]). Co-expression studies also indicate that $α_2δ$-1 can alter the pharmacological properties of L-type channels. In contrast to the β subunits that have a dramatic effect on gating of all HVA channel in many expression systems, the effects of $α_2δ$-1 are more controversial, perhaps depending on the α1 subunit used or the expression system. For example, $α_2δ$-1 has little or no effect on either L-type (Wei et al., J. Biol. Chem., 279(45):27106–27111 [1995]; and Biel et al., FEBS Lett., 269(2):409–412 [1990]) or N-type currents expressed in Xenopus oocytes (Brust et al, Neuropharmacol., 32(110):1089–1102 [1993]), but appears to affect inactivation of L-type channels expressed in mammalian cells (Shirokov et al., J. Gen. Physiol., 111(6):807–823 [1998]; and Bangalore et al., Am. J. Physiol., 270(5 Pt. 2):H1521–1528 [1996]). The opposite result occurred in studies on α1E-mediated currents, where no effect was observed in mammalian cells (Jones et al., J. Gen. Physiol., 112(2):125–143 [1998]), ) and effects on channel inactivation were observed in Xenopus oocytes (Qin et al., J. Gen. Physiol., 274(5 Pt. 1):C1324–1331 [1998]). The $α_2δ$-1 subunit has a high affinity binding site for the anti-epileptic drug gabapentin (Brown and Gee, J. Biol. Chem., 273(39):25458–25465 [1998]). Gabapentin has been shown to modestly inhibit (~30%) neuronal $Ca^{2+}$ currents, although it is unclear if this is its mechanism of action (Stefani et al., Neuropharmacol., 37(1):83–91 [1998]). Nonetheless, it is not necessary to understand the mechanisms involved with calcium channels in order to use the present invention.

Recent studies that demonstrated the association of mutations in calcium channel genes (α1 and β genes) with inherited and acquired diseases further underlined the importance of calcium channels and have created a new field of research aimed at understanding and controlling these "channelopathies" (Miller, supra). Thus, efforts were made to obtain sequences of calcium channel subunit genes, such as the human ($alpha_2$)-subunit gene (Ellis et al., Science 241(4873):1661–[1988]; Williams et al., Neuron, 8(1):71–84 [1992]; Ellis et al. U.S. Pat. No. 5,686,241; and Harpold et al., U.S. Pat. No. 5,792,846), and its murine (GenBank Accession ## U73483-U73487), rat (GenBank Accession # M86621), porcine (GenBank Accession # M21948), and rabbit orthologs (GenBank Accession # AF077665). The regulatory $α_2δ$ subunit (exemplified by the sequences disclosed herein) is of special importance since it plays a dual function in both current stimulation and subunit interaction by changing microscopic channel properties (Gurnett et al., supra).

B. Using Probes to Identify and Isolate DNA Encoding $α_2δ$ Calcium Channel Peptides The present invention contemplates using a portion of the nucleic acid sequences set forth as SEQ ID NOs: 1, 3 and 5 as probes. As used herein, the term "probe" refers to an oligonucleotide, whether occurring naturally as in a purified restriction digest or produced synthetically, recombinantly or by PCR amplification, which is capable of hybridizing to another oligonucleotide of interest. A probe may be single-stranded or double-stranded. It is contemplated that any probe used in the present invention will be labelled with any "reporter molecule," so that it is detectable in any detection system including, but not limited to enzyme (e.g., ELISA, as well as enzyme-based histochemical assays), fluorescent, radioactive, colorimetric, gravimetric, magnetic, and luminescent systems. It is not intended that the present invention be limited to any particular detection system or label.

The probes provided herein are useful in the detection, identification and isolation of, for example, $α_2δ$ subunit sequences such as those listed as SEQ ID NOs:1, 3 and 5 as well as of homologs thereof. Preferred probes are of sufficient length (e.g., from about 9 nucleotides to about 20 nucleotides or more in length) such that high stringency hybridization may be employed.

The probes provided herein are also useful in the detection, diagnosis and typing of preneoplasias and cancers. This utility is based on the inventors' observation that genetic disruption of the 3p21.3 region (in which the $α_2δ$ gene is located) is common in cancer (e.g., lung cancer and breast cancer) and preneoplastic lesion (e.g., hyperplasia, dysplasia, carcinoma in situ). This observation was based on the inventors' results using cells which represent clones of cells that contained 3p21.3 genetic lesions (compare Wistuba et al., J. Natl. Cancer Instit., 89:1366–1377 [1997]). It is also the inventors' consideration that genetic disruption of 3p21.3 which is associated with mutation or strand break of the $α_2δ$ gene leads to reduced expression of the $α_2δ$ gene and/or inactivation of the expressed $α_2δ$ subunit peptides. Furthermore, the present invention also contemplates methylation of the promoter region to inactivate its expression.

As used herein, the term "mutation" refers to a deletion, insertion, or substitution. A "deletion" is defined as a change in a nucleic acid sequence in which one or more nucleotides is absent. An "insertion" or "addition" is that change in a nucleic acid sequence which has resulted in the addition of one or more nucleotides. A "substitution" results from the replacement of one or more nucleotides by a molecule which is different molecule from the replaced one or more nucleotides. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol. The term "strand break" when made in reference to a double stranded nucleic acid sequence includes a single-strand break and/or a double-strand break. A single-strand break refers to an interruption in one of the two strands of the double stranded nucleic acid sequence. This is in contrast to a double-strand break which refers to an interruption in both strands of the double stranded nucleic acid sequence.

Diagnosis and detection of cancer and/or preneoplastic lesions using the invention's probes involves the use of nucleic acid probes which hybridize with $\alpha_2\delta$ nucleotide sequences that are associated with cancer and/or preneoplastic lesion. These probes are used in hybridization assays (e.g., in situ hybridization) with nucleic acid sequences from cells suspected of cancerous and/or preneoplastic. Hybridization of the nucleic acid sequences with these probes indicates that the cells are cancerous and/or preneoplastic.

C. Using Primers to Amplify Splice Variant RNAs Encoding $\alpha_2\delta$ Calcium Channel Peptides The invention also specifically contemplates using a portion of the nucleic acid sequences set forth as SEQ ID NOs:1, 3 and 5 as primers for the amplification of nucleic acid sequences by, for example, polymerase chain reactions (PCR) or reverse transcription-polymerase chain reactions (RT-PCR). Exemplary primers which are used to amplify exon sequences of the $\alpha_2\delta$ gene are illustrated in Tables 1 and 2 (Example 7, infra). The term "amplification" is defined as the production of additional copies of a nucleic acid sequence and is generally carried out using polymerase chain reaction technologies well known in the art (Dieffenbach and Dveksler, PCR Primer, a *Laboratory Manual,* Cold Spring Harbor Press, Plainview N.Y. [1995]). As used herein, the term "polymerase chain reaction" ("PCR") refers to the method of K. B. Mullis disclosed in U.S. Pat. Nos. 4,683,195, 4,683,202 and 4,965,188, all of which are hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are the to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled deoxyribonucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long (e.g., from about 9 nucleotides to about 20 nucleotides or more in length) to prime the synthesis of extension products in the presence of the inducing agent. Suitable lengths of the primers may be empirically determined and depend on factors such as temperature, source of primer and the use of the method.

The primers contemplated by the invention are useful in, for example, identifying sequences which are homologous to the $\alpha_2\delta$ sequences in humans and in other species.

D. Using Nucleic Acid Sequences for Gene Therapy

The $\alpha_2\delta$ nucleic acid sequences provided herein may be used for gene therapy applications in both non-human animals as well as in humans.

Viral vectors commonly used for in vivo or ex vivo targeting and therapy procedures are DNA-based vectors and retroviral vectors. Methods for constructing and using viral vectors are known in the art (See e.g., Miller and Rosman, BioTechn., 7:980–990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA virus, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320–330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (Stratford-Perricaudet et al., J. Clin. Invest., 90:626–630 [1992]; See also, La Salle et al., Science 259:988–990 [1993]); and a defective adeno-associated virus vector (Samulski et al., J. Virol., 61:3096–3101 [1987]; Samulski et al., J. Virol. 63:3822–3828 [1989]; and Lebkowski et al., Mol. Cell. Biol., 8:3988–3996 [1988]).

Preferably, for in vivo administration, an appropriate immunosuppressive treatment is employed in conjunction with the viral vector (e.g., adenovirus vector), to avoid immunodeactivation of the viral vector and transfected cells. For example, immunosuppressive cytokines, such as interleukin- 12 (IL-12),interferon-gamma (IFN-γ), or anti-CD4 antibody, can be administered to block humoral or cellular immune responses to the viral vectors. In addition, it is advantageous to employ a viral vector that is engineered to express a minimal number of antigens. Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963–967 [1992]; Wu and Wu, J. Biol. Chem., 263:14621–14624 [1988]; and Williams et al., Proc. Natl. Acad. Sci. U.S.A., 88:2726–2730 [1991]). Receptor-mediated DNA delivery approaches can also be used (Curiel et al., Hum. Gene Ther., 3:147–154 [1992]; and Wu and Wu, J. Biol. Chem., 262:4429–4432 [1987]).

For example, the nucleic acids provided herein may be introduced into cancer or preneoplastic cells using an expression vector which encodes a $\alpha_2\delta$ subunit protein using a variety of means known in the art to be useful both for delivery in vivo and ex vivo, including (1) retroviral transduction, (2) recombinant adenoviral vectors, (3) recombinant adeno-associated vectors, (4) targeted cationic liposomes, and (5) gene transfer using biolistics, as described in the following sections.

1. Retroviral Transduction

In one embodiment, the gene can be introduced in a retroviral vector (e.g., as described in U.S. Pat. Nos. 5,399, 346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference); the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Retroviral vectors encoding $\alpha_2\delta$ subunit proteins may be used for the expression of $\alpha_2\delta$ subunit proteins in established or primary tumor cells. The transfer of $\alpha_2\delta$ genes encoding subunit proteins using retroviruses may be made more efficient by increasing the titer of the virus encoding the $\alpha_2\delta$ subunit proteins and increasing the transduction efficiency. To increase the virus titer, the retroviral construct may be designed to include a selectable marker (e.g., neo gene), and cells harboring the retroviral construct are selected by growth in the presence of a suitable selective agent (e.g., G418) followed by expansion of clones producing the highest titers of virus. To improve the transduction efficiency, retrovirus are used in combination with liposomes or poly-L-ornithine or polylysine to enhance virus uptake.

Another way to improve gene transfer efficiency using retroviruses is to increase the targeting efficiency. Many tumor cells including glioblastomas and melanomas express excess levels of the transferrin receptor. Transferrin has been used to increase the transduction efficiency of adenovirus in combination with polylysine. Several recent reports demonstrated that replacing the SU (surface) domain of the env gene of a retrovirus can increase receptor-mediated transduction efficiency. The human transferrin gene is 2097 bp long and its insertion into the SU domain of the env gene of MLV vector may not produce a stable Env product. However, since earlier studies have suggested that the modified Env fusion protein requires the native Env for stable assembly and efficient entry, co-transfection of the transferrin-env fusion gene with the native env gene may be used to produce retrovirus particles bearing a mixture of wild type and recombinant Env. The gene transfer efficiency of the new vector may be examined by transducing tumor cells expressing high levels of transferrin receptor.

2. Recombinant Adenoviral Vectors

In an alternative embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given in one alternative embodiment, within the scope of the present invention, to type 2 or type 5 human adenoviruses (Ad 2 or Ad 5), or adenoviruses of animal origin (See, WO94/26914). Those adenoviruses of animal origin that can be used within the scope of the present invention include adenoviruses of canine, bovine, murine (e.g., Mavl, Beard et al., Virol., 75–81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)). Recombinant adenoviruses can accommodate relatively large segments of foreign DNA (~7 kb), and have the advantage of a broad host cell range and high titer virus production. Adenoviruses have been used in vivo in rats to efficiently deliver genes to the liver and the pancreatic islets (reviewed in Becker et al., *In Protein Expression in Animal Cells,* Roth et al. (eds.) [1994]) and to the central nervous system (Davidson et al., Nature Genet., 3:219 [1993]). Rat livers have also been efficiently transduced ex vivo and then re-implanted (Shaked et al., Transplant., 57:1508 [1994]).

Preferably, the replication defective adenoviral vectors of the invention comprise the ITRs, an encapsidation sequence and the nucleic acid of interest. Still more preferably, at least the El region of the adenoviral vector is non-functional. The deletion in the El region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO95/02697), the E2 region (e.g., WO94/28938), the E4 region (e.g., WO94/28152, WO94/12649 and WO95/02697), or in any of the late genes L1–L5.

In a preferred embodiment, the adenoviral vector has a deletion in the E1 region (Ad 1.0). The replication defective recombinant adenoviruses are preferably employed; in some embodiments, these viruses contain a deletion of the key immediate early genes E1a and E1b. To generate and propagate recombinant viruses, a packaging cell line such as 293 cells which supply the E1a and E2a proteins in trans is employed. Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid which carries, inter alia, the DNA sequence of interest. The homologous recombination is effected following co-transfection of the adenovirus and plasmid into an appropriate cell line. The cell line that is employed should preferably (i) be transformable by the elements, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques, that are well known to one of ordinary skill in the art.

In particular, recombinant adenoviruses are created by making use of intracellular recombination between a much larger plasmid encoding most of the viral genome and a small plasmid containing the gene of interest (i.e., a gene encoding a $\alpha_2\delta$ subunit protein) flanked by regions of homology with the viral integration site. Standard methods may be used to construct the recombinant adenoviruses (Graham and Prevec, Meth. Mol. Biol., 7:109–128 [1991]; and Becker et al., supra). Briefly, each plasmid is co-transfected together with pJM17 (Microbix Systems, Toronto) into sub-confluent monolayers of 293 cells (ATCC CRL 1573) using calcium phosphate precipitation and a glycerol shock. Initial recombinant viral stocks are titered on monolayers of 293 cells, and isolated single plaques are obtained and tested for $\alpha_2\delta$ subunit protein expression using ELISA. Viral stocks are amplified and titered on 293 cells, and stored in aliquots at −70° C.; if necessary, stocks are concentrated by centrifugation on density gradients. To infect tumor cells with recombinant adenoviruses, freshly isolated tumor cells are mixed with adenoviral stocks in a minimal volume. Titers of stocks are typically $10^5-10^8$/ml. Medium is replaced after several hours and the cells are followed for expression of the recombinant adenoviral-encoded $\alpha_2\delta$ subunit proteins and/or reporter genes.

A potential drawback of using an adenoviral delivery system is that the transduced cells may retain or express small quantities of adenoviral antigens on their surface. "Second generation" adenoviral vectors which contain deletions in the E2a gene are available and are associated with less inflammation in the recipient and a longer period of expression of the gene of interest (Engelhardt et al., Proc. Natl. Acad. Sci. USA 91:6196 [1994]). If necessary, nucleic acid sequences encoding $\alpha_2\delta$ subunit proteins are inserted into second generation adenoviral vectors.

3. Adeno-Associated Viral Vectors

In a further alternative embodiment, the vector is an adeno-associated virus (AAV) vector. The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. Nos. 4,797,368; 5,139,941; 5,843,742; and EP 488 528; See also, Hermonat et al., Proc. Natl. Acad. Sci. USA 81:6466–6470 [1984]; Chiorini et al., J. Virol., 71:6823–6833 [1997]; and Chorini et al., J. Virol., 73:1309–1319 [1999]; each of which is incorporated by reference). These publications describe various AAV-derived constructs in which the rep and/or cap genes are deleted and replaced by a gene of interest, and the use of these constructs for transferring the gene of interest in vitro (into cultured cells) or in vivo, (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

4. Targeted Cationic Liposomes

Alternatively, the vector can be introduced in vivo by lipofection. For the past decade, there has been increasing use of liposomes for encapsulation and transfection of nucleic acids in vitro. Furthermore, synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. U.S.A., 84:7413–7417 [1987]; See also, Mackey, et al., Proc. Natl. Acad. Sci. U.S.A., 85:8027–8031 [1988]; and Ulmer et al., Science 259:1745–1748 [1993]). The use of cationic lipids may promote encapsulation of negatively charged nucleic acids, and also promote fusion with negatively charged cell membranes (Felgner and Ringold, Science 337:387–388 [1989]). Particularly useful lipid compounds and compositions for transfer of nucleic acids are described in WO95/18863 and WO96/17823, and in U.S. Pat. No. 5,459,127, herein incorporated by reference.

Cationic liposomes have proven to be a safe and effective means for inducing the transient expression of DNA in target cells [Ledley, Hum. Gene Ther., 6:1129 [1995]; Felgner, Adv. Drug Del. Rev., 5:167 [1990]; Felgner et al. Proc. Natl. Acad. Sci. USA 84:7413 [1987]; and Smith et al., Biochim. Biophys. Acta 1154:327 [1993]). Clinical trials are underway using cationic liposomes to introduce the CFTR gene into the lungs of cystic fibrosis patients (Caplen et al., Gene Ther. 1:139 [1994]; and Alton et al., Nature Genet., 5:135 [1993]) or to introduce, by direct intra-tumor injection, the T cell costimulator B7-1 into malignant melanoma lesions in order to induce a cell-mediated immune response (Nabel et al., Proc. Natl. Acad. Sci. USA 90:11307 [1993]).

Cationic liposomes (e.g., DOTAP/DOPE) and ligand-targeted cationic liposomes may be employed for the delivery of $\alpha_2\delta$ subunit proteins to tumor cells. Ligand-targeted liposomes are made by covalently attaching ligands or antibodies to the surface of the cationic liposome. For example, when glioblastoma cells are to be targeted, transferrin is used as the ligand as glioblastoma cells express high levels of the transferrin receptor on their surface. When melanoma cells are to be targeted, internalizing receptors, monoclonal antibodies directed against melanoma-specific surface antigens (e.g., mAb HMSA5) may be employed as the ligand.

Plasmid DNA encoding $\alpha_2\delta$ subunit proteins is formed into a complex with preformed cationic liposomes using standard methodology or alternatively the DNA is encapsulated into the liposome interior. The DNA-containing liposomes are then used to transfer the DNA to tumor cells in vivo by direct intra-tumor injection or in vitro (using freshly explanted tumor cells) followed by return of the transduced cells to the recipient (e.g., a human patient or non-human animal).

5. Gene Transfer Using Biolistics

Biolistics (microballistics) is a method of delivering DNA into cells by projection of DNA-coated particles into cells or tissues. DNA is coated onto the surface of gold or tungsten microparticles (~1–3 $\mu$m diameter) and these particles are accelerated to high velocity and are impacted onto the target cells. The particles burst through the cell membrane and lodge within the target cell. The cell membrane quickly reseals and the passenger DNA elutes off of the particle and is expressed. The biolistic method has been used to transfect mammalian cells (Williams et al., Proc. Natl. Acad. Sci. USA 88:2726 [1991]; Tang et al., Nature 356:152 [1992]; and Sanford et al., Meth. Enzymol., 217:483 [1993]).

A hand-held biolistic apparatus (BioRad) is used to transfer DNA into tumor cells or isolated tumor fragments. This device uses compressed helium to drive a disc-shaped macroprojectile which carries on its surface microparticles (1–5 $\mu$m) of gold which have been coated with purified plasmid DNA (coprecipitated with spermine) (Williams et al., supra). This apparatus has been used to successfully transfect primary tissues.

Plasmid DNA encoding the $\alpha_2\delta$ subunit proteins may be coated onto the surface of gold microparticles according to the manufacturer's instructions (BioRad) and the biolistic apparatus is used to transfer the DNA into freshly explanted tumor cells or directly into exposed tumors (e.g., metastatic nodules on the surface of the liver, melanoma lesions on the skin).

Regardless of the method of delivery of the expression vector into a cell, it is preferred, though not required, that the expression vector contain a selection marker (e.g., neo gene) to facilitate selection of transfected cells. Transfected cells are selected by growth in the presence of G418 (e.g., 200 $\mu$g/ml), followed by culture in growth medium containing reduced concentrations of G418 (e.g., 100 $\mu$g/ml) and growth to confluence. Expression of the $\alpha_2\delta$ subunit protein is evaluated using, for example, immunoblot analysis or flow cytometry using monoclonal antibodies which are specific for the $\alpha_2\delta$ subunit protein. It is preferred, though not necessary, that expression of the $\alpha_2\delta$ subunit protein in the transfected tumor cells is both constitutive and stable. Constitutive expression refers to expression in the absence of a triggering event or condition, and can be achieved by the selection of a promoter which drives expression of the nucleic acid sequence encoding the $\alpha_2\delta$ subunit protein. Examples of promoters which drive constitutive expression of a structural nucleic acid sequence which is operably linked to the promoter include the SR$\alpha$ promoter, CMV promoter, and HIV promoter.

Regardless of the type of expression vector used for delivery of the $\alpha_2\delta$ nucleic acid sequences into a cell, the expression vector may be introduced to the cell by direct injection into tumor and/or preoplastic tissue, systemic (e.g., intravenous) administration, aerosol administration (e.g., for delivery to the bronchial tree and other lung tissues), injection into breast ducts (e.g., for delivery to breast tissue), topical administration (e.g., for delivery to cervical tissue). It is expected that the $\alpha_2\delta$ nucleic acids of the invention would function as a tumor suppressor. Tumor suppressor function may be determined by (for example) reduction in the size of tumors which are detectable at the time of administration of the expression vectors containing $\alpha_2\delta$ nucleic acid sequences as compared to the size of the tumors prior to such administration. Alternatively, where the expression vectors containing $\alpha_2\delta$ nucleic acid sequences are introduced to preneoplastic cells, tumor suppressor function may be determined by lack of progression of the preneoplastic cells to cancer cells over time.

E. Generation of Calcium Channel $\alpha_2\delta$ Subunit Peptides

The present invention provides the polypeptide sequences of isoform I (SEQ ID NOs:2 and 4) and isoform II (SEQ ID NO:6) of the human calcium channel $\alpha_2\delta$ subunit and specifically contemplates portions and variants thereof. For example, $\alpha_2\delta$ subunit variants included within the scope of this invention include $\alpha_2\delta$ subunit polypeptide sequences containing deletions, insertions or substitutions of amino acid residues which result in a polypeptide that is functionally equivalent to the $\alpha_2\delta$ subunit polypeptide isoforms. By the term "functionally equivalent to the $\alpha_2\delta$ subunit polypeptide isoforms" is meant that a polypeptide is capable of associating with at least an $\alpha_1$ subunit (preferably with $\alpha_1$ and $\beta$ subunits, and more preferably with $\alpha_1$, $\beta$ and $\gamma$ subunits) to produce a functional calcium channel. For example, amino acids may be substituted for other amino acids having similar characteristics of polarity, charge, solubility, hydrophobicity, hydrophilicity and/or amphipathic nature. Alternatively, substitution of amino acids with other amino acids having one or more different characteristic may be desirable for the purpose of producing a polypeptide which is secreted from the cell in order to, for example, simplify purification of the polypeptide.

The $\alpha_2\delta$ subunit isoform I and II polypeptide sequences and their functional variants may be made using chemical synthesis. For example, peptide synthesis of the $\alpha_2\delta$ subunit polypeptide, in whole or in part, can be performed using solid-phase techniques well known in the art. Synthesized polypeptides can be substantially purified by high performance liquid chromatography (HPLC) techniques, and the composition of the purified polypeptide confirmed by amino acid sequencing. One skilled in the art would recognize that variants of the $\alpha_2\delta$ subunit isoform I and II polypeptides can be produced by manipulating the polypeptide sequence during and/or after its synthesis.

The $\alpha_2\delta$ subunit and its functional variants can also be produced by an expression system. Expression of $\alpha_2\delta$ subunit isoform I and II polypeptides may be accomplished by inserting nucleotide sequences which encode these polypeptides (or variants, portions, or homologs of the nucleotide sequences) into appropriate vectors to create expression vectors, and transfecting the expression vectors into host cells. The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. Expression in insect cells (e.g., Spodoptera) using insect vectors (e.g., baculovirus) is also contemplated to be within the scope of the invention.

The scope of this invention further encompasses amino acid sequences of the $\alpha_2\delta$ polypeptides ligated to one or more amino acid sequences as part of a fusion protein. Such fusion proteins may be desirable, for example, to detect expression of the $\alpha_2\delta$ polypeptides. Examples of amino acid sequences which may be used as fusion partners include β-galactosidase, luciferase, green fluorescent protein, Myc protein tags, FLAG tags, and chloramphenicol acetyltransferase. Fusion proteins may also be desirable to facilitate purification of the expressed $\alpha_2\delta$ polypeptides. For example, the heterologous sequence of protein A allows purification of the fusion protein on immobilized immunoglobulin. Other affinity traps are well known in the art and can be utilized to advantage in purifying the expressed fusion protein. For example, pGEX vectors (Promega, Madison Wis.) may be used to express the $\alpha_2\delta$ polypeptides as a fusion protein with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

While the invention discloses cloning of the sequences of the invention in the CMV expression vector pcDNA3.1 His C (Invitrogen), the adenovirus shuttle vector pLJ17 (pAdE1/ CMV), and the retrovirus tetracycline regulatable vectors pRev-TRE vector (Clontech) (Example 8), and in the pETE vector (Example 9), other expression vectors are expressly contemplated to be within the scope of the invention. Expression vectors are exemplified by plasmids, recombinant bacteriophage, cosmid DNA vectors, viruses and the like. Expression vectors can be constructed using techniques well known in the art (Sambrook et al., *Molecular Cloning, A Laboratory Manual,* Cold Spring Harbor Press, Plainview N.Y. [1989]; and Ausubel et al., *Current Protocols in Molecular Biology,* John Wiley & Sons, New York N.Y. [1989]). Briefly, the nucleic acid sequence of interest is placed in operable combination with transcription and translation regulatory sequences. The term "in operable combination" as used herein refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. Regulatory sequences include initiation signals such as start (i.e., ATG) and stop codons, promoters which may be constitutive (i.e., continuously active) or inducible, as well as enhancers to increase the efficiency of expression, and transcription termination signals. Transcription termination signals must be provided downstream from the structural gene if the termination signals of the structural gene are not included in the expression vector. Expression vectors may become integrated into the genome of the host cell into which they are introduced, or are present as unintegrated episomal vectors. Typically, unintegrated nonepisomal vectors are transiently expressed and regulated for several hours (e.g., 72 hours) after transfection.

The choice of promoter is governed by the type of host cell to be transfected with the expression vector. Host cells include, but are not limited to eukaryotic cells, prokaryotic cells, insect cells, etc. In one embodiment the cell is eukaryotic. In a more preferred embodiment, the eukaryotic cell is a cancer cell. Other eukaryotic cells are expressly contemplated (e.g., COS cells, mouse L cells, Chinese hamster ovary cells, human embryonic kidney cells, and African green monkey cells). In an alternative preferred embodiment, the eukaryotic cell is an amphibian oocyte. In a more preferred embodiment, the amphibian oocyte is a frog oocyte.

Transfected cells may be identified by any of a number of marker genes. These include antibiotic (e.g., neomycin, puromycin, hygromycin for eukaryotic cells, and gentamicin, penicillin, and kanamycin for prokaryotic cells) resistance genes as well as marker or reporter genes (e.g., β-galactosidase, luciferase, green fluorescent protein, and Myc protein tags) which catalyze the synthesis of a visible reaction product.

Vectors may be introduced into a host cell using a number of standard and routine methods known to those skilled in the art (See e.g., Sambrook, et al., supra) including, but not limited to, microinjection, DEAE-dextran, calcium phosphate co-precipitation, cell fusion, electroporation, biolistics, lipofection, DNA viruses, and RNA viruses, or retrovirus-mediated transduction.

Expression of the $\alpha_2\delta$ nucleic acid sequences provided herein by transfected cells may be detected either indirectly using reporter genes, or directly by detecting mRNA or protein encoded by the $\alpha_2\delta$ nucleic acid sequences. Indirect detection of expression may be achieved by placing a reporter gene in tandem with the nucleic acid sequence encoding $\alpha_2\delta$ subunits under the control of a single promoter. Expression of the reporter gene indicates expression of the tandem $\alpha_2\delta$ subunit nucleic acid sequence. It is preferred that the reporter gene either have a visible reaction product or have a "tag" which may be detected by antibodies to give such a product. For example, cells expressing the reporter gene β-galactosidase produce a blue color when grown in the presence of X-Gal; cells grown in medium containing luciferin will fluoresce when expressing the reporter gene luciferase; cells containing green fluorescent protein spontaneously fluoresce when exposed to appropriate light wavelengths; cells expressing Myc, FLAG or His tags are detectable using commercially available anti-Myc, anti-FLAG or anti-His antibodies which are themselves coupled to a reporter molecule (e.g., enzyme or fluorescent compound).

Direct detection of expression of $\alpha_2\delta$ polypeptides can be achieved using methods well known to those skilled in the art. For example, mRNA isolated from transfected cells can be hybridized to labelled oligonucleotide probes and the hybridization detected. Alternatively, polyclonal or monoclonal antibodies specific for $\alpha_2\delta$ polypeptides can be used to detect expression of the recombinant $\alpha_2\delta$ polypeptide using enzyme-linked immunosorbent assay (ELISA), radioimmunoassay (RIA), fluorescent activated cell sorting (FACS) and immunohistochemical assays (e.g., enzyme-linked and fluorescent assays). Those skilled in the art recognize that, for example, immunohistochemical assays are useful in diagnostic test to identify individual cells which express $\alpha_2\delta$ polypeptides.

Recombinant $\alpha_2\delta$ polypeptides and their variants which are expressed by the host cell can be purified either from the culture medium, if the expression construct directs secretion into culture medium, or from the host cell lysate using purification techniques known in the art. For example, $\alpha_2\delta$ polypeptides may be expressed as a fusion protein with heterologous metal chelating peptides (i.e., polyhistidine tracts) or with protein A domains, and purified on commercially available immobilized metals or immunoglobulins, respectively.

The polypeptides of the invention are also useful in treating patients with Lambert-Eaton myasthenic syndrome (LEMS). LEMS is an autoimmune disease characterized by an insufficient release of acetylcholine from motor nerve terminals which normally are responsive to nerve impulses. Immunoglobulins (IgG) from LEMS patients block voltage-dependent calcium channels and thus inhibit calcium channel activity. Treatment of LEMS patients may be achieved by using a recombinant $\alpha_2\delta$ protein to clear patients' blood of the damaging autoantibodies.

The polypeptides of the invention are additionally useful for reconstituting a fully functional channel (e.g., on the cell membrane of frog eggs) by, for example, introducing into a cell expression vectors which encode the $\alpha 1$ subunit [Harpold et al. supra] as well as the $\alpha_2\delta$ subunits of the invention, and optionally the β-subunit and/or γ-subunit (Harpold et al., supra).

Additionally, those skilled in the art recognize that the $\alpha_2\delta$ subunit polypeptide sequences of the present invention are useful in generating antibodies as further described below.

F. Generation of Antibodies Directed to Calcium Channel $\alpha_2\delta$ Peptides Antibodies (polyclonal and monoclonal) which are specific for at least a portion of the $\alpha_2\delta$ subunit isotype I and II provided herein may be generated using methods known in the art (see Example 8). The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells. The terms "specific binding," "specifically binding" and grammatical equivalents thereof when used in reference to the interaction of an antibody and a protein or peptide mean that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A", the presence of a protein containing epitope A (or free, unlabelled A) in a reaction containing labelled "A" and the antibody will reduce the amount of labelled A bound to the antibody.

Those skilled in the art know how to make polyclonal and monoclonal antibodies which are specific to a desirable polypeptide. These include but are not limited to the hybridoma technique originally developed by Köhler and Milstein (Köhler and Milstein, Nature 256:495–497 [1975]), as well as the trioma technique, the human B-cell hybridoma technique (See e.g., Kozbor et al. Immunol. Today 4:72 [1983]), and the EBV-hybridoma technique to produce human monoclonal antibodies (Cole et al., in *Monoclonal Antibodies and Cancer Therapy,* Alan R. Liss, Inc., pp. 77–96 [1985]). For example, as described further below, monoclonal antibodies may be generated by immunizing an animal (e.g., mouse, rabbit, etc.) with a desired antigen and the spleen cells from the immunized animal are immortalized, commonly by fusion with a myeloma cell. Furthermore, the present invention encompasses antibodies produced using genetic immunization (e.g., immunization of an animal with a recombinant construct that provokes an immune response against the construct by the animal).

In an additional embodiment of the invention, monoclonal antibodies can be produced in germ-free animals utilizing relatively recent technology (See e.g., PCT/US90/02545). Also according to the invention, human antibodies may be used and can be obtained by using human hybridomas (Cote et al., Proc. Natl. Acad. Sci. U.S.A.80:2026–2030 [1983]).

According to the invention, techniques described for the production of single chain antibodies (U.S. Pat. No. 4,946, 778; herein incorporated by reference) can be adapted to produce $\alpha_2\delta$ single chain antibodies. An additional embodiment of the invention utilizes the techniques described for the construction of Fab expression libraries (Huse et al., Science 246:1275–1281 [1989]) to allow rapid and easy identification of monoclonal Fab fragments with the desired specificity for $\alpha_2\delta$.

Antibody fragments which contain the idiotype (antigen binding region) of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

For monoclonal antibody production, immunization with antigen may be accomplished in the presence or absence of an adjuvant (e.g., Freund's adjuvant). Typically, for a mouse, 10 μg antigen in 50–200 μl adjuvant or aqueous solution is administered per mouse by subcutaneous, intraperitoneal or intramuscular routes. Booster immunization may be given at intervals, e.g., 2–8 weeks. The final boost is given approximately 2–4 days prior to fusion and is generally given in aqueous form rather than in adjuvant.

Spleen cells from the immunized animals may be prepared by teasing the spleen through a sterile sieve into culture medium at room temperature, or by gently releasing the spleen cells into medium by pressure between the frosted ends of two sterile glass microscope slides. The cells are harvested by centrifugation (400×g for 5 min.), washed and counted. Spleen cells are fused with myeloma cells to generate hybridoma cell lines. Several mouse myeloma cell lines which have been selected for sensitivity to hypoxanthine-aminopterin-thymidine (HAT) are commercially available and may be grown in, for example, Dulbecco's modified Eagle's medium (DMEM) (Gibco BRL) containing 10–15% fetal calf serum. Fusion of myeloma cells and spleen cells may be accomplished using polyethylene glycol (PEG) or by electrofusion using protocols which are routine in the art. Fused cells are distributed into 96-well plates followed by selection of fused cells by culture for 1–2 weeks in 0.1 ml DMEM containing 10–15% fetal calf serum and HAT. The supernatants are screened for antibody production using methods well known in the art. Hybridoma clones from wells containing cells which produce antibody are obtained (e.g., by limiting dilution). Cloned hybridoma cells (4–5×10$^6$) are implanted intraperitoneally in recipient mice, preferably of a BALB/c genetic background. Sera and ascites fluids are collected from mice after 10–14 days.

The invention also contemplates humanized antibodies which are specific for at least a portion of the $\alpha_2\delta$ subunit isotype I and II provided herein. Humanized antibodies may be generated using methods known in the art, such as those described in U.S. Pat. Nos. 5,545,806; 5,569,825 and 5,625,126, the entire contents of each of which are incorporated by reference. Such methods include, for example, generation of transgenic non-human animals which contain human immunoglobulin chain genes and which are capable of expressing these genes to produce a repertoire of antibodies of various isotypes encoded by the human immunoglobulin genes.

The antibodies of the invention which are directed against $\alpha_2\delta$ polypeptides may be used for the detection of expression of the $\alpha_2\delta$ proteins in cells. This may be desirable to, for example, use changes in the levels of expression of the cell's $\alpha_2\delta$ subunit proteins as a prognostic marker for the development of disease (e.g., cancer, neurological, autoimmune, and cardiovascular diseases) as well as for monitoring the efficacy of compounds in the prevention and treatment of these diseases. Thus, antibodies specific for $\alpha_2\delta$ polypeptides may be used to identify cells in clinically relevant samples from patients who have lost expression of the $\alpha_2\delta$ polypeptides.

Additionally, the antibodies provided herein may be used in the detection, diagnosis and typing of preneoplasias and cancers. For example, differences in the level of expression of the $\alpha_2\delta$ gene in preneoplastic and cancer cells as compared to normal cells may be used to detect and diagnose the presence of preneoplastic and cancer cells as well as to type such cells using methods known in the art, e.g., immunohistochemical assays including, but not limited to, enzyme-linked and fluorescent assays.

In the production of antibodies, screening for the desired antibody can be accomplished by techniques known in the art (e.g., radioimmunoassay, ELISA [enzyme-linked immunosorbant assay], "sandwich" immunoassays, immunoradiometric assays, gel diffusion precipitin reactions, immunodiffusion assays, in situ immunoassays [using colloidal gold, enzyme or radioisotope labels, for example], Western Blots, precipitation reactions, agglutination assays (e.g., gel agglutination assays, hemagglutination assays, etc.), complement fixation assays, immunofluorescence assays, protein A assays, and immunoelectrophoresis assays, etc. In addition, it is contemplated that phage display technology as known in the art will find use in conjunction with the present invention to detect the CACNA2D2 subunit in samples of interest.

G. Screening Compounds that Modulate the Activity of $\alpha_2\delta$ Calcium Channel Peptides The invention provides methods for identifying compounds (e.g., calcium channel agonists and antagonists) that modulate the activity of calcium channels. These methods involve contacting cells which have been transfected with an expression vector that contains $\alpha_2\delta$ nucleic acid sequences provided herein, and which express $\alpha_2\delta$ polypeptides, with a test compound as well as with a calcium channel selective ion (e.g., calcium ion, barium ion, etc.). This is followed by measuring the ability of the compound to alter the activity of the calcium channel in the transfected cell which expresses the heterologous $\alpha_2\delta$ polypeptides as compared to that in a control cell which does not express the heterologous $\alpha_2\delta$ polypeptides. The cell is maintained in a solution having a concentration of calcium channel selective ions which is sufficient to provide an inward current when the channels open. Methods which are similar to those of the instant invention but which utilize calcium channel subunits other than the invention's $\alpha_2\delta$ subunit are known in the art such as those described by Ellis et al, U.S. Pat. No. 5,407,820; Harpold et al., U.S. Pat. No. 5,429,921; and Harpold et al., U.S. Pat. No. 5,792,846, the entire contents of each of which are incorporated by reference.

The activity of the calcium channel is determined by measuring the magnitude and duration of the inward current caused by flow of calcium channel selective ions. The amount of current which flows through the recombinant calcium channel of the cell may be determined directly (e.g., physiologically) as described, for example, by Harpold et al., U.S. Pat. No. 5,792,846. Alternatively, the amount of current may be determined indirectly by monitoring an independent reaction which occurs intracellularly and which is directly influenced in a calcium (or other) ion dependent manner. For example, the cell expresses a heterologous $\alpha_2\delta$ subunit and also contains a transcriptional control element which is responsive to a calcium channel selective ion and which is operatively linked to a structural gene that encodes an indicator protein.

The assays of the invention may be used in conjunction with methods of rational drug design to select among compounds that modulate the activity of calcium channels. Such compounds may then be tested for their activity in the treatment of channelopathies (e.g., migraine, epilepsy, and episodic ataxia, cardiovascular diseases, LEMS, cancer, etc.) in model animals as well as human subjects.

H. In Vitro and In Vivo Suppression of Tumor Cell Growth

The function of the invention's $\alpha_2\delta$ nucleic acid sequences, portions and homologs thereof in suppression of tumor cell growth in vitro and in vivo may be ascertained using the following guidelines. The nucleic acid sequence of interest is cloned into a vector to generate an expression vector as described supra. The expression vectors are transfected into cancer cells which are then used for the determination of the effect of expression of the nucleic acid sequence of interest on cell growth both in vitro and in vivo. The cancer cells into which the expression vectors are transfected may be engineered to express only a heterologous functional $\alpha_2\delta$ subunit. This may be desirable where, for example, the transfected cancer cell expresses functional endogenous calcium channel subunits but lacks expression of a functional endogenous $\alpha_2\delta$ subunit. Alternatively, the cancer cells into which the expression vectors are transfected may be engineered to express $\alpha_2\delta$ subunits as well as calcium channel subunits other than the $\alpha_2\delta$ subunit, such as the human calcium channel alpha 1, beta, and gamma subunits disclosed in the art (Ellis et al. [1988] supra; Williams et al. [1992] supra; Ellis et al. U.S. Pat. No. 5,686,241; and Harpold et al., U.S. Pat. No. 5,792,846).

For example, transfected tumor cells which express the $\alpha_2\delta$ nucleic acid sequence as well as control cells (i.e., corresponding tumor cells which have not been transfected with the expression vector) are cultured in vitro under conditions which result in growth of the control cells as determined by, for example, an increase in cell number over a period of time. Growth of the control and transfected cells is then compared. Detection of a growth level which is statistically lower in the transfected cells as compared to the control cells indicates that the nucleic acid sequence of interest functions as a tumor suppressor.

It is also contemplated that the present invention encompass methods that include the measurement of apoptosis (i.e., programmed cell death) either by itself or after other treatment (e.g., drugs). An increase in apoptosis could be viewed as a consequence of a normal function of the calcium channel gene product under certain conditions.

The tumor suppressor function of the sequence of interest may also be determined in vivo. This may be accomplished by introducing (e.g., by injection) transfected and control tumor cells into a host animal (e.g., mouse, etc.) and observing the growth of the introduced tumor cells as determined, for example, by the number of tumors, time at which tumors are first detected, and/or change in the diameter of a tumor over a period of time. One of skill in the art knows that immunological rejection of the tumor cells by the host animal is undesirable and may be avoided by, for example, introducing tumor cells which are derived from one species into a host of the same species (e.g., mouse tumor cells into a mouse host). Alternatively, tumor cells from one species may be introduced into an immunocompromised host animal of another species (e.g., human tumor cells into a nude (nu/nu) SCID mouse host). Detection of a growth level which is statistically lower in the transfected tumor cells as compared to the control tumor cells indicates that the nucleic acid sequence of interest functions as a tumor suppressor. Other measurements can also be used to assess the efficacy of treatment, including but not limited to determining whether there is a decrease in metastatic behavior of the tumor, an increase in apoptosis, a decrease in tumor angiogenesis, the complete absence of tumors, an increase in animal survival, and/or an increase in cure rates of animals.

I. Generating Transgenic Animals Expressing Reduced Levels of $\alpha_2\delta$ Calcium Channel Peptides In addition to animals which express increased levels of calcium channel $\alpha_2\delta$ polypeptides relative to a corresponding wild-type animal, the present invention provides transgenic non-human animals which express reduced levels of calcium channel $\alpha_2\delta$ polypeptides relative to a corresponding wild-type animal. The present invention also provides transgenic non-human animals which express reduced activity of calcium channel $\alpha_2\delta$ polypeptides relative to a corresponding wild-type animal.

The transgenic animals of the present invention are generated by introducing a targeting vector into a host cell. It is contemplated that the targeting vector contains the $\alpha_2\delta$ subunit nucleic acid sequences disclosed herein (e.g., SEQ ID NOs:1, 3, and 5). Additionally, the targeting vector may contain the $\alpha_2\delta$ subunit nucleic acid sequences which have been modified by, for example, an insertion, deletion, or substitution of one or more nucleotide sequences into the $\alpha_2\delta$ subunit nucleic acid sequence.

A. Transgenic Animal Production In General

For example, the present invention provides a method for gene recombination in post-mitotic cells, comprising: providing a gene transfer system comprising a DNA sequence encoding a Cre recombinase and post-mitotic target tissue comprising target nucleic acid, wherein the target nucleic acid comprises one or more site-specific recombination target sequences; and introducing the gene transfer system to the target tissue, whereby recombination occurs at the one or more site-specific recombination target sequences. In one embodiment of the present invention, the DNA sequence encoding a Cre recombinase further comprises a tissue-specific promoter sequence.

In some preferred embodiments, the gene transfer system comprises a viral gene transfer system. In particularly preferred embodiments, the viral gene transfer system comprises an adenoviral gene transfer system.

In certain embodiments of the present invention, the post-mitotic target tissue comprises cardiac, skeletal muscle, brain, lung, testis, pancreas, small intestine, ovary, spleen, or kidney, although the methods of the present invention are applicable to any post-mitotic target tissue. In other embodiments, the target nucleic acid comprises a gene. In yet other embodiments, the one or more site-specific recombination target sequences comprises one or more loxP target sequences, although other site-specific recombination target sequences are contemplated by the present invention, including, but not limited to, loxP2, loxP3, loxP23, loxP511, loxB, loxC2, loxL, loxR, loxΔ86, loxΔ117, frt, dif flp, and att target sequences.

In certain embodiments of the present invention, the introducing of the gene transfer system to the target tissue, comprises injecting the gene transfer system into the target tissue.

The present invention further provides a method for gene recombination in a tissue of interest (e.g., cardiac, skeletal muscle, brain, lung testis, pancreas, small intestine, ovary, spleen, or kidney), comprising: providing a viral gene transfer system comprising a DNA sequence encoding a Cre recombinase and a tissue of interest comprising target nucleic acid, wherein the target nucleic acid comprises one or more site-specific recombination target sequences; and introducing the viral gene transfer system to the tissue of interest, whereby recombination occurs at the one or more site-specific recombination target sequences. In some embodiments of the present invention, the tissue of interest comprises post-mitotic cardiac tissue. In other embodiments, the DNA sequence encoding a Cre recombinase further comprises a tissue-specific promoter sequence. In yet other embodiments, the introducing of the viral gene transfer system to the tissue of interest, comprises injecting the viral gene transfer system into the tissue.

The present invention further provides a method for tissue-restricted gene recombination, comprising: providing a viral gene transfer system comprising a DNA sequence encoding a Cre recombinase and a tissue-specific promoter sequence and post-mitotic cardiac tissue comprising target nucleic acid, wherein the target nucleic acid comprises one or more site-specific recombination target sequences; and introducing the viral gene transfer system to the post-mitotic tissue, whereby recombination occurs at the one or more site-specific recombination target sequences. In some embodiments, the introducing of the viral gene transfer system to the post-mitotic cardiac tissue comprises injecting the viral gene transfer system into the post-mitotic tissue. In certain embodiments, the tissue-specific promoter sequence comprises an α-myosin heavy chain promoter sequence.

The present invention further provides a non-human mammal, wherein one or more tissues of the non-human mammal comprise tissue prepared according to the methods described above. In preferred embodiments, the non-human mammal is selected from the order Rodentia. In particularly preferred embodiments, the non-human mammal is selected from the group consisting of mice and rats.

The present invention further provides a non-human mammal having post-mitotic tissue comprising an altered genotype as compared to wild-type post-mitotic tissue, wherein the altered genotype is the result of tissue-specific recombination. In preferred embodiments the post-mitotic tissue comprises cardiac, skeletal muscle, brain, lung testis, pancreas, small intestine, ovary, spleen, or kidney tissue, although the present invention contemplates all other post-mitotic tissues. In some embodiments, the altered genotype comprises a gene knockout.

In addition, the present invention provides a method for screening compounds for their effect on a transgenic animal, comprising: providing a transgenic animal, wherein the transgenic animal is the non-human mammal described above and a composition comprising a test compound in a form suitable for administration to the non-human mammal; and administering the test compound to the non-human mammal. In some embodiments, the method further comprises the step of detecting a response of the non-human mammal to the test compound.

B. Transgenic Knockout Animals

This section provides descriptions of various means to produce transgenic knockout animals of the present invention. The transgenic $\alpha_2\delta$-knockout ($\alpha_2\delta$-KO) animals of the present invention may be produced by a variety of means. Where the transgenic animal is a mouse, any targeting vector containing at least a portion of $\alpha_2\delta$ nucleic acid sequences of the invention which is capable of homologously recombining into the mouse $\alpha_2\delta$ subunit gene in a manner that disrupts the mouse $\alpha_2\delta$ gene (e.g., deletion, introduction of a frameshift, premature stop codon, missense mutation, etc.) may be employed. The targeting vector may be of the replacement- or insertion-type. Replacement-type vectors contain two regions of homology with the targeted gene flanking a selectable marker and result in the insertion of the selectable marker which thereby disrupts the targeted gene. Insertion-type vectors contain a single region of homology with the targeted gene and result in the insertion of the entire targeting vector into the targeted gene.

Positive selection markers include, but are not limited to, the neo gene, the hyg gene and gpt gene, may also be used so long as the selection marker permits detection of the disruption of the wild-type $\alpha_2\delta$ subunit gene with the vector sequence. Negative selectable markers are exemplified by the dt gene, and the HSV-tk gene.

It is not necessary that the targeting vector contain a selectable marker gene as discussed above, although the use of a selectable marker is preferred. Further, it is not necessary that, if a selectable marker is employed, the targeting vector employ both a positive (e.g., neo) and a negative (e.g., dt) selectable marker gene.

The targeting vector may be introduced into a variety of host cells, e.g., oocytes, zygotes and embryonic stem (ES) cells. In a preferred embodiment, the host cell is an embryonal stem (ES) cell. Another method of introducing the vector into the animal's germ line involves using embryonic stem (ES) cells as recipients of the expression vector. ES cells are pluripotent cells directly derived from the inner cell mass of blastocysts. Vectors can be introduced into ES cells using any method which is suitable for gene transfer into cells (e.g., by transfection, cell fusion, electroporation, microinjection, DNA viruses, and RNA viruses). Once the expression vector has been introduced into an ES cell, the modified ES cell is then introduced back into the embryonic environment for expression and subsequent transmission to progeny animals. The most commonly used method is the injection of several ES cells into the blastocoel cavity of intact blastocysts. Alternatively, a clump of ES cells may be sandwiched between two eight-cell embryos. Both methods result in germ line transmission at high frequency.

Transgenes may also be introduced into ES cells by retrovirus-mediated transduction or by micro-injection. Transfected ES cells which contain the transgene may be subjected to various selection protocols to enrich for ES cells which have integrated the transgene assuming that the transgene provides a means for such selection. Alternatively, the polymerase chain reaction may be used to screen for ES cells which have integrated the transgene. This technique obviates the need for growth of the transfected ES cells under appropriate selective conditions prior to transfer into the blastocoel.

Transfected ES cells can thereafter colonize an embryo following their introduction into the blastocoel of a blastocyst-stage embryo and contribute to the germ line of the resulting chimeric animal.

The generation of transgenic $\alpha_2\delta$-KO mice need not employ ES cells. For example, embryonal cells at various developmental stages can be used to introduce transgenes for the production of transgenic animals. Different methods are used depending on the stage of development of the embryonal cell. The zygote is the best target for microinjection. In the mouse, the male pronucleus reaches the size of approximately 20 micrometers in diameter which allows reproducible injection of 1–2 picoliters (pl) of DNA solution. The use of zygotes as a target for gene transfer has a major advantage in that in most cases the injected DNA will be incorporated into the host genome before the first cleavage. As a consequence, all cells of the transgenic non-human animal will carry the incorporated transgene. This will, in general, also be reflected in the efficient transmission of the transgene to offspring of the founder since 50% of the germ cells will harbor the transgene. Micro-injection of zygotes is the preferred method for incorporating transgenes in practicing the invention.

Alternatively, targeting vectors or transgenes may be microinjected into mouse oocytes to generate mice containing a disrupted $\alpha_2\delta$ subunit gene. PCR can be employed to screen the targeted cells to identify cells containing a disrupted $\alpha_2\delta$ gene without the need to use a selectable marker and to subject the targeted cells to growth in selective medium. In addition, chimeric RNA-DNA oligonucleotides containing modified RNA residues (2'-O-methyl modification of the ribose) can be used to target mutations (e.g., the introduction of a frameshift, premature stop codon, etc.) into the $\alpha_2\delta$ gene using ES cells or oocytes to create transgenic $\alpha_2\delta$-KO mice.

Once the expression vector has been injected into the fertilized egg cell, the cell is implanted into the uterus of a pseudopregnant female and allowed to develop into an animal. Heterozygous and homozygous animals can then be produced by interbreeding founder transgenics. This method has been successful in producing transgenic mice, sheep, pigs, rabbits and cattle.

Retroviral infection can also be used to introduce transgenes into a non-human animal. The developing non-human embryo can be cultured in vitro to the blastocyst stage. During this time, the blastomeres can be targets for retroviral infection. Efficient infection of the blastomeres is obtained by enzymatic treatment to remove the zona pellucida. The viral vector system used to introduce the transgene is typically a replication-defective retrovirus carrying the transgene. Transfection is easily and efficiently obtained by culturing the blastomeres on a monolayer of virus-producing cells.

Alternatively, infection can be performed at a later stage. Virus or virus-producing cells can be injected into the blastocoele. Most of the founders will be mosaic for the transgene since incorporation occurs only in a subset of cells which form the transgenic animal. Further, the founder may contain various retroviral insertions of the transgene at different positions in the genome which generally will segregate in the offspring. In addition, it is also possible to introduce transgenes into the germline, albeit with low efficiency, by intrauterine retroviral infection of the mid-gestation embryo. Additional means of using retroviruses or retroviral vectors to create transgenic animals known to the art involves the micro-injection of retroviral particles or mitomycin C-treated cells producing retrovirus into the perivitelline space of fertilized eggs or early embryos.

A transgenic animal of the invention which "expresses a reduced level of calcium channel $\alpha_2\delta$ subunit relative to a corresponding wild-type animal" is a transgenic animal which contains a quantity of at least one isoform of $\alpha_2\delta$ subunit that is less than, preferably 50% less than, and more preferably 90% less than, the quantity of a corresponding isoform of $\alpha_2\delta$ subunit in an isogeneic animal which contains a wild-type $\alpha_2\delta$ gene. Most preferably, the transgenic animals of the invention contain a quantity of at least one isoform of $\alpha_2\delta$ subunit which is at the background level of, or is undetectable by, an Enzyme Linked Immunosorbent Assay (ELISA).

A transgenic animal of the invention which "expresses a reduced activity of calcium channel $\alpha_2\delta$ subunit relative to a corresponding wild-type animal" is a transgenic animal which contains at least one isoform of $\alpha_2\delta$ subunit that exhibits less than, preferably 50% less than, and more preferably 90% less than, the biological activity of a corresponding isoform of $\alpha_2\delta$ subunit in an isogeneic animal which contains a wild-type $\alpha_2\delta$ gene. The biological activity of $\alpha_2\delta$ subunit may be determined by methods known in the art (e.g., oocyte injection assay disclosed by Ellis et al., U.S. Pat. No. 5,407,820; Harpold et al., U.S. Pat. No. 5,429,921; and Harpold et al., U.S. Pat. No. 5,792,846, the contents of each of which are incorporated by reference). Most preferably, the transgenic animals of the invention contain at least one isoform of $\alpha_2\delta$ subunit whose activity is undetectable by an oocyte injection assay.

The transgenic $\alpha_2\delta$-KO animals provided by the present invention find several uses. For example, these animals (including heterozygous ($\alpha_2\delta$ +/−) mice which contain only one copy of the gene, as well as homozygous ($\alpha_2\delta$ +/−) mice which lack both copies of the gene) may be used as murine models of cancer (e.g., lung cancer, breast cancer, etc.), human neurological diseases (e.g., epilepsy, migraine, episodic ataxia, etc.), human cardiovascular diseases (e.g., cardiac arrhythmia, angina pectoris, etc.), and human autoimmune disease (e.g., LEMS).

Experimental

The following examples serve to illustrate certain preferred embodiments and aspects of the present invention and are not to be construed as limiting the scope thereof. Unless otherwise mentioned, all molecular manipulations (e.g., DNA and RNA isolation, screening cDNA libraries, Northern and Southern blot analyses, PCR, etc.) were performed using standard methods (See e.g., Sambrook et al. [1989], supra).

In the experimental disclosure which follows, the following abbreviations apply: ° C. (degrees Centigrade); rpm (revolutions per minute); IM (intramuscular); IP (intraperitoneal); IV (intravenous or intravascular); SC (subcutaneous); $H_2O$ (water); aa (amino acid); bp (base pair); kb (kilobase pair); kD (kilodaltons); gm (grams); μg (micrograms); mg (milligrams); ng (nanograms); μl (microliters); ml (milliliters); mm (millimeters); nm (nanometers); μm (micrometer); M (molar); mM (millimolar); μM (micromolar); nM (nanomolar); U (units); V (volts); MW (molecular weight); μCi (microcurrie); sec (seconds); min(s) (minute/minutes); hr(s) (hour/hours); ab (antibody); HCl (hydrochloric acid); $MgCl_2$ (magnesium chloride); KCl (potassium chloride); NaCl (sodium chloride); $OD_{280}$ (optical density at 280 nm); PAGE (polyacrylamide gel electrophoresis); PCR (polymerase chain reaction); RT-PCR (reverse transcription PCR); SDS (sodium dodecyl sulfate); Tris (tris(hydroxymethyl) aminomethane); EDTA (ethylenediaminetetraacetic acid); w/v (weight to volume); v/v (volume to volume); SSCP (single strand conformation polymorphism analysis); ATCC (American Type Culture Collection, Manassas, Va.); Bio-Rad (BioRad, Richmond, Calif.); Sigma (Sigma Chemical Co., St. Louis, Mo.); Boehringer-Mannheim, (Boehringer-Mannheim, Indianapolis, Ind.); Scan Analytics (Scan Analytics Corp., Vienna, Va.); Oncor (Oncor, Gaithersburg, Md.); Applied Biosystems (Applied Biosystems, Foster City, Calif.); Clontech (Clontech, Palo Alto, Calif.); Gibco-BRL (Gibco-BRL, Gaithersburg, Md.); Amersham (Amersham Life Sciences, Arlington Heights, Ill.); BioServe (BioServe Ltd, Laurel Md); FMC (FMC BioProducts, Rockland Me.); Invitrogen (Invitrogen, Carlsbad Calif.); Kodak (Kodak, Rochester, N.Y.); Life Technologies (Life Technologies, Rockville, Md.); DNAStar (DNAStar Inc., Madison, Wis.); Bio 101 (Bio 101, Inc., Vista, Calif.); Ambion (Ambion, Austin, Tex.); and Axon Instruments (Axon Instruments, Foster City, Calif.).

EXAMPLE 1

Positional Cloning of the $\alpha_2\delta$ Subunit Gene

A ~700 kb clone contig was constructed covering the tumor suppressor gene region on human chromosome 3p21.3 defined by extensive allelotyping (Wei et al., supra] and overlapping homozygous deletions in lung and breast cancers (Wei et al. supra; Sekido et al., Oncogene 16(24) :3151-7 [1998]). This cloned DNA was used to isolate 17 resident genes by conventional laboratory techniques (Wei et al., supra). The 700 kb clone contig was sequenced by The WU Sequencing Center (St Louis, Mo., USA) and The Sanger Sequencing Centre (Hixton, UK) (FIG. 1 provides the GenBank accession numbers of sequences). The ~700 kb sequence and in silico methods were used to detect and isolate additional 9 genes residing in the ~700 kb sequence bringing the total number of cloned genes to 26. Eight of these genes were encoded in the critical 120 kb region defined by the recently discovered small nesting homozygous deletion in breast cancer cell line and primary tumor HCC1500 (Sekido et al., supra). The most centromeric of these genes (the $\alpha_2\delta$ gene) was interrupted by the centromeric breakpoint of the homozygous nested deletion (Sekido et al., supra), and spanned about 140 kb of genomic DNA (FIG. 1).

A cosmid probe (LUCA8; GenBank accession # Z84495) representing a large intron of the gene also included the chromosome 3 framework genetic marker, D3S1568 (also called LUCA8.2, D3S4614), allocated at a 68 cM distance from the telomere of the short arm on the chromosome 3 genetic map corresponding to the 3p21.3 band (FIG. 1).

The eight critical genes were extensively analyzed by bioinformatics methods and the interrupted large gene was identified as encoding at least two splice isoforms of a new calcium channel $\alpha_2\delta$ gene (FIG. 1).

Fluorescent in situ hybridization (FISH) was used to determine whether the $\alpha_2\delta$ subunit gene was indeed located in the 3p21.3 region as follows. Metaphase spreads derived from 5-bromodeoxyuridine synchronized normal peripheral lymphocytes were used as a template. Probes containing LUCA8 cosmid DNA were labeled with digoxigenin 11-dUTP by nick-translation and hybridization signals were detected with rhodamine-conjugated anti-digoxigenin antibodies (Boehringer-Mannheim). The conditions of hybridization, detection of hybridization signals, and digital-image acquisition, processing and analyses were performed as previously described (Ivanov et al., Proc. Natl. Acad. Sci USA 95(21):12596–601 [1998]). Chromosomes were identified by converting DAPI-banding into G-simulated banding using the IP Lab Image Software (Scan Analytics). Rehybridization with alpha-satellite centromeric probes (Oncor) was performed to confirm chromosomal localization. FISH analysis confirmed that the $\alpha_2\delta$ gene was located in the 3p21.3 region of chromosome 3.

EXAMPLE 2

Isolation of Full-Length cDNAs Encoded by the $\alpha_2\delta$ Subunit Gene

An EST (GenBank Accession #N53512) was first detected by BLAST homology searches in the databases using the genomic sequences of contig (Wei et al., supra) cosmid LUCA11 (GenBank accession # Z84492). This EST clone was found to contain a portion of the 3' end as well as putative exons of $\alpha_2\delta$-2. Further Southern blot analysis showed that various exons of the $\alpha_2\delta$-2 gene are located on cosmid LUCA6 (GenBank Accession #Z84493), LUCA7 (GenBank Accession #Z84494, LUCA8 (GenBank Accession #Z84495), LUCA9 (GenBank Accession #Z75743), LUCA10 (GenBank Accession #Z75742), and LUCA11 (GenBank Accession #Z84495). Based on GENSCAN predictions, a primer set of LUCA11r5 (5'-CTGAGAGTGAGGATGTGGAA-3' (sense primer)(SEQ ID NO:12)), and LUCA11pr18, 5'-GTGCATCCTCATACACGTTG-3' (anti-sense primer) (SEQ ID NO: 13), was used for RT-PCR amplification for normal lung cDNA template and a 960 bp product was successfully amplified. The 1.5 kb NotI/HindIII fragment of the EST clone N53512, and the 960 bp product were used as probes on human multiple tissue Northern blots (Clontech). The screening of a million clones from a lung cDNA library (Clontech) with the 960 bp RT-PCR product yielded 120 positive clones, which were also screened by probing clone N53512 to obtain the clones with long inserts. Five clones randomly selected as single positives for the 960 bp probe, and 5 clones double positive for both probes were subcloned and sequenced. All of the 10 clones had the sequence of $\alpha_2\delta$-2, suggesting that all of the 120 clones were $\alpha_2\delta$-2. Two clones (pY720c21 and pY724c95) that covered the longest sequence were assembled and further inserted into a plasmid expression vector pcDNA3.1 (Invitrogen) by standard methods (See below for additional details).

The EST was sequenced using methods known in the art. Briefly, cDNA clones were sequenced on an Applied Biosystems 373 and 377 DNA sequencers (Stretch) using Taq Dyedeoxy Terminator Cycle Sequence kits (Applied Biosystems) with either vector or clone-specific walking primers. This EST was first used as probe on commercial multiple tissues RNA Northern blots to estimate the size(s) of the mRNA(s) and to identify tissues with high expression.

For mRNA expression analyses, Northern blot hybridization was performed with $\alpha_2\delta$ cDNA probes using commercial MTN polyA RNA blots (Clontech) from a variety of adult human tissues and tumor cell lines and polyA+RNA or total RNA (JM lab) prepared from lung cancer cell lines. In these experiments, a 5.7 kb mRNA was found. In addition, the presence of the $\alpha_2\delta$ transcripts was monitored in silico by BLAST homology searches (Altschul et al., J. Mol. Biol., 215:403–410 [1990]; and Altschul et al., Nucl. Acids Res., 25:3389–3402 [1997]) in public EST databases.

Since high expression levels were detected in adult lung, testis, and brain (FIG. 2) several commercial cDNA libraries made from mRNAs of these tissues were screened to isolate overlapping cDNA clones. More than two hundred (200) cDNA clones were sequenced and shown to represent at least three distinct splice isoforms differing at the 5' end. Full-length cDNA clones for each of the three splice isoforms were then constructed and completely sequenced. In addition, cDNA clones from a commercial normal lung cDNA library (Clontech) were isolated, sequenced and shown to contain the entire open reading frame (3,435 nucleotides encoding 1,145 amino acids) of the $\alpha_2\delta$ gene protein isoform I. The molecular weight of the deduced amino acid sequence was determined to be approximately 129 kDa. As indicated below, BLAST searches and homology alignment revealed that the predicted protein shares 56% amino acid sequence identity with the human auxiliary $\alpha$-$\delta$-1 subunit (GenBank Accession #M76559) of voltage-gated $Ca^{2+}$ channels.

World Wide Web based servers were used to analyze the cDNAs and deduced protein sequences. Global sequence alignments were done using BLAST and Advanced BLAST programs (Altschul et al. (1990), supra; and Altschul et al. (1997), supra), as provided by NCBI (http://www.ncbi.nlm.nih.gov/), and BLAST2/WU Blast, provided by EMBL (http://dove.embl-heidelberg.de/Blast2/). Multiple sequence alignments, global and local, were done using the CLUSTAL version W program as provided by EMBL (http://www.bork.embl-heidelberg.de/Alignment/) and Baylor Computing Center (http://dot.imgen.bcm.tmc.edu:9331/seq-search/alignment.html).

Protein domains were discovered on the Pfam (Sonnhammer et al., Nucl. Acids Res., 26:320–322 [1998]; Sonnhammer et al., Proteins 28:405–420 [1997]) server, and membrane topology on the PSORT (Nakai and Kanehisa, Genomics 14:897–911 [1992]; http://www.imcb.osaka-u.ac.jp/nakai/psort.html; SPLIT (Juretic and Lucin, J. Chem. Inf. Comput. Sci., 38(4): 575–585 [1998]; http://drava.etfos.hr/~zucic/split.html); and TMHMM (http://www.cbs.dtu.dk/services/TMHMM-1.0/) servers.

The nucleic acid sequence of splice isoform 1 (SEQ ID NO:1) (GenBank accession #AF042792) of human $\alpha_2\delta$ subunit cDNA and its encoded amino acid sequence (SEQ ID NO:2) are provided herein. The nucleic acid sequence of splice isoform 2 (SEQ ID NO:3) (GenBank Accession #AF040709) of human $\alpha_2\delta$ subunit cDNA and its encoded amino acid sequence (SEQ ID NO:4) are also provided herein. The nucleic acid sequence of splice isoform 3 (SEQ ID NO:5) (GenBank Accession #AF042793) of human $\alpha_2\delta$ subunit cDNA and its encoded amino acid sequence (SEQ ID NO:6) are also provided herein.

Two of the cDNA clones (i.e., splice isoforms 1 and 2) predicted the same amino acid sequence (SEQ ID NOs:2 and 4) and the third clone (i.e., splice isoform 3) encoded a shorter amino acid sequence (SEQ ID NO:6) in which the first coding exon was spliced out. The longer insert sizes of 5,463 bp (splice isoform 1) and 5,482 bp (splice isoform 2) correspond to the roughly estimated major mRNA species of 5.5–5.7 kb. Splice isoform 1 and 2 cDNAs encode identical amino acid sequences (SEQ ID NOs:2 and 4) referred to as isoform I and differ only in their 5'UTRs that are followed by identical ORFs and identical 3'UTRs. The smaller cDNA of 5,279 bp (splice isoform 3) encodes a shorter amino acid sequence (SEQ ID NO:6) referred to as isoform II. The amino acid sequence of isoform II is identical to that of isoform I but is missing the first 69 amino acids. The isoform I protein is composed of 1145 amino acids predicting a theoretical pI/Mw of 5.5/129 kD; the isoform II protein comprises 1076 amino acids predicting a pI/Mw values of 5.22/122 kD. Both isoform I and II proteins are of high complexity and are not biased against any amino acids.

EXAMPLE 3

Genomic Structure and Bioinformatics Analysis of the $\alpha_2\delta$ Gene

The exon-intron structure of the $\alpha_2\delta$ gene was obtained by pairwise alignments of the cDNAs and genomic sequences of overlapping cosmids, LUCA 6-11 (FIG. 1). So far, 37 exons (FIG. 1) were detected bounded by consensus splice sites. In addition, exon trapping technology identified several more exons in the genomic sequence that were not present in the cDNAs. This indicates the possible existence of other isoforms generated by alternative splicing. The putative promoter of the $\alpha_2\delta$ gene was identified by the PromoterScan program (Prestridge, J. Mol. Biol., 249:923–932 [1995]; http://www.crc.nus.sg:80/bio/proscan/proscan.html) in the upstream sequence on LUCA6 and verified by cloning and sequencing (GenBank Accession #AF042794). Thus, there are two sequences relevant to the LUCA6 cosmid. The first is "LU6 Z84493" or "LUCA6" and the second is "LU6Pr ZF042794" or "LUCA6 promoter region." It is contemplated that Z94493 is inclusive of the entire sequence.

A number of bioinformatics web based servers were used to analyze the cDNAs and the predicted protein sequences. A global BLAST (Altschul et al. [1990], supra; and Altschul et al. [1997], supra) analysis of the cDNAs and deduced protein sequences employing NCBI (http://www.ncbi.nlm.nih.gov) and EMBL (http://www.bork.embl-heidelberg.de) servers was carried out to compare the inventions' $\alpha_2\delta$ isoforms I and II with the (alpha)$_2$-subunit protein (1091 amino acids predicting a pI/Mw values of 5.10/123 kD) which is encoded by the previously reported human (alpha)$_2$-subunit isoform A gene (Ellis et al., Science 241 (4873):1661–4 [1988]; Williams et al., Neuron, 8(1):71–84 [1992]; Ellis et al. U.S. Pat. No. 5,686,241; and Harpold et al., U.S. Pat. No. 5,792,846). Protein and cDNA alignments of the invention's $\alpha_2\delta$ isoforms I and II with the art's (alpha)$_2$-subunit sequences show 55% identity and 65% similarity on the protein level and overall 56% identity on cDNA level. It appears that $\alpha_2\delta$-2 and $\alpha_2\delta$-1 share similar overall secondary structure, as 17 out of 22 cysteines are conserved between these proteins. In addition, as with $\alpha_2\delta$-1, $\alpha_2\delta$-2 contains multiple putative N-glycosylation sites and is likely to be glycosylated. Without intending to limit the invention to any particular theory or mechanism, this degree of homology suggests that the gene encoding the art's (alpha)$_2$-subunit cDNA and the gene encoding the invention's $\alpha_2\delta$ subunit cDNA splice isoforms 1, 2 and 3 may be different members of a new gene family.

To further characterize the $\alpha_2\delta$ subunit gene, the predicted post-translational biochemical modifications, secondary structures, and membrane topologies of protein isoforms I and II which are encoded by the $\alpha_2\delta$ gene were compared. The complexity of interactions involving the five calcium channel subunits comprising a fully functional channel is influenced by distinct post-translational biochemical modifications that include O-glycosylation, amidation, myristoylation, and, most importantly, phosphorylation of specific conserved tyrosine and serine residues. The Scan-Prosite server (http://expasy.hcuge.ch/sprot/scnpsite.html) revealed similar distributions of potential N-glycosylation, O-glycosylation, N-myristoylation, and amidation sites in both isoform I and II proteins. The distribution of potential cAMP/cGMP-dependent protein kinase phosphorylation sites, CK2 and PKC phosphorylation sites, and tyrosine kinase phosphorylation sites was also similar among both isoform I and II proteins. Without limiting the invention to any particular mechanism, these potential post-translational modifications of the $\alpha_2\delta$ proteins may add more complexity and flexibility to the variety of functions attributed to these proteins. Three putative transmembrane helices were predicted in both protein isoforms of the $\alpha_2\delta$ gene with the SPLIT 35 software (Juretic and Lucin [1998], supra; and http://drava.etfos.hr/~zucic/ split.html). Interestingly, isoform I of the $\alpha_2\delta$ gene has an additional membrane helix at the very amino terminus. Using the TMHMM server (http://www.cbs.dtu. dk/services/TMHMM-1.0/) isoform I protein was predicted to span the membrane only once at the amino terminus while isoform II was predicted to span the membrane once at the carboxy terminus. Without intending to limit the invention to any particular mechanism, this favors the single-transmembrane model for the $\alpha_2\delta$ subunit proteins. In addition, the protein binding von Willebrand factor type A domain (VWA-like domain) (Bork et al., Biochem. J., 279 ( Pt 3):908–10 [1991]) was discovered by the Pfam (Sonnhammer et al. [1998], supra; and Sonnhammer et al. [1997], supra) server (http://www.sanger.ac.uk/Pfam/) in the extracellular region at similar positions in both isoform I and II proteins (residues: 291–469, and 222–400 for $\alpha_2\delta$ isoforms I and II respectively). While not limiting the invention to any particular theory or mechanism, the VWA-like domain may facilitate the binding of the $\alpha_2\delta$ complex with the alpha 1 pore forming subunit (Walker and De Waard [1998] supra).

EXAMPLE 4

Chromosomal Mapping of the $\alpha_2\delta$ Gene Locus

The chromosomal location of the $\alpha_2\delta$ gene locus was determined by FISH as described above (Example 1) using the cosmid LUCA8 (FIG. 1) probe which represents a large intron of the gene. The $\alpha_2\delta$ gene was localized as a single locus on 3p21.3 confirming the mapping of the microsatellite marker, D3S1568, that is located in LUCA8 sequence. This region of chromosome 3p21.3 is syntenic with mouse chromosome 9 region at position 60–70 cM (homology group #25) that harbors mouse loci implicated in epilepsy, namely, Ell, ducky, and tippy indicating that the $\alpha_2\delta$ gene may be responsible for these neurological phenotypes.

EXAMPLE 5

Detection of Mouse Orthologous cDNA Sequences

BLAST searches in the mouse EST database maintained by NCBI detected two different non-overlapping ESTs (GenBank Accession ## AA000341 and AA08996) which showed 91% and 85% identity with the invention's $\alpha_2\delta$ DNA (residues 2925–3421, and 4989–5391 of splice isoform 1) respectively. These ESTs showed only limited homologies (about 50%) to the murine (alpha$_2$)-subunit genes suggesting that they represent true orthologous sequences (i.e., homologous sequences present in different organisms) of the human $\alpha_2\delta$ gene. This was further corroborated by protein alignment of the 86 amino acid ORF encoded by the EST, # AA000341 which was 96% identical to the invention's $\alpha_2\delta$ isoform I protein (residues 922–1005 of isoform I). The second EST (# AA008996) represents the 3' UTR of the mouse $\alpha_2\delta$ gene and therefore has no ORF.

EXAMPLE 6

Expression Analysis of the $\alpha_2\delta$ Gene

The expression patterns of the $\alpha_2\delta$ gene were analyzed by Northern blot hybridization of human adult tissues and tumor cell lines and by monitoring EST databases. Probes for Northern analysis were labeled with a $^{32}$P-dCTP using a random primer labelling kit (Gibco-BRL). RNA was prepared from cell lines by standard techniques (See e.g., Sambrook et al., supra). Ten micrograms of total RNA (or 2 $\mu$g of poly A+ RNA) from cell lines were electrophoresed in formaldehyde-1% agarose gel and transferred to Hybond N (Amersham), and membrane preparation, hybridization, and washing were performed as described using standard techniques (Sambrook et al. [1989] supra; Sekido et al., Cancer Res., 55:1227–31 [1995]; Sekido et al., Proc. Natl. Acad. Sci USA 93:4120–4125 [1996]; and Ivanov et al. [1998], supra). Human multiple tissue Northern blots I and II and human brain blot III all made with poly A+ RNA were purchased from Clontech and handled as the tumor cell line Northerns. The DNA probes used for the $\alpha_2\delta$ gene were: the 1.5 kb fragment (Solution # Y612) NotI/HindIII fragment of EST clone N53512 for the tumor cell line Northerns and the Multiple Tissue Blot Northerns; and for other Multiple Tissue Blot Northerns 308 bp Probe A (Solution #Y614) (LUCA 11 pr1/pr2) and 291 bp Probe B (Solution # Y615) (LUCA 11 pr3/pr4); (LUCA11pr1: CTCTACAACCCAAT-TCACCAT (SEQ ID NO:8); LUCA 11pr2: TAGATG-GCACTGGCCTTCT (SEQ ID NO:9); LUCA11pr3: ACT-CACCACCCTACTGTTC (SEQ ID NO:10); LUCA11pr4: AGCTGCCTGTTTGGTGCTA (SEQ ID NO:11)). Northern Blots were exposed first for 1 or 4 days and then for ~30 days.

A. Expression in Normal Tissues

Figure 2A:
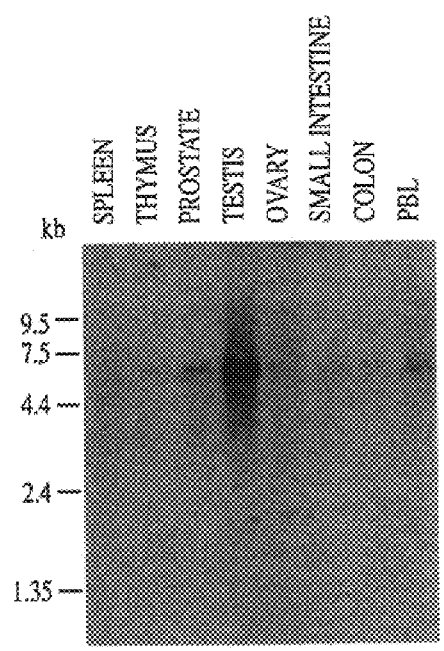
FIG. 2(A–B) shows polyA+ multiple tissue Northern blots (ClonTech) probed for $\alpha_2\delta$ expression. The tissue sources of the RNA are shown above each lane. Panel A shows a multiple tissue Northern blot with spleen, thymus, prostate, testis, ovary, small intestine, colon, and peripheral blood lymphocyte (PBL) samples, while Panel B shows a multiple tissue Northern blot with heart, brain, placenta, lung, liver, skeletal muscle, kidney, and pancreas.
Figure 2B:
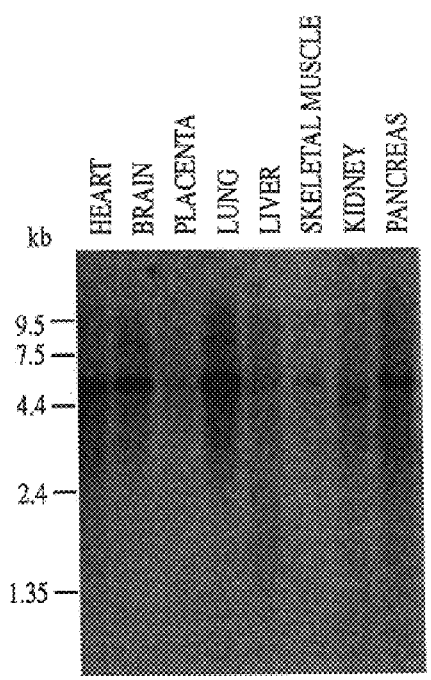

A predominant 5.7 kb $\alpha_2\delta$ mRNA was seen in all normal tissues expressing the calcium channel gene and in some cases minor larger and smaller species. The highest level of $\alpha_2\delta$ expression in normal adult human tissues was found in lung and testis, with some expression also seen in heart, brain, skeletal muscle, pancreas, spleen, prostate, ovary, small intestine, and peripheral blood lymphocytes. Northern blot results from various tissue sources are shown in FIG. 2. In this Figure, Panel A shows the results for samples from spleen, thymus, prostate, testis, ovary, small intestine, colon, and peripheral blood lymphocytes (PBL), while Panel B shows the results for samples from heart, brain, placenta, lung, liver, skeletal muscle, kidney, and pancreas. The calcium channel $\alpha_2\delta$ gene was also expressed extensively in all different areas of the brain tested in an additional multiple tissue Northern blot (e.g., thalamus, subthalamic nucleus, substantia nigra, whole brain, hippocampus, corpus callosum, caudate nucleus, and amygdala samples; results not shown).

B. Expression in Lung Cancers

A predominant 5.7 kb mRNA was also seen in lung cancer cell lines that expressed the $\alpha_2\delta$ calcium channel gene. Various cell lines were used in these experiments, including a B lymphoblastoid cell line, and lung cancer cell lines designated as NCI lines (e.g., NCI-H82). The histologies of the lines tested included small cell lung cancer (SCLC), NCI-H82 (SCLC), H146 (SCLC), H249 (SCLC), H524 (SCLC), H740 (SCLC), H1514 (SCLC), H1618 (SCLC), H2141 (SCLC), H2171 (SCLC), H2227 (SCLC), H187, H209, H345, H378, H524, H526, H865, H889, H1045, H1092, H1105, H1238, H1514, H1618, H1672, H1963, H2141, H2171; non-small cell lung cancers (NSCLC), H358 (NSCLC, adeno/bronchoalveolar), H838 (NSCLC, adeno), H1792 (NSCLC, adeno), H2077 (NSCLC, adeno), H460 (NSCLC, large cell), H1155 (NSCLC, large cell), H1299 (NSCLC, large cell), H720 (carcinoma); H28 (mesothelioma); H290 (mesothelioma), H2052 (mesothelioma), H23 (adeno), H322 (adeno), H1437 (adeno), H1666 (adeno), H2009 (adeno), H661 (large cell), H2106 (large cell), and NCI-H460 (NSCLC, large cell). These lines have been deposited with the American Type Culture Collection (ATCC).

After exposure for 1 day for poly A$^+$ RNA blots, or 4 days for total RNA blots, only a few tumor cell lines showed detectable signals. After prolonged 30 days' exposure some additional tumor lines showed expression. Overall, $\alpha_2\delta$ expression was found in 41 lung cancer samples as follows: 19 expressed the gene and 22 had no, or very weak, expression. As a function of histologic type: Small cell lung cancers: 15 expressed, 8 had no, or very weak, expression; Non-small cell lung cancers: 4 expressed, 10 had no, or very weak, expression; mesotheliomas: all 3 had no, or very weak, expression; carcinoid: 1 had no expression.

In an additional set of experiments using polyA+RNA prepared from 14 SCLC lines and 11 NSCLC lines, only about 35% of the cell lines tested showed low levels of expression and the rest no expression at all. These results collectively suggest that the $\alpha_2\delta$ gene is silenced during lung carcinogenesis.

C. EST Database Analysis

The EST matches were mostly in the testis, lung, and brain libraries (85%). Several ESTs were detected in libraries made from tumor tissues, namely, prostate, lung, and ovarian carcinomas. (NCBI, dBEST, NCI CGAP database, http://www.ncbi.nlm.nih.gov/ncicgap/). These combined results suggest that the $\alpha_2\delta$ gene is expressed in several normal tissues and that its expression is particularly high in lung and testis (as compared to other normal tissues tested). However, the dramatic reduction in the levels of expression of the $\alpha_2\delta$ subunit gene in lung cancer cell lines as compared to the levels of expression in normal lung cells suggests that the $\alpha_2\delta$ subunit gene is involved in carcinogenesis.

EXAMPLE 7

Mutation Analysis of $\alpha_2\delta$ Subunit Gene

Mutations in the $\alpha_2\delta$ subunit gene were analyzed in lung and breast cancer cell lines using Southern blot analysis, exon-PCR using intronic primers, reverse transcription polymerase chain reaction (RT-PCR) and single strand conformation polymorphism analysis (SSCP) followed by sequencing as described below.

A. Southern Blot Analysis

For Southern blot analysis, probes were labeled with a $^{32}$P-dCTP using a random primer labelling kit (Gibco-BRL). Restricted DNAs (5 or 10 $\mu$g) were run on a 0.8% agarose gel, transferred and UV cross linked to Hybond N+ membranes (Amersham). Hybridization was performed at 65° C. overnight, and the filters were washed and subjected to autoradiography. Southern blot analysis with an $\alpha_2\delta$ gene probe was performed on >100 lung cancer cell line and 26 breast cancer cell line cDNAs. This led to the discovery of another homozygous nesting deletion involving $\alpha_2\delta$ in a breast cancer cell line HCC1500 (Sekido et al., Oncogene 16:3151–3157 [1998]).

B. Exon-PCR-SSCP

To perform Single Strand Polymorphism Analysis (SSCP), PCR primer pairs (Table 1) were designed to amplify $\alpha_2\delta$ gene sequences which range in size between 80 and 298 pb. In this Table, "LU11" refers to Z84492, or LUCA11, while "LU9" refers to Z75743 or LUCA9, "LU7" refers to Z74484 or LUCA7, and "LU6 (5'UTR)" refers to Z84493 or LUCA6.

TABLE 1

Primer Pairs for SSCP Analysis of α 2 δ Gene

| Primer Name | Primer Sequence | size (bp) | Cosmid | SNP |
|---|---|---|---|---|
| c16E3 F | GAC AAG CCA CCC CTT ACC TAC (SEQ ID NO:14) | | | |
| c16E3 R | GCA GAG CCC AGT TCT GGC TG (SEQ ID NO:15) | 228 | LU11 | |
| c16E4 F | CCA GCA TAG AGT GGT CAG TG (SEQ ID NO:16) | | | |
| c16E4 R | AGT ACC CTG TCC ATT GCC TG (SEQ ID NO:17) | 210 | LU11 | |
| c16E5 F | GGC AGG TAG CAC TGA TGG TC (SEQ ID NO:18) | | | |
| c16E5 R | TTG GAG CCA CTG AGT GGA AG (SEQ ID NO:19) | 217 | LU11 | |
| c16E6 F | GTG GCT TAC GGT CCT CAC TC (SEQ ID NO:20) | | | |
| c16E6 R | TGT GCT GGG AGT CGC GGC TG (SEQ ID NO:21) | 169 | LU11 | |
| c16E7 F | ACC ACT GGA CTG CCT GCG GTG (SEQ ID NO:22) | | | |
| c16E7 R | CAG GGC TGG CAG TGC TAC AC (SEQ ID NO:23) | 226 | LU11 | |
| c16E8F | ACT GCC AGC CCT GTG ACC ATG (SEQ ID NO:24) | | | |
| c16E8R | CCA TCT CCA GTC CAG GCA TC (SEQ ID NO:25) | 229 | LU11 | yes |
| MJE2F | TTC GAC AGG ACA CAG CCC AG (SEQ ID NO:26) | | | |
| MJE2R | TGC TGG GTA GAC AGG GGA CAG (SEQ ID NO:27) | 221 | LU11 | |
| MJE3F | AGC CCA GTC GCC TCT GCA AG (SEQ ID NO:28) | | | |
| MJE3R | TGG ATA CAG CTG GCT GCG CC (SEQ ID NO:29) | 235 | LU11 | |
| MJE4F | CCT TAC CCT AAC AGA GGC ATC (SEQ ID NO:30) | | | |
| MJE4R | AAC CTC ACG TGT TCT CCT GC (SEQ ID NO:31) | 189 | LU11 | |
| MJE5F | TGG GCA GGA GAA CAC GTG AG (SEQ ID NO:32) | | | |
| MJE5R | CTG GTG ATG GTC ACA GGA GC (SEQ ID NO:33) | 236 | LU11 | |
| MJE6F | AGG CCA CTC ACC ACC CTA CTG (SEQ ID NO:34) | | | |
| MJE6R | TCC TGG GTA CAC CAA GCC AG (SEQ ID NO:35) | 259 | LU11 | |

TABLE 1-continued

Primer Pairs for SSCP Analysis of α 2 δ Gene

| Primer Name | Primer Sequence | size (bp) | Cosmid | SNP |
|---|---|---|---|---|
| MJE7F | GGA GGG CTG AGA GCT GCC TG (SEQ ID NO:36) | | | |
| MJE7R | TTG AGG TTA CTG CTG TGG CCA C (SEQ ID NO:37) | 235 | LU11 | |
| MJE8F | CTG GTG GCC ACA GCA GTC AC (SEQ ID NO:38) | | | |
| MJE8R | GGA TGG CCA GTT GAA CAT ACG (SEQ ID NO:39) | 183 | LU11 | |
| g26MJ2FA | TTC GAC AGG ACA CAG CCC AG (SEQ ID NO:40) | | | |
| g26MJ2RA | GTG CTG GGT AGA CAG GGG ACA GG (SEQ ID NO:41) | 222 | LU11 | yes |
| g26MJ5F | TGG GCA GGA GAA CAC GTG AG (SEQ ID NO:42) | | | |
| g26MJ5RA | CTG GTG ATG GTC ACA GGA GC (SEQ ID NO:43) | 235 | LU11 | |
| LU9 F | ACC CCT GGC TTC TGC TTC CTT (SEQ ID NO:44) | | | |
| LU9 R | ACA CTG CCC TCA TGG TAC AG (SEQ ID NO:45) | 221 | LU9 | yes |
| LU10-1 F | ACC TCC CTG TGC TCT GTC CCT CA (SEQ ID NO:46) | | | |
| LU10-1 R | AAT CCA CGC ATG GAT GGG CA (SEQ ID NO:47) | 150 | LU9 | |
| LU10-2 F | TGA GCA GCT AGT GCT GAG GCC TCT (SEQ ID NO:48) | | | |
| LU10-2 R | CAG CAA GGA GGT GTG GCT CAG GA (SEQ ID NO:49) | 117 | LU9 | |
| gene X 1F | ACT CCA AGC AGT GTG AGT GC (SEQ ID NO:50) | | | |
| gene X 1R | GAA GGA AGT TGT TGC CTG GAA (SEQ ID NO:51) | 261 | LU9 | |
| gene X 2F | CAG GTG TGG AAA TAA GCA GG (SEQ ID NO:52) | | | |
| gene X 2R | CAT CTT CTT GCA GCT CCT TG (SEQ ID NO:53) | 124 | LU9 | |
| gx LU 9 4F | TGC CCT TGT TAC AGT CAT CTC CA (SEQ ID NO:54) | | LU9 | |
| gx LU 9 3F | TAA GAT GAA AAG CCA GCC AGC TG (SEQ ID NO:55) | | LU9 | |
| genx LU9 2F | GTC TCC TCT TTG GAC AGA TTC TG (SEQ ID NO:56) | | | |
| genx LU9 2R | TGG AGA TGA CTG TAA CAA GGG CAC (SEQ ID NO:57) | 115 | LU9 | |
| gx LU9 3R | AAG AGG AGA CTT CCC AGT CTC TTG (SEQ ID NO:58) | | LU9 | |
| g26 Ef | CTG CAT ACA GGA TGC AGC ACT G (SEQ ID NO:59) | | | |
| g26 Er | GCT CAC CTC ACG GAG CTG CTG CGA (SEQ ID NO:60) | 88 | LU7 | yes |
| GX H f | TGT TCA GCC CAG GGA AGC GAA GC (SEQ ID NO:61) | | | |
| GX H r | ACT TAC AGC CCC CGT GGC TCT AG (SEQ ID NO:62) | 197 | LU6 (5'UTR) | |
| -1 ex 1F | CCT GGC TCT GGA AGA ATC TA (SEQ ID NO:63) | | | |
| -1 ex 1R | CAG AAA AGG AGG CAT GCT GA (SEQ ID NO:64) | 298 | LU6 (5'UTR) | |
| -1 ex 2F | AAG CGA GTG GCT GCA GAG (SEQ ID NO:65) | | | |
| -1 ex 2R | CTA AGC GGA AAC CTG GGC A (SEQ ID NO:66) | 80 | LU6 (5'UTR) | |

Each pair of primers (prepared by Gibco-BRL; BioServe; see Table) was tested for the optimal cycling conditions by running the product on a 4% 3:1 Nu-Sieve agarose gel (FMC). A typical cycling program included: 3 minutes at 95° C., 35 cycles of 1 minute at 95° C., 1 minute at the optimal annealing temperature, 1 minute at 72° C. followed by 7 minutes at 72° C. CEPH family-heads DNA was used as positive control; homozygously deleted cell line DNAs was used as negative control. PCR products were eventually cloned by means of TA Cloning Kit (Invitrogen). The radioactive reaction was performed in a total reaction volume of 12.5 μl containing 100 ng of genomic DNA, 12.5 pmol of each primer, 200 μM dNTPs, 1.5 mM $MgCl_2$, 1.25 nCi $^{35}S$-dATP. After heat denaturation (8 min at 90° C.) in formamide buffer (Stop Solution, Amersham), PCR products were run overnight in a 0.5×MDE gel (FMC), 0.6×TBE, at room temperature, 8 W constant power; blotted, dried and exposed to autoradiography film (X-OMAT AR, Kodak).

C. RT-PCR and SSCP

PCR amplified exons or RT-PCR amplified mRNA fragments were subjected to SSCP analyses followed by sequencing when gel shifts were evident as follows. Random-primed, first-strand cDNAs were synthesized from total RNA (1–3 μg/20 μl reaction) using Superscript II (Life Technologies) according to the manufacturer's instructions. All of these samples were shown to successfully amplify for glyceraldehyde 3-phosphate dehydrogenase (GAPDH) cDNA as a control test of the quality of the random primed cDNA. One μl of the random-primed cDNA was subjected to non-nested PCR in a volume of 20 μl containing 1 μM of each primer; 250 mM of dGTP, dATP, and dTTP; 25 mM of "cold" dCTP; 0.05 μl of 3000 mCi/mmol [32P]dCTP (Amersham); 1×reaction buffer (Life Technologies); 2.0 mM MgCL; 5% DMSO; and 1.25 of Taq polymerase in a Perkin-Elmer 9600 thermocycler, using 23 primer sets amplifying the Calcium Channel gene (CACNA2D2) open reading frame exons provided coverage for mutation scanning from nt 164 to 3679 of the AF040709 sequence, as shown in Table 2.

TABLE 2

Primers Used for Single Strand Conformation Polymorphism (SSCP) and RT/PCR cDNA Analysis of a2d-2 Gene (Nucleotides refer to the AF040709 sequence location)

| Forward Primers | 5'---> 3' | Nucleotides | Reverse Primers 5'---> 3' | | Nucleotides | Product Size |
|---|---|---|---|---|---|---|
| g97F | GCA TCT TGA ATG GAA ACA TGG C (SEQ ID NO:67) | 164–185 | 16GR | TCG ACC TCC TGC TCC AGA (SEQ ID NO:68) | 408–425 | 262 |
| I5GF | AGC ACA CGA TGC AGC ACT G (SEQ ID NO:69) | 380–398 | 15GR | CTT CTC CAC CAA CTT CTG AG (SEQ ID NO:70) | 515–534 | 155 |
| LO9s12075 | ACA ACC GGA ACC TGT TCG A (SEQ ID NO:71) | 479–497 | e80R | CGT CAT AGT ACA CGA TGT CTT C (SEQ ID NO:72) | 649–670 | 192 |
| e79F | ATG CTG CAG AGA ACT TCC AG (SEQ ID NO:73) | 596–615 | L11pr42 | TGA AGT TTG GGT CCT CGA TG (SEQ ID NO:74) | 753–772 | 177 |
| pr5 | CTG AGA GTG AGG ATG TGG AA (SEQ ID NO:75) | 698–718 | pr44 | AAG ACC TGC CAC AGC AGT G (SEQ ID NO:76) | 911–929 | 232 |
| pr51 | GTG TTC ATG GAA AAC CGC AG (SEQ ID NO:77) | 880–899 | pr52 | CCA CTC ACA TCC ACG ATG ATG (SEQ ID NO:78) | 1059–1079 | 200 |
| pr53 | CTG TAC GAT GTC CGA AGG AGA C (SEQ ID NO:79) | 997–1018 | pr54 | TGT GAA GCA TGA CAC AGG CTG (SEQ ID NO:80) | 1189–1209 | 213 |
| pr55 | ATC TGT CTG CGA GAT GCT GG (SEQ ID NO:81) | 1116–1135 | pr16 | TTC TGC AGC TGG TCA AAG GG (SEQ ID NO:82) | 1313–1331 | 216 |
| pr57 | CGC AAC AAG AAG GTG TTC AAG (SEQ ID NO:83) | 1231–1251 | pr58 | GCC CCA CGG AGA AAG TAA AC (SEQ ID NO:84) | 1449–1468 | 238 |
| pr59 | TGT TCA CGG ATG GTG GTG AG (SEQ ID NO:85) | 1373–1392 | pr60 | TTC CTG TGT GTT GAT GCG G (SEQ ID NO:86) | 1554–1572 | 200 |
| g81F | TTG AGA TCC CTT CCA TCG G (SEQ ID NO:87) | 1529–1547 | g82R | GCT GGT TCT TCT TTT CCC CAG (SEQ ID NO:88) | 1718–1738 | 210 |
| g83F | GTG GTA ACA GGG ACC CTC CCT (SEQ ID NO:89) | 1672–1692 | g84R | AGA TTG GGG TGC AGC AAC AC (SEQ ID NO:90) | 1852–1871 | 200 |
| g85F | GCT ATG TGT TTG CCA TTG ACC (SEQ ID NO:91) | 1820–1840 | g86R | CTA TGT ACC TCT CAT CCA GGG AC (SEQ ID NO:92) | 2013–2038 | 219 |
| g87F | CAT GAT TGA TGG CAA CAA GG (SEQ ID NO:93) | 1965–1984 | g88R | GGG GAG CAG GAA CTC AAA ATA C (SEQ ID NO:94) | 2163–2184 | 220 |
| g89F | GCC AAT CTC AGT GAC CAG ATC C (SEQ ID NO:95) | 2131–2152 | g90R | AGG TTG TGC AGA AGG AAG TTG (SEQ ID NO:96) | 2328–2348 | 218 |
| g91F | AGA AAG TGA CTC CAG ACT CCA AG (SEQ ID NO:97) | 2297–2319 | g92R | TTG AAG GGC TCA GGG TTC TC (SEQ ID NO:98) | 2497–2516 | 220 |
| pr61 | GGA TCT CAA CAC GTA CAG CCT AC (SEQ ID NO:99) | 2403–2425 | pr62 | GGA TGC CCA CAG TGT CAT TC (SEQ ID NO:100) | 2607–2626 | 224 |
| pr63 | CCC TTC AAT GCC AGC TTC TAC (SEQ ID NO:101) | 2508–2529 | pr64 | AAC TTC TCA GCC CAA GCC TC (SEQ ID NO:102) | 2704–2723 | 216 |
| pr65 | AAT GAC ACT GTG GGC ATC CTC (SEQ ID NO:103) | 2608–2629 | pr66 | TTA ACC TCG CAG TCC ATC TCA C (SEQ ID NO:104) | 2789–2810 | 203 |
| pr67 | ACC AAG ACC AGC CTC AGA AGT G (SEQ ID NO:105) | 2750–2771 | pr68 | ATA GGA CTC CTT GCG GGT GTA G (SEQ ID NO:106) | 2952–2973 | 224 |
| pr69 | AGG TGG ATG CCA ACC TGA TG (SEQ ID NO:107) | 2908–2928 | pr70 | CGT AGA GAA GCT GCT GGA ACA G (SEQ ID NO:108) | 3100–3122 | 215 |
| pr71 | CAC CGT TGC AGA TTT CCT TAA C (SEQ ID NO:109) | 3045–3066 | pr72 | AGT TTC CGC AGT CGA TGA TG (SEQ ID NO:110) | 3252–3272 | 228 |
| pr73 | GAA ACA GAC CCA GTA CTA CTT C (SEQ ID NO:111) | 3204–3225 | pr74 | GCG TTG TAG TCG AAG CAG AT (SEQ ID NO:112) | 3454–3473 | 270 |
| pr75 | AGC AGT GTG AGC TAG TGC AG (SEQ ID NO:113) | 3407–3426 | pr76 | AGG GTG GGA AAG GCG AAG A (SEQ ID NO:114) | 3661–3679 | 273 |

Most of these primer sets amplified fragments of <225 bp of cDNA while two amplified 270 bp of cDNA for optimal mutation detection. A modified touch-down PCR (initial denaturation at 94° C. for 2.5 min, followed by 5 cycles of 30 s at 94° C., 30 s at 68° C., 30 s at 72° C., and then 30 cycles of 30 s at 94° C., 30 s at at 72° C., and a final extension for 10 min at 72° C.) was used. The samples were heat denatured, snap chilled, and run on 0.5×Mutation Detection Enhancement (MDE) gels (FMC) with and without 10% glycerol at 5 W overnight, and subjected to autoradiography for 24 h. Shifted SSCP bands were excised from the MDE gels, and the DNA was eluted with distilled water and re-amplified using the original PCR primers. The PCR product was run on a 2% agarose gel and purified by GeneClean (Bio 101). Automated bi-directional sequencing was performed by ABI 377 Dye Terminator cycle sequencing. Sequences were analyzed and compared to wild-type Calcium channel gene (CACNA2D2) sequences with DNAStar software.

Fifty-nine lung cancer cell line samples (33 small cell lung cancer and 26 non-small cell lung cancers) were tested for mutations by this SSCP method and no amino acid altering mutations were found. As a control normal lung cDNA was also run. In the course of cDNA and SSCP sequencing, at least four (4) single nucleotide polymorphisms (SNPs) were recorded. The previously known microsatellite polymorphic locus, D3S1568, was detected in the sequence of a large intron of the $\alpha_2\delta$ gene.

However, 19 (19/59, i.e., 32%) of the lung cancer cDNA samples gave a blank signal on repeated testing of their cDNAs for several of the primer sets. Without limiting the invention to any particular theory or mechanism, these results indicate either extremely low levels of expression of the gene in lung cancer cell lines and/or modifications in the cDNA which disrupt the open reading frame.

EXAMPLE 8

Generation of Polyclonal Antibodies Against $\alpha_2\delta$ Subunit Isoform I and Expression of $\alpha_2\delta$ in Lung Cancer Cells The coding region of the cDNA splice isoform 2 (SEQ ID NO:3) (3,442 bp, nt 175 to nt 3,616) was cloned into each of the following three expression vectors: pcDNA3.1 His C (Invitrogen) at the BamHI/NotI site (CMV expression vector), pLJ17 (pAdE1/CMV) at the BamHI/NotI site (adenovirus shuttle vector), and pRev-TRE vector (ClonTech) at the BamHI/SalI site (retrovirus tetracycline regulatable vector). The 3,442 bp construct was subjected to in vitro translation giving a product of ~130 Kd which compares well to the calculated molecular weight of 129,268 Daltons.

NCI-H1299 non-small cell lung cancer cells were transfected with plasmid pcDNA3.1($\alpha_2\delta$) (i.e., the above-described pcDNA3.1 pIHisC plasmid into which the cDNA splice isoform 2 was cloned) and tested in in vitro translation experiments using $^{35}$S-methionine in an in vitro transcription/translation system (TNT Coupled Reticulocyte Systems, Promega). For transfection experiments, NCI-H1299 cells (3×10$^5$) were seeded in 3.5 cm culture dishes for 24 h in RPMI 1640 containing 5% fetal bovine serum. Then, 1 μg of cloned DNA was introduced into the cells using the lipofectamine reagent (Gibco-BRL). For protein expression after transfection, cells were harvested 48 hrs later and lysed in 80 μl of sample buffer (50 mM Tris, pH 6.8; 1% SDS, 10% glycerol and 0.3M of β-mercaptoethanol). NCI-H1299 cells were used for these studies because they do not express endogenous $\alpha_2\delta$-2 mRNA or protein, and are homozygous for multiple polymorphic markers in the 600 kb homozygous deletion region, and thus have undergone loss of heterozygosity for this region.

After transient expression, Western blot analysis using affinity purified rabbit polyclonal anti-peptide antibody which was raised against $\alpha_2\delta$ subunit amino acids 161–181 (peptide A) of SEQ ID NO:4 was used to detect the expressed protein. Western blots showed a band at ~150 Kd and also at ~300 Kd area in a non-reduced 4–15% gradient PAGE using the polyclonal antibody against peptide A. It is possible that the increase in the apparent molecular weight (i.e., approximately 129 to 150 kDa) compared to the conceptually translated protein and the in vitro translated protein is the result of N'-glycosylation, in agreement with multiple putative N-glycosylation sites in the $\alpha_2\delta$-sequence which represent known properties of the $\alpha_2\delta$-1 protein (Gurnett et al., Neuron 16(2):431–440 [1996]). Endogenous $\alpha_2\delta$-2 protein of 150 kDa was also detected in some lung tumor cell lines using the same antibody, further confirming that the conceptual translation and anti-peptide antibody preparation were correct.

After reducing the protein with beta-mercaptoethanol only a single band was observed at ~150 Kd. This is in contrast to the result with the previously reported (alpha$_2$)-subunit gene (Ellis et al. [1988], supra; Williams et al. [1992], supra; Ellis et al., U.S. Pat. No. 5,686,241; and Harpold et al., U.S. Pat. No. 5,792,846) which showed a reduction in size after treatment with a reducing agent. While not intending to limit the invention to any particular mechanism, these results demonstrate that while the previously reported human (alpha$_2$)-subunit gene is processed into two subunits, the $\alpha_2\delta$ subunit gene of the invention may be processed in a similar or different manner.

FIG. 3 provides Western blot data showing the results of in vitro transcription and translation of $\alpha_2\delta$-2 experiments. In Panel A, lane 1 contains the products of in vitro transcription and translation of $\alpha_2\delta$-2 in expression vector pcDNA3.1. In lane 2, no DNA was added in the same reaction. The arrow indicates the expected approximately 130 kd product. In Panel B, results from Western blot analysis of transfection of NCI-H1299 cells with $\alpha_2\delta$-2 are shown. Lane 1 shows the results for NCI-H1299 cells with $\alpha_2\delta$-2 in expression vector pcDNA3.1. Lane 2 shows the results for NCI-H1299 cells transfected with pcDNA3.1 vector alone. In these Westerns, affinity-purified anti-$\alpha_2\delta$-2 peptide antibody was used to detect the protein product. The arrow in the Figure indicates the expected protein product. Sizes of the prestained protein molecular weight markers are indicated on the right. In Panel C results are shown for protein from tumor lysates (loaded at 40 μg per lane). Lane 1 contains protein lysate from NCI-H2077 cells (adenocarcinoma), lane 2 contains lysate from NCI-H383 cells (adenocarcinoma), lane 3 contains lysate from NCI-H2106 cells (large cell neuroendocrine carcinoma), and lane 4 contains lysate from NCI-H1299 cells (large cell carcinoma). As indicated above, the results shown in Panel C indicate that endogenous $\alpha_2\delta$-2 protein of 150 kDa was detected in some lung tumor cell lines (using the same antibody as with other preparations), further confirming that the conceptual translation and anti-peptide antibody preparation were correct.

EXAMPLE 9

Regulation of Calcium Ion Flux In Vitro by the $\alpha_2\delta$ Subunit Through Cancer Cells and Oocytes The bioinformatics analysis of the $\alpha_2\delta$ subunit gene and its isoforms clearly demonstrated that this is a new human gene coding for at least two $\alpha_2\delta$ subunits of the voltage-gated plasma membrane calcium channels. It is the inventors' consideration that the single polypeptide products of the gene are post-translationally cleaved into the $\alpha_2$ and $\delta$ polypeptide subunits which, after extensive biochemical modifications, form the $\alpha_2\delta$ protein complex that is necessary to assemble a fully functional plasma membrane calcium channel(s).

Two series of experiments are conducted to ascertain the subunit function of the gene products in regulating calcium ion flux in vitro across cell membranes. First, cDNA sequences (which correspond to ORFs of GenBank Accession ## AF040709, AF042792 and AF042793) and which code for both isoform I and isoform II variants respectively were inserted into the tetracycline controlled episomal expression vectors Tet OFF (Clontech) or pETE. In the Clontech Tet OFF system the gene is not expressed (or expressed at very low levels) in the presence of doxycycline and expressed at very high levels in the absence of doxycycline. The pETE vector is derived from the commercially available Tet OFF vector (Clontech) by inserting an EBNA-1 element to confer an episomal property on the vector. The pETE vectors were then transfected into lung cancer (e.g., NSCLC NCI-H1299, H1607, and A549) and nasopharyngeal cancer cells (HONE-1) which were specifically engineered to constitutively express the tetracycline-controlled transcription activator (TA) by infecting the tumor cells with a retrovirus expressing TA. In this system the transfected genes were highly-to-moderately expressed (as determined by Northern analysis) in the absence of tetracycline and not expressed at all in the presence of tetracycline or its analog, doxycycline. These results demonstrate high level expression in vitro in cancer cells of each of isoforms I and II of the $\alpha_2\delta$ subunit protein.

Clonal NCI-H1299 cell lines constitutively expressing high levels of the $\alpha_2\delta$ subunit polypeptide have already been developed. Clonal cell lines which express high levels of the transfected $\alpha_2\delta$ subunit proteins in a tetracycline controlled fashion are developed by selecting and clonally expanding only transfected cell which express high levels of the subunit. These clonal cell lines are used to measure calcium ion fluxes in the presence and absence of tetracycline or doxycycline special fluorescent staining as previously described (McEnery [1998], supra). Voltage dependent calcium channels:structural insights into channel function, pharmacology, and assembly in health and disease (McEnery [1998], supra). In this setting, it may be established whether the expression of the $\alpha_2\delta$ subunit gene products in cells which otherwise lack expression of endogenous $\alpha_2\delta$ subunit gene would increase calcium entry into the cells as compared to control cells (i.e., a corresponding cell which has not been transfected with the expression vector that encodes the $\alpha_2\delta$ subunit).

Secondly, frog oocytes expressing calcium channels that do not contain $\alpha_2\delta$ subunits may be prepared using methods known in the art (See e.g., Ellis et al. U.S. Pat. No. 5,686,241, and Harpold et al., U.S. Pat. No. 5,792,846, the contents of both of which are herein incorporated by reference). These oocytes are used to test whether a fully functional calcium channel may be reconstituted. This is achieved by introducing recombinant plasmids expressing $\alpha_2\delta$ subunit proteins into these frog oocytes and by measuring calcium fluxes in the transfected cells as compared to control cells. Controls include oocytes which express calcium channels that do not contain $\alpha_2\delta$ subunits and which are not transfected with recombinant plasmids that express $\alpha_2\delta$ subunit proteins. Another control includes oocytes which express a calcium channel that contains $\alpha_2\delta$ subunits and which are not transfected with the recombinant plasmids that express $\alpha_2\delta$ subunit proteins.

EXAMPLE 10

Electrophysiologic Studies

In these experiments, co-expression of $\alpha 1B$ and $\beta 3$ subunits was investigated. Complementary RNA (cRNA) encoding human brain $\alpha 1B$, rabbit skeletal muscle $\alpha_2\delta$-1, rabbit $\beta_3$, and $\alpha_2\delta$-2 subunits were synthesized in vitro using T7 RNA polymerase, resuspended in water at a final concentration of ~1 mg/ml and stored at $-80°$ C. until injection. Xenopus oocytes harvested by standard methods known in the art were injected with a mixtures of the following transcripts: $\alpha 1B+\beta_3$, $\alpha 1B+\beta_3+\alpha_2\delta$-1, $\alpha 1B+\beta_3+\alpha_2\delta$-2 or $\alpha_2\delta$-2 alone (approximately 50 ng total cRNA/oocyte). Two days later, the oocytes were analyzed using standard two-electrode voltage-clamp technique with 5 mM $Ba^{2+}$ as a charge carrier, as known in the art. The holding potential was $-120$ mV. Currents were recorded in response to test potentials ranging from $-110$ to $+100$ mV, filtered at 200 Hz, then analyzed using pClamp 6.04 (Axon Instruments) and Origin (Microcal) software. Leak and capacitance currents were subtracted on-line with a P/4 protocol.

For the studies of coexpression with $\alpha 1C$ and $\alpha 1G$ subunits, cRNA of either $\alpha 1C$, $\alpha 1G$, or $\alpha_2\delta$-2 cDNA was synthesized using Ambion Megascript Kit according to the supplier's protocol (Ambion). Due to low expression of wild-type $\alpha 1C$, the modified cDNA, $\Delta$N60, which is truncated by 60 amino acids at the N-terminal end of the rabbit cardiac $\alpha 1$ subunit was used. The rat brain $\alpha 1G$ cDNA was contained in the vector pGEM-HE. Fifty nl of cRNA (5 ng for $\alpha 1C$; 5 ng for $\alpha 1G$; and 2.5 ng for $\alpha_2\delta$-2) of either $\alpha 1C$ alone, $\alpha 1C$ plus $\alpha_2\delta$-2, $\alpha 1G$ alone, or $\alpha 1G$ plus $\alpha_2\delta$-2, were injected into each oocyte using a Drummond Nanoject pipette injector (Parkway, Pa.). Expression of injected cRNA was measured from the 4th day after injection for $\alpha 1C$ alone or $\alpha 1C$ plus $\alpha_2\delta$-2, and the 6–7th day after injection for $\alpha 1G$ alone, or $\alpha 1G$ plus $\alpha_2\delta$-2 using the two-electrode voltage clamp method known in the art. Currents were measured in either 40 mM $Ba^{2+}$ solution (40 mM $Ba(OH)_2$, 50 mM NaOH, 1 mM KOH, and 5 mM HEPES, adjusted to pH 7.4 with methanesulfonic acid) for L-type currents, or 10 mM $Ba^{2+}$ solution (10 mM $Ba(OH)_2$, 80 mM NaOH, 1 mM KOH, and 5 mM HEPES, adjusted to pH 7.4 with methanesulfonic acid) for T-type currents. Data were sampled at either 2 KHz for L-type currents, or 5 KHz for T-type currents using the pClamp 6 system via a Digidata 1200 A/D converter (Axon Instrument). Leak currents were subtracted using a P/+4 for L-type currents or a P/−6 for T-type currents.

Figure 4:
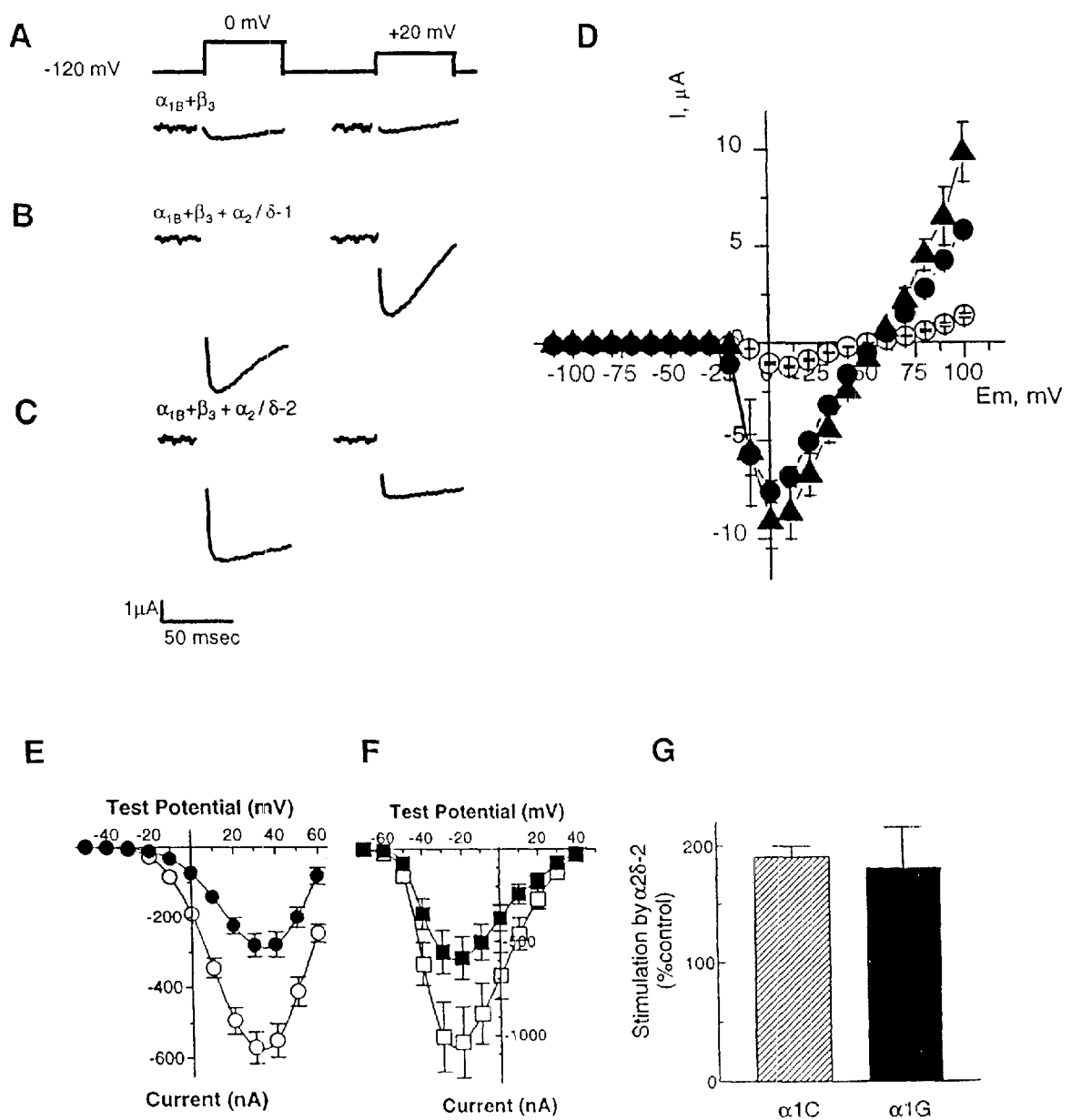
FIG. 4(A–G) provides data obtained from Xenopus oocyte expression system tests. Panel A provides representative records of barium currents evoked by step depolarization from –120 to 0 mV and +20 mV, for oocytes injected with cRNA encoding $\alpha_1B+\beta3$, while Panel B provides results for oocytes injected with cRNA encoding $\alpha_1B+\beta3+\alpha2\delta$-1, and Panel C provides results for oocytes injected with cRNA encoding $\alpha_1B+\beta3+\alpha_2\delta$-2. Panel D provides mean current-voltage curves from two independent injections (mean±EM), with $\alpha_1B+\beta3$ (open circles), $\alpha_1B+\beta3+\alpha2\delta$-1 (filled triangles), and $\alpha_1B+\beta3+\alpha_2\delta$-2 (filled circle) combinations. Panel E provides current-voltage relationships of $\alpha1C$ alone (filled circles) and $\alpha1C/\alpha2\delta$-2 (circles) induced currents. Panel F provides current-voltage relationships of $\alpha1G$ (filled squares) and $\alpha1G/\alpha2\delta$-2 (squares) induced currents. Panel G provides the average stimulation of $\alpha1C$ and $\alpha1G$ currents by co-expression with $\alpha_2\delta$-2.

Injection of oocytes with cRNA encoding the pore-forming human $\alpha 1B$ subunit together with an auxiliary $\beta_3$ subunit resulted in expression of functional N-type calcium channels in oocyte plasma membranes with a peak current of $1.0\pm0.1$ $\mu A$ (n=4) (See, FIG. 4A). Channel activity was indicated as representative inward barium currents observed in response to 0 mV and +20 mV test potentials. The magnitude of N-type currents was increased 9 fold to $9.1\pm1.4$ $\mu A$ (n=10) when $\alpha 1B$ and $\beta_3$ were co-expressed with the rabbit skeletal muscle $\alpha_2\delta$-1 subunit (See, FIG. 4B). When co-expressed with $\alpha 1B$ and $\beta_3$ subunits, the $\alpha_2\delta$-2 subunit exerted a similar effect on N-type channel expression, increasing peak current size to $7.6\pm0.6$ $\mu A$ (n=10)(See, FIG. 4C). No channel activity was observed after injection of $\alpha_2\delta$-2 cRNA alone (data not shown). By varying the test potential in the range from $-100$ mV to $+100$ mV it was established that the shape and position of current-voltage (IV) relationships were similar for all 3 subunit combinations, with the maximum current at 0 mV test potential and reversal potential at +50 mV (See, FIG. 4D).

Stimulation of N-type current expression by $\alpha 2\delta$-1 and $\alpha_2\delta$-2 subunits (FIGS. 4A–C) is similar to the previously described effect of $\alpha 2\delta$-1 on P/Q-type $Ca^{2+}$ channels formed by $\alpha 1A$ and $\beta$ subunits (De Waard and Campbell, Neuron 16(2):431–400 [1996]; and Walker and De Waard, Trends Neurosci., 21(4):148–154 [1998]), which has been shown to depend on α2δ-1 subunit glycosylation (Gurnett et al., supra). Thus, it is likely that $\alpha_2\delta$-2 subunit is glycosylated when expressed in Xenopus oocytes, as is expected from biochemical and sequence analysis. Noticeably, the $\alpha_2\delta$-1, but not the $\alpha_2\delta$-2 subunit was able to hasten N-type $Ca^{2+}$ channel inactivation. Indeed, at the end of a 50 ms test pulse to +20 mV, the size of the current was reduced to 33±10% (n=8) of the peak current for α1B+β$_3$+$\alpha_2\delta$-1, to 59±5% (n=24) of the peak current for α1B+β$_3$+$\alpha_2\delta$-2 and to 51±4% (n=15) of the peak current for α1B+β$_3$ subunit combinations.

To test for an $\alpha_2\delta$-2 effect on L-type channels, either α1C cRNA alone, or α1C plus $\alpha_2\delta$-2 cRNA were injected into oocytes. Peak currents measured during a series of test potentials were averaged (See, FIG. 4E). The results shown in Panel E correspond to experiments in which currents were evoked by a series of test pulses of −50 mV to +70 mV from a holding potential of −70 mV in 40 mM $Ba^{2+}$ solution. Average α1C currents were collected from 33 oocytes, α1C/$\alpha_2\delta$-2 currents were from 31 oocytes isolated from three different frogs. Data represent mean±SEM. The results shown in Panel F correspond to experiments in which currents were elicited by test pulses of −70 mV to +50 mV from a holding potential of −90 mV in 10 mM $Ba^{2+}$ solution. Average α1G currents were collected from 33 oocytes, α1G/$\alpha_2\delta$-2 currents were from 32 oocytes isolated from four frogs. Panel G provides the average stimulation of α1C and α1G currents by co-expression with $\alpha_2\delta$-2. When peak current amplitudes measured at +30 mV were compared, α1C/$\alpha_2\delta$-2 currents were significantly larger than α1C by 201% (t-test, P<0.001). However, there were no significant differences in the position of the IV curves, which peaked at ~+35 mV. Similar to the $\alpha_2\delta$-2 effect on α1C channels, co-injection of $\alpha_2\delta$-2 cRNA with α1G cRNA increased T-type current amplitudes by 176% (t-test, P<0.05), compared to α1G alone.

There were no significant differences in their biophysical properties including activation threshold, position of their IV curves, reversal potentials, and activation and inactivation kinetics. Based upon these experiments, it appears that the cloned $\alpha_2\delta$-2 protein is able to function as an auxiliary subunit of all three subfamilies of voltage-gated $Ca^{2+}$ channels. Since expression of the cloned T-type channels was found to be highly variable between batches of oocytes, each batch was injected with both α1 and α1α2δ-2. Stimulation by α2δ-2 was measured for each batch, then averaged.

EXAMPLE 11

In Vitro and In Vivo Growth Suppression of Tumor Cell Growth

It is the inventors' consideration that the $\alpha_2\delta$ gene by virtue of its location in the critical cancer region on human chromosome 3p21.3 and its association with small cell lung carcinoma in patients with Lambert-Eton syndrome is a strong candidate tumor suppressor gene that is involved in the causation of lung cancer and in the development of several common human malignancies including, but not limited to, lung, breast, cervical, head and neck carcinomas. The tumor growth suppression function of the $\alpha_2\delta$ subunit is analyzed using either constitutively expressed $\alpha_2\delta$ subunit or tet-controlled expression vectors which contain DNA sequences that encode at least a portion of isoform I or isoform II and which express the DNA sequences in the presence of tetracycline, as described supra (Example 9). The constitutively expressing vectors or tet-controlled vectors are transfected into lung cancer and nasopharyngeal carcinoma cells (Example 9) and the transfected cells are used to determine the effect of expression of $\alpha_2\delta$ subunits on growth of the transformed tumor cells both in vitro and in vivo.

The effect on tumor cell growth of the constitutively expressing vectors or in the presence and absence of tetracycline is assessed in vitro under cell culture conditions and in vivo by measuring tumor formation and/or growth rate in nude or SCID mice. The function of the $\alpha_2\delta$ gene as a tumor suppressor gene is determined by observing an increased rate of cell growth of transfected cancer cells in vitro in the presence either of a control vector transfected cell or of tetracycline as compared to the rate of cell growth in the absence of tetracycline. The tumor suppressor function of the $\alpha_2\delta$ gene is also confirmed in vivo by the observation that the number and/or rate of tumor formation by the transfected tumor cells in nude mice is increased in the presence or absence of tetracycline as compared to that in the presence or absence of tetracycline for tumor cells transfected with the Tet regulatable system. In the constitutively expressing system, the tumor growth rate or number is compared for tumors arising from tumor cells transfected with either the control vector or the control vector which contains a specifically constructed inactive mutant form of the $\alpha_2\delta$ gene.

EXAMPLE 12

Generation of Knockout Mice by Targeted Inactivation of the $\alpha_2\delta$ Subunit Gene Knockout mice which do not contain a functional murine orthologous $\alpha_2\delta$ gene are generated as follows. The mouse ESTs (GenBank Accession ## AA000341 and AA08996) which the inventors identified as representing sequences of the murine orthologous $\alpha_2\delta$ gene were used to screen a phage genomic library made from mouse stem cells (ES). An overlapping phage contig (about 25 kb in size) containing several exons from the carboxy terminus of the mouse gene and part of the 3' UTR was assembled and used in the construction work. Using methods known in the art, a targeting vector containing this portion of the murine ortholog of the human $\alpha_2\delta$ gene interrupted by a neo positive selection cassette is constructed. This vector is electroporated into mouse 129SVJ embryonic stem cells and the targeted DNA is integrated in a site-specific manner by homologous recombination. The targeted ES cells are injected into mouse blastocysts and placed into a pseudopregnant female for production of heterozygous mice. These mice are used for production of homozygous null mice by interbreeding and screening the progeny for the presence of the $\alpha_2\delta$ gene. Heterozygous and homozygous transgenic knockout mice are used in carcinogenesis studies (e.g., to determine whether there is a change in tumor incidence and/or growth rate compared to wild-type mice). Tumor development in multiple tissues is monitored and animals are sacrificed to remove and evaluate tumors for size, location and histology. The heterozygous and homozygous transgenic knockout mice are also used to evaluate development of neurological and cardiovascular pathology using methods well known in the art.

From the above, it is clear that the invention provides calcium channel alpha2delta ($\alpha_2\delta$) subunits and nucleic acid sequences encoding them. These compositions are useful in methods for identifying compounds that modulate the activity of calcium channels and for identifying compounds as therapeutic for disease.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art and in fields related thereto are intended to be within the scope of the invention.

What is claimed is:

1. A purified nucleic acid sequence comprising a nucleotide sequence selected from the group consisting of (a) SEQ ID NO:1 and the complement thereof, (b) SEQ ID NO:3 and the complement thereof, and (c) SEQ ID NO:5 and the complement thereof.

2. The nucleic acid of claim 1, wherein said nucleic acid sequence encodes the amino acid sequence selected from the group consisting of SEQ ID NO:2, SEQ ID NO:4, and SEQ ID NO:6.

3. The nucleic acid sequence of claim 2, wherein said nucleic acid sequence is double-stranded.

4. The nucleic acid sequence of claim 2, wherein said nucleic acid sequence is single-stranded.

5. The nucleic acid sequence of claim 1, wherein said nucleic acid sequence encodes a fusion protein.

6. The nucleic acid sequence of claim 5, wherein said fusion protein comprises a polypeptide selected from the group consisting of chloramphenicol acetyltransferase, luciferase, beta-galactosidase, green fluorescent protein, Myc protein, protein A, glutathione-S-transferase, and polyhistidine.

7. The nucleic acid sequence of claim 1, wherein said nucleic acid sequence is inserted into a recombinant expression vector.

8. The nucleic acid sequence of claim 7, wherein said expression vector is contained within a cultured host cell.

9. The nucleic acid sequence of claim 8, wherein said host cell is a eukaryotic cell.

10. The nucleic acid sequence of claim 9, wherein said eukaryotic cell is selected from the group consisting of cancer cells and amphibian oocytes.

11. A method for producing a calcium channel protein, comprising:
  a) providing:
    i) a recombinant expression vector comprising a nucleic acid sequence encoding an amino acid sequence selected from the group consisting of SEQ ID NOs: 2, 4, and 6; and
    ii) a cultured host cell; and
  b) introducing said vector into said host cell under conditions such that said host cell expresses said amino acid sequences, wherein said sequence encodes a calcium channel protein.

12. The method of claim 11, wherein said expressed amino acid sequence is recovered.

13. The method of claim 11, wherein said host cell is a eukaryotic cell.

14. The method of claim 13, wherein said eukaryotic host cell is selected from the group consisting of cancer cells and amphibian oocytes.

15. A method for coexpressing a plurality of calcium channel proteins, comprising:
  a) providing:
    i) one or more recombinant expression vectors comprising one or more nucleic acid sequences encoding amino acid sequences selected from the group consisting of SEQ ID NOs: 2, 4, and 6; and
    ii) a cultured host cell; and
  b) introducing said vectors into said host cell under conditions such that said host cell coexpresses said one or more amino acid sequences, wherein said amino acid sequences encode calcium channel proteins.

16. The method of claim 15, wherein said expressed amino acid sequence is recovered.

17. The method of claim 15, wherein said host cell is a eukaryotic cell.

18. The method of claim 17, wherein said eukaryotic host cell is selected from the group consisting of cancer cells and amphibian oocytes.

* * * * *